United States Patent
Uhlin et al.

(10) Patent No.: US 10,106,623 B2
(45) Date of Patent: Oct. 23, 2018

(54) BISPECIFIC ANTIBODIES FOR USE IN STEM CELL TRANSPLANTATION

(71) Applicants: Michael Uhlin, Falun (SE); Jonas Mattsson, Tullinge (SE)

(72) Inventors: Michael Uhlin, Falun (SE); Jonas Mattsson, Tullinge (SE)

( * ) Notice: Subject to any disclaimer, the term of this patent is extended or adjusted under 35 U.S.C. 154(b) by 77 days.

(21) Appl. No.: 15/118,767

(22) PCT Filed: Feb. 12, 2015

(86) PCT No.: PCT/EP2015/053026
§ 371 (c)(1),
(2) Date: Aug. 12, 2016

(87) PCT Pub. No.: WO2015/121383
PCT Pub. Date: Aug. 20, 2015

(65) Prior Publication Data
US 2017/0298148 A1 Oct. 19, 2017

Related U.S. Application Data

(60) Provisional application No. 61/938,791, filed on Feb. 12, 2014.

(51) Int. Cl.
*C07K 16/00* (2006.01)
*C07K 16/46* (2006.01)
*C07K 16/28* (2006.01)
*A61K 39/395* (2006.01)
*A61K 45/06* (2006.01)
*A61K 39/00* (2006.01)

(52) U.S. Cl.
CPC ...... *C07K 16/468* (2013.01); *A61K 39/39558* (2013.01); *A61K 45/06* (2013.01); *C07K 16/2803* (2013.01); *C07K 16/2896* (2013.01); *A61K 2039/505* (2013.01); *C07K 2317/31* (2013.01); *C07K 2317/52* (2013.01); *C07K 2317/565* (2013.01); *C07K 2317/567* (2013.01); *C07K 2317/622* (2013.01); *C07K 2317/73* (2013.01)

(58) Field of Classification Search
None
See application file for complete search history.

(56) References Cited

FOREIGN PATENT DOCUMENTS

| EP | 2 769 989 A1 | 8/2014 |
|---|---|---|
| WO | WO 2011/053435 A1 | 5/2011 |

OTHER PUBLICATIONS

Gaziev et al. "Higher CD3+ and CD34+ cell doses in the graft increase the incidence of acute GVHD in children receiving BMT for thalassemia" *Bone Marrow Transplantation* 47:107-114 (2012).
Huang et al. "Cytokine-induced killer (CIK) cells bound with anti-CD3/anti-CD133 bispecific antibodies target $CD133^{high}$ cancer stem cells in vitro and in vivo" *Clinical Immunology* 149:156-168 (2013).
International Search Report and the Written Opinion of the International Searching Authority corresponding to International Patent Application No. PCT/EP2015/053026 (11 pages) (dated Jun. 22, 2015).
Remberger et al. "Effect of Total Nucleated and CD34+ Cell Dose on Outcome after Allogeneic Hematopoietic Stem Cell Transplantation" *Biology of Blood and Marrow Transplantation* 21:889-893 (2015).
Urbano-Ispizua, A. "High stem cell dose in haemopoietic transplantation: is it always beneficial?" *Leukemia* 17:1467-1469 (2003).

*Primary Examiner* — Michail A Belyavskyi
(74) *Attorney, Agent, or Firm* — Myers Bigel, P.A.

(57) ABSTRACT

New monoclonal antibodies for use in pre-treatments prior to stem cell transplantations are disclosed. The antibodies may be used to kill malignant cells and/or stem cells prior to stem cell transplantation. The antibodies can be used for treating hematologic diseases and hematological malignancies, such as leukemia and MDS. The antibodies of the invention might be multi- or bi-specific, such as BiTEs.

2 Claims, 2 Drawing Sheets

Specification includes a Sequence Listing.

BISPECIFIC ANTIBODIES FOR USE IN STEM CELL TRANSPLANTATION

STATEMENT OF PRIORITY

This application is a 35 USC § 371 national phase application of International Application Serial No. PCT/EP2015/053026, filed Feb. 12, 2015, which claims the benefit, under 35 U.S.C. § 119(e), of U.S. Provisional Application Ser. No. 61/938,791, filed Feb. 12, 2014, the entire contents of each of which are incorporated by reference herein.

STATEMENT REGARDING ELECTRONIC FILING OF A SEQUENCE LISTING

A Sequence Listing in ASCII text format, submitted under 37 C.F.R. § 1.821, entitled 9737-47_ST25_2.txt, 67,788 bytes in size, generated on May 8, 2017 and filed via EFS-Web, is provided in lieu of a paper copy. This Sequence Listing is hereby incorporated by reference herein into the specification for its disclosures.

BACKGROUND OF THE INVENTION

Field of the Invention

The present invention relates generally to antibody-based therapy. More specifically the invention relates to bi- or multi-specific antibodies for the pre-treatment of a subject prior to receiving a stem cell transplantation, wherein the subject is suffering from a condition in which a stem cell transplantation is considered to be beneficial for example a hematologic disease or a hematological malignancy, such as myelodysplastic syndrome or leukemia.

Description of the Related Art

Stem cell transplantation, i.e. the transplantation of stem cells to a subject in need thereof, is a common therapy for a number of disorders/conditions with a great potential to cure. However, there are many risks associated with such transplantations, such as e.g. rejection and graft-versus-host disease (GVHD).

Hematologic diseases such as hematological malignancies are cancers/disorders that affect blood, bone marrow and/or lymph nodes. Hematologic diseases primarily derive from either of the two major blood cell lineages: myeloid and lymphoid cell lines. The myeloid cell line normally produces granulocytes, erythrocytes, thrombocytes, macrophages and mast cells; the lymphoid cell line produces B, T, NK and plasma cells. Lymphomas, lymphocytic leukemias, and myeloma are from the lymphoid cell lineage, while acute and chronic myelogenous leukemia, myelodysplastic syndromes and myeloproliferative diseases are myeloid in origin. Aggressive forms of hematologic diseases or hematological malignancies often require treatment with chemotherapy, radiotherapy or immunotherapy, and in some cases a stem cell transplantation, formerly known as a bone marrow transplantation. Common types of hematologic diseases and hematological malignancies are leukemias and lymphomas and myelodysplastic syndromes.

The myelodysplastic syndromes (MDS), formerly known as preleukemia since they might develop into leukemia, are a diverse collection of hematological medical conditions that involve ineffective production (or dysplasia) of the myeloid class of blood cells. The myelodysplastic syndromes are all disorders of the hematopoietic stem cell in the bone marrow. In MDS, hematopoiesis (blood production) is disorderly and ineffective. The number and quality of blood-forming cells decline irreversibly in MDS, further impairing blood production. Patients with MDS can develop severe anemia and require blood transfusions. In some cases, the disease worsens and the patient develops cytopenias (low blood counts) caused by progressive bone marrow failure. MDS is classified by WHO (World Health Organization) into 7 categories; Refractory cytopenia with unilineage dysplasia (RCUD), Refractory anemia with ringed sideroblasts (RARS), Refractory cytopenia with multilineage dysplasia (RCMD), Refractory anemia with excess blasts-1 (RAEB-1), Refractory anemia with excess blasts-2 (RAEB-2), Myelodysplastic syndrome, unclassified (MDS-U), and Myelodysplastic syndrome associated with isolated del (5q). Most of these categories are determined by the appearance of disease related cells in the blood and the bone marrow. One category is defined by a certain chromosome change in the bone marrow cells. Because small differences in the way the cells look can change the diagnosis, physicians may sometimes disagree on the exact MDS category for a patient's disease. The WHO system defines types of MDS based on the cells in the blood and bone marrow. This is called a cellular classification system. Cases of MDS can also be classified based on the underlying cause. This is known as a clinical classification. If no cause can be identified, it is called primary MDS. When the cause of the disease is known, it is called secondary MDS. Secondary MDS is often called treatment-related MDS, because the most common cause is prior cancer treatment. Identifying MDS as primary or secondary is important because the secondary type is much less likely to respond to treatment. The goals of MDS treatment are to control symptoms, improve quality of life, improve overall survival, and decrease progression to acute myelogenous leukemia (AML). Since MDS are stem cell related conditions, stem cell transplantations offer the potential for curative therapy, particularly in more severely affected patients.

Leukemia is a type of cancer of the blood or bone marrow characterized by an abnormal increase of immature white blood cells called blast cells (a partially differentiated precursor cell that has lost most of the stem cell multipotency). Leukemia is a broad term covering a spectrum of diseases and is subdivided into a variety of large groups. The first division is between acute and chronic forms, and the second division according to which kind of blood cell is affected; lymphocytic- or myelogenous leukemia. Thus, the term leukemia includes: acute lymphoblastic leukemia (ALL), acute myelogenous leukemia (AML), acute monocytic leukemia (AMoL), chronic lymphocytic leukemia (CLL), chronic myelogenous leukemia (CML) and other leukemias (such as hairy cell leukemia (HCL), T-cell prolymphocytic leukemia (T-PLL), large granular lymphocytic leukemia and adult T-cell leukemia). Leukemia can affect people at any age, and about 90% of all leukemias are diagnosed in adults. Leukemia is a treatable disease and most treatments involve chemotherapy, medical radiation therapy, hormone treatments, and/or stem cell transplants from bone marrow, peripheral stem cells or umbilical cord blood. The rate of cure depends on the type of leukemia and the age of the patient, with children being more likely to be permanently cured than adults. For many patients, stem cell transplantation is the only option left.

However, current conditioning regimens are often so toxic to the host that they are contraindicated for large groups of patients and/or cannot be provided in sufficient amounts to prevent graft-versus-host disease.

Thus, there is a need for decreasing the risk associated with stem cell transplantation and increasing its effectiveness for various disorders.

SUMMARY OF THE INVENTION

The general purpose of the invention is to provide new antibodies for use in a pre-treatment prior to stem cell transplantation, or after stem cell transplantation prior to a stem cell re-transplantation if relapse of the underlying malignancy occurs. One aspect of the invention is to treat hematologic diseases and hematological malignancies, e.g. by reducing/treating/preventing relapse after stem cell transplantation using said pre-treatment method. Administration of new antibodies, for more efficient killing of malignant cells and/or hematopoietic stem cells before stem cell transplantation, reduces complications and reduces the risk of relapse.

A primary object of the invention is to destroy/kill undesired/malignant cells before stem cell transplantation using monoclonal antibodies, by administering the antibodies to a subject in need thereof suffering from a malignant disease or condition, and who is to undergo a stem cell transplantation, prior to said transplantation. In one aspect of the invention, the transplantation is HSCT. The transplantations could be autologous, allogeneic, syngeneic or xenogeneic. In a further aspect, the antibodies of the invention are multi-specific. In another aspect of the invention, the antibodies are bi-specific. The bi-specific antibodies of the invention might be for example BiTEs, Diabodies, mAB2, Duobodies or any other suitable bi-specific antibody construct known in the art, and may be produced by any known suitable method in the art.

Another object of the invention is a monoclonal antibody directed to a target antigen present specifically on, or a marker for, HSCs, or present on, or a marker for, both a malignant cell, such as cancer cell, and HSC. In one aspect, the target can be CD34. In another aspect, the target can be CD133. In a further aspect, the target further includes, but is not limited to, CD59+, Thy1/CD90+ or C-kit/CD117, which, just as CD34 and CD133, target HSCs but not most other hematopoietic cells since they are present almost solely on stem cells. The multi- or bi-specific antibodies of the invention can be directed against at least one activating molecule on effector cells, e.g. T cells, NK cells or macrophages, and one marker specific for HSCs or shared by both tumor cells and HSCs. The activating molecules can include, but is not limited to, CD3, TCR, CD16, NK receptors that include, but are not limited to, NKG2D, NKp44, NKp46, and/or NKp30, and/or DNAM, and/or other activating molecules. In one aspect, the antibody can be a BiTE targeting CD3 and CD34. In another aspect the antibody can be a BiTE targeting CD3 and CD133.

Another object of the invention are monoclonal antibodies directed to one marker specific for HSC or a marker shared by both tumor cells and HSC, for killing of the recipients own HSCs prior to transplantation, thus minimizing risk for rejection and achieving an indirect immunosuppressive effect. The antibodies can be mono, bi- or multi-specific. In one aspect, the antibodies prevent the risk/occurrence of GVHD.

Another object of the invention is to treat hematologic disorders or hematological malignancies using antibodies directed to targets present on/markers for both undesired/malignant cells and HSCs. In one aspect, a method of treating a hematologic disease or hematological malignancy in a subject can be achieved by administering to a subject in need thereof antibodies directed to targets present on both undesired/malignant/cancer cells and HSC. In one aspect, the hematological malignancy can be leukemia, such as ALL, AML or AMoL. In another aspect the hematologic disease can be MDS. In a further aspect the disease/malignancy can be any disorder or condition requiring or benefitting from stem cell transplantation, such as CML, CLL, other leukemias and lymphoma. A further object of the invention can be the treatment of relapse after HSCT of the underlying malignancy, in particular ALL, AML and MDS.

One object of the invention is to treat hematological disorders and/or malignancies, such as ALL, AML, AMoL or MDS, requiring a stem cell transplantation, such as a allogeneic HSCT, by destroying undesired/malignant cells prior to transplantation using monoclonal bi-specific or multi-specific antibodies, such as BiTEs, directed to targets present on both stem cells and undesired/malignant/cancer cells, including, but not limited to, CD34 or CD133. In one aspect, MDS can be treated using a BiTE targeting CD3 and CD34, or CD3 and CD133. In another aspect ALL can be treated using a BiTE targeting CD3 and CD34, or CD3 and CD133. In another aspect AML can treated using a BiTE targeting CD3 and CD34, or CD3 and CD133.

Another object of the invention is a method for treatment of a subject in need thereof prior to receiving stem cell transplantation, wherein the one or more antibodies of the invention are administered to said subject before the transplantation. In one aspect of the invention, a new stem cell transplantation pre-treatment method fewer and/or less pronounced side effects compared to existing pre-treatment methods is attained by administering the antibodies of the invention to a subject eligible for stem cell transplantation prior to said transplantation. One aspect of the invention is the use of the antibodies of the invention as a pre-treatment prior to stem cell transplantation, wherein the antibodies are administered in an effective amount to a subject about to undergo a stem cell transplantation prior to said stem transplantation.

The improved method for destroying undesired cells, such as malignant cells or the subject's own HSCs, before transplantation could be used for any subject or patient about to undergo stem cell transplantation, such as HSCT, due to a malignant disease or any other cause, either prior to a first transplantation, or prior to a re-transplantation, e.g. after a relapse.

Other objects and advantages of the present invention will become obvious to the reader. For the avoidance of doubt, the description of a feature as an 'object' of the invention does not necessarily imply that the object is achieved by all embodiments of the invention. Also, it is to be understood that the phraseology and terminology employed herein are for the purpose of the description and should not necessarily be regarded as limiting.

BRIEF DESCRIPTION OF THE DRAWINGS

FIG. 1A. Graphs represents frequencies of 7AAD+ cells (necrotic) gated from lymphocytes/CD3+/CD34+ cells. Y-axis side scatter and X-axis 7AAD intensity. Upper left graph shows the background of dead cells (7AAD+) after overnight culture. The three lower lines represents cells incubated with CD34/(−), CD3/(−) and CD34/CD3 respectively in the increasing concentrations, 0.1, 1.0 and 10 ug/ml. FIG. 1B Graphs represent frequencies of 7AAD+ cells (necrotic) gated from lymphocytes/CD3−/CD19+ cells and lymphocytes/CD3−/CD56+ representivaly. The Cells where treated with increasing concentrations, 0.1, 1.0 and 10 ug/ml of CD34/CD3 bispecific antibodies.

DETAILED DESCRIPTION OF THE INVENTION

Figure 1:
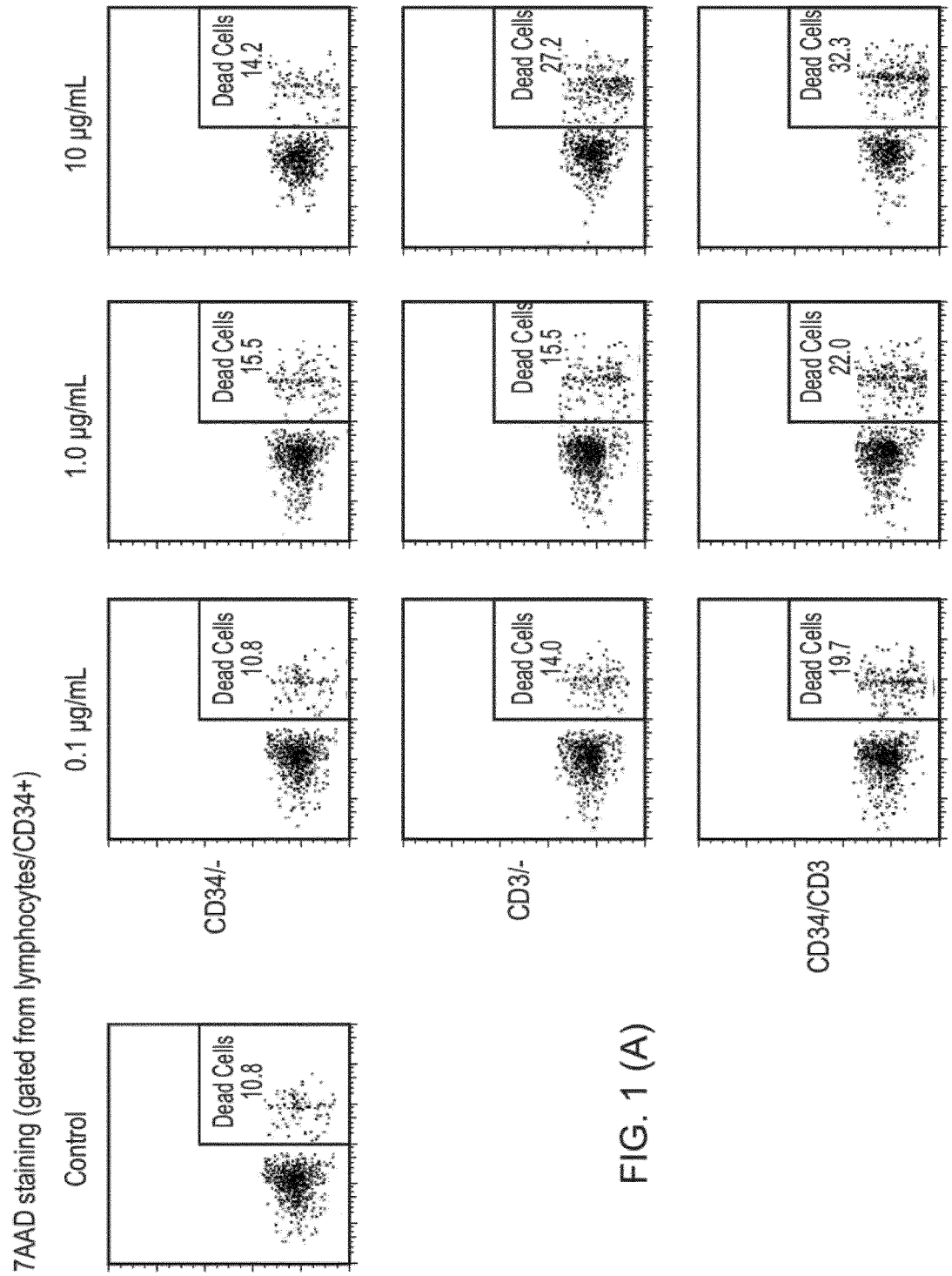
FIGS. 1A and 1B: CD34/CD3 bispecific antibodies selectively kill CD34+ hematopoetic stem cells in a dose-dependent manner.
Figure 1:
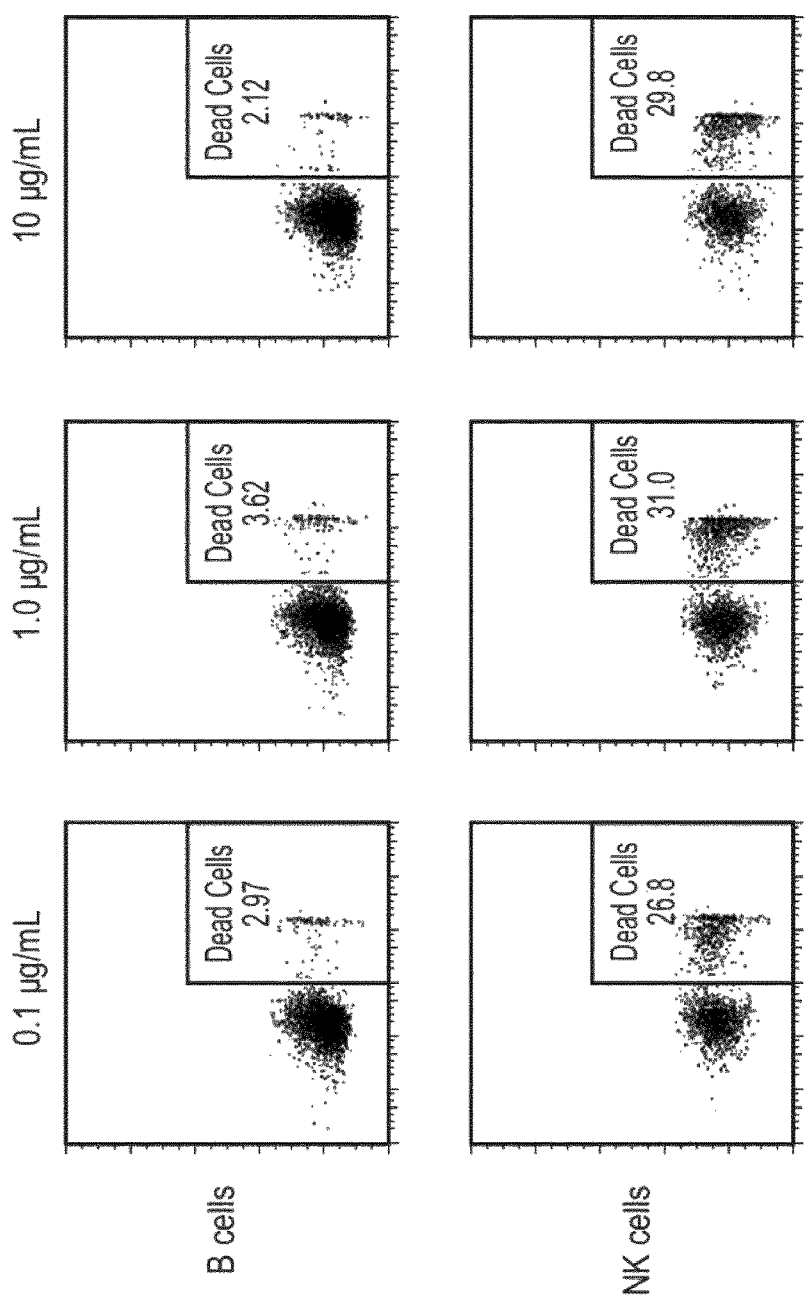

The present invention now will be described hereinafter with reference to the accompanying drawings and examples, in which embodiments of the invention are shown. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments and is not necessarily intended to be limiting of the invention.

All publications, patent applications, patents and other references cited herein are incorporated by reference in their entireties for the teachings relevant to the sentence and/or paragraph in which the reference is presented.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

As used in the description of the invention and the appended claims, the singular forms "a," "an" and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

The term "about," as used herein when referring to a measurable value such as a dosage or time period and the like refers to variations of ±20%, ±10%, ±5%, ±1%, ±0.5%, or even ±0.1% of the specified amount.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

As used herein, the terms "increase," "increasing," "increased," "enhance," "enhanced," "enhancing," and "enhancement" (and grammatical variations thereof) describe an elevation of at least about 25%, 50%, 75%, 100%, 150%, 200%, 300%, 400%, 500% or more as compared to a control.

As used herein, the terms "reduce," "reduced," "reducing," "reduction," "diminish," "suppress," and "decrease" (and grammatical variations thereof), describe, for example, a decrease of at least about 5%, 10%, 15%, 20%, 25%, 35%, 50%, 75%, 80%, 85%, 90%, 95%, 97%, 98%, 99%, or 100% as compared to a control. In particular embodiments, the reduction results in no or essentially no (i.e., an insignificant amount, e.g., less than about 10% or even 5%) detectable activity or amount. Thus, in some embodiments, treatment of a patient in need thereof with the antibodies of the present invention results in a reduction or decrease in side effects by at least about 5%, 10%, 15%, 20%, 25%, 35%, 50%, 75%, 80%, 85%, 90%, 95%, 97%, 98%, 99%, or 100% as compared to a control (e.g., a patient administered conventional antibodies).

The present invention relates to antibodies (e.g., monoclonal antibodies) for use in a pre-treatment method for a subject about to undergo stem cell transplantation. The antibodies of the invention can be used as a pre-treatment before stem cell transplantation, and/or prior to a re-transplantation if relapse of the underlying malignancy occurs, regardless of the reason for the transplantation, and pretreatment of a patient using the antibodies of this invention will give rise to less side effects such as GVHD, drug-induced toxicities and infections when compared to other existing pre-treatment methods. If the reason for the transplantation is a hematological malignancy, the monoclonal antibodies of the invention can also be used for the treatment of said hematological malignancy, reducing relapse after stem cell transplantation due to more efficient killing of malignant cells before the transplantation, also having an additional beneficial effect of reduced impact on the recipient's immune cells/stem cells.

Thus, an object of the invention is the use of new antibodies as a pre-treatment prior to stem cell transplantation, for minimizing the risk and occurrence of rejection and GVHD. Another object of the invention is the use of said antibodies as a pre-treatment prior to stem cell transplantation or re-transplantation wherein the subject is suffering from a hematologic disease or hematological malignancy, for treating said hematologic disease or hematological malignancy, reducing the risk of relapse as well as minimizing the risk and occurrence of rejection and GVHD. A further object of the invention is the treatment of relapse after HSCT of the underlying malignancies.

The most common type of transplantation in hematologic/leukemic diseases is the transplantation of hematopoietic stem cells (HSCs) derived usually from bone marrow, peripheral blood, or umbilical cord blood. HSCs are the cells that give rise to all blood cells; the myeloid (monocytes and macrophages, neutrophils, basophils, eosinophils, erythrocytes, megakaryocytes/platelets, dendritic cells), and lymphoid lineages (T-cells, B-cells, NK-cells). Many of the markers present on HSCs belong to the cluster of differentiation series, like: CD34, CD38, CD90, CD133, CD105, CD45. Two of the most common markers used for identifying/targeting HSCs are CD34 and CD133. Other suitable markers include Thy1/CD90+ and C-kit/CD117. As stem cells, HSCs are defined by their ability to replenish all blood cell types (multipotency) and their ability to self-renew. It is known that a small number of HSCs can expand to generate a very large number of daughter HSCs. This phenomenon is used in hematopoietic stem cell transplantation (HSCT), when a relatively small number of HSCs reconstitute the hematopoietic system. This process indicates that, subsequent to HSCT, symmetrical cell divisions into two daughter HSCs must occur. The HSCT are either allogeneic (from another individual), or autologous (from the same individual). Before the transplantation takes place, the recipient's immune system is usually destroyed with radiation or chemotherapy with the intention of eradicating the patient's malignant cell population and decrease the risk of rejection of the new immune HSCs at the cost of partial or complete bone marrow ablation (destruction of patient's bone marrow function to grow new blood cells). The stem cells to be transplanted are then transfused into the recipient patient's bloodstream where enough numbers quickly find the way to the bone marrow space, where they replace the damaged hematopoietic system and resume the patient's normal blood cell production. Allogeneic HSCT is a procedure associated with many potential complications, such as infection and graft-versus-host disease, but as the treatment modality has improved and survival increased, its use has expanded beyond cancer, such as inborn errors of metabolism and autoimmune diseases.

Prognosis in HSCT varies widely dependent upon disease type, stage, stem cell source, HLA-matched status (for allogeneic HCST) and conditioning regimen. A transplant offers a chance for cure or long-term remission if complications, such as graft versus host disease (GVHD), and the spectrum of opportunistic infections can be surmounted. However, even if the procedure is successful, some patients suffer from cancer relapse due to incomplete elimination of the patient's malignant cell population before and after transplantation. Accordingly, a new improved method for stem cell transplantation pre-treatment is therefore desired, which minimizes the risks and complications associated with regular pre-treatments and which offers more efficient killing of malignant cells before transplantation. Thus, provided herein is a new antibody-based immunotherapy pre-treatment method, which decreases risks and complications associated with stem cell transplantations, and which may be used for treating hematologic diseases and hematological malignancies, such as leukemia or MDS, by efficient killing malignant cells prior to HSCT. The immunotherapy also works as an indirect immunosuppressive treatment prior to transplantation and reduces the risk of rejection, due to striking the recipients HSCs that produce new immune cells, which may attack new transplanted donor cells. Further, it can also limit the occurrence of GVHD after transplantation by reducing the amount of radiation therapy and/or chemotherapy needed, since the use of these therapies may induce GVHD. In a particular embodiment, the pre-treatment is carried out before a re-transplantation after a relapse from a first HSCT, as a therapy for the underlying disorders or malignancies before said re-transplantation.

Monoclonal antibody therapy is the use of monoclonal antibodies to specifically bind to target cells or proteins. This may then stimulate the patient's immune system to attack those cells. It is possible to create a monoclonal antibody specific to almost any extracellular/cell surface target, and thus there is a large amount of research and development currently being undertaken to create monoclonals for numerous serious diseases such as rheumatoid arthritis, multiple sclerosis, Alzheimer's disease and different types of cancers. There are a number of ways that monoclonal antibodies can be used for therapy, for example in cancer therapy to destroy malignant tumor cells and prevent tumor growth by blocking specific cell receptors.

Cancer immunotherapy is the use of the immune system to reject cancer. The main premise is stimulating the patient's immune system to attack the malignant tumor cells that are responsible for the disease. This can be either through immunization of the patient, in which the patient's own immune system is trained to recognize tumor cells as targets to be destroyed, or through the administration of therapeutic antibodies as drugs, in which the patient's immune system is recruited to destroy tumor cells by the therapeutic antibodies, or by cell based immunotherapy involving immune cells, which are activated or isolated, enriched and transfused to the patient to fight cancer. The field of antibody-based cancer immunotherapy has expanded rapidly in the last years, wherein monoclonal antibodies are directed to a target on a cancer cell; usually an antigen or a receptor site on the cancer cell, or it is directed at a cancer specific enzyme or protein. Many clinically useful antibodies can manipulate tumor-related signaling, and in addition exhibit various immunomodulatory properties, such as promoting the induction of antitumor immune responses, by directly activating or inhibiting molecules of the immune system. There are many mechanisms of action for anti-carcinogenic monoclonal antibodies, such as making the cancer cell more visible to the immune system, block growth signals and inhibit angiogenesis.

Most of the marketed monoclonal antibodies used in cancer immunotherapy are mono-specific antibodies i.e. directed to a single target. However, complex diseases are often multifactorial in nature, and involve redundant or synergistic action of disease mediators or up-regulation of different receptors, including crosstalk between their signaling networks. Consequently, a blockade of multiple, different pathological factors and pathways may result in improved therapeutic efficacy. This can be achieved by using multi-specific monoclonal antibodies, such as bi-specific antibodies with dual targeting, wherein for example the antibodies are engineered to simultaneously bind to a cytotoxic cell and a target cell, like a tumor cell, to be destroyed.

Accordingly, described herein is a new antibody-based immunotherapy for destroying/killing/reducing malignant cells, such as tumor cells and cancer stem cells, and/or hematopoietic stem cells prior to a first HSCT or a HSC re-transplantation in patients with relapse after HSCT. This antibody-based immunotherapy targets, for example, markers specific for HSCs and/or markers expressed on cancer cells that are shared with HSCs, i.e. markers present on both cancer cells and HSCs, including, but not limited to, CD34 or CD133. The antibodies (e.g., monoclonal antibodies) directed to specific HSC target antigens can be used to attack the treated subject's HSCs as a pre-treatment prior to HSCT, and allow the patient's immune system to be exchanged for healthy HSCs and immune cells after transplantation. When administered to a subject suffering from cancer, the monoclonal antibodies can both directly attack cancer cells and HSCs expressing the marker antigens. This approach can kill the malignant cells expressing these marker antigens, including tumor cells as well as cancer stem cells (CSCs), but can also kill healthy stem cells. To address this problem, the monoclonal antibody treatment of this invention can be combined with autologous, or in particular, allogeneic stem cell transplantation. However, the efficient killing of healthy HSCs before transplantation can have beneficial aspects, such as an indirect immunosuppressive action to make room for the new immune system and HSCs, reducing the risk for a rejection and reducing the risk of GVHD. Directly targeting HSCs might also be a milder pre-treatment than existing variants enabling HSCT for older and more fragile patients.

The antibodies of the invention can be mono-specific antibodies, but more preferably the antibodies are multi-specific, such as bi-specific antibodies directed to a specific HSC marker antigen or a shared tumor/HSC marker antigen, and an activating molecule present on effector cells, such as T cells, NK cells or macrophages. An activating molecule can include, but is not limited to, CD3, TCR, CD16, or NK receptors that include, but are not limited to, NKG2D, NKp44, NKp46, and/or NKp30, and/or DNAM, and/or other activating molecules.

There are many types and ways to manufacture multi- and bi-specific monoclonal antibodies, one of the most promising formats being a bi-specific T cell engager (BiTE). BiTEs are fusion proteins consisting of two single-chain variable fragments (scFvs) of different antibodies, or amino acid sequences from four different genes, on a single peptide chain of about 55 kilo Daltons. One of the scFvs binds to T cells via the CD3 receptor, and the other to a tumor cell via a tumor specific molecule, and their action mimics the physiological processes observed during T-cell attacks against tumor cells. The BiTEs form a link between T-cells and tumor cells causing T-cells to exert cytotoxic activity on tumor cells and initiate the apoptosis of the target cell. In one embodiment of the invention, the antibody can be a BiTE directed against CD3 and CD34. In a further embodiment, the BiTE can be directed against CD3 and CD133. In a further embodiment, the BiTE can be directed against CD3 and Thy1/CD90$^+$. In a further embodiment, the BiTE can be directed against CD3 and C-kit/CD117. The BiTEs, or other bi-specific or multi-specific antibodies of the invention, can be directed to an activating molecule and a marker shared by cancer cells and HSCs (and optionally one or more additional markers) when the subject is suffering from cancer. Alternatively, the BiTEs can be directed to an activating molecule and a specific HSC marker (and optionally one or more additional markers) when the subject is suffering from a condition other than cancer.

Thus, the current invention discloses multi-specific, such as bi-specific, antibodies directed against at least one activating molecule on effector cells, and/or against at least one marker specific for HSCs, for use in the pre-treatment prior to stem cell transplantation, and/or after a stem cell transplantation prior to a re-transplantation. When the subject to be treated suffers from a cancer, the antibodies can be directed to at least one activating molecule on effector cells, and/or against at least one marker shared in cancer cells and HSCs. The marker expressed on the tumor cells can/shall be shared with hematopoietic stem cells but not with most other hematopoietic cells, said marker including, but not limited to, CD34 or CD133. Treating cancer patients with these antibodies will result in the antibodies directly attacking the tumor cells expressing these markers as well as the patient's hematopoietic stem cells. As a consequence, the patient may suffer from leukopenia and erytrophenia, and therefore may be in need of either autologous, or in particular, allogeneic hematopoietic stem cell transplantation. The treatment of this invention can therefore be used as a pre-treatment before stem cell transplantation, and/or after (prior to a re-transplantation) if relapse of the underlying malignancy occurs. Treatment of a patient with the multi-specific/bi-specific antibody of this invention can be carried out either prior to transplantation, in a preconditioning regimen, then used as a chemotherapeutic agent to kill of malignant clones to make patients ready for stem cell transplantation. Alternatively, patients that relapse in their underlying malignant disease after stem cell transplantation can be treated with this invention in order to make them eligible for a re-transplantation.

The antibodies of the invention could be multi-specific, targeting one or more (e.g., 2, 3, 4, 5, or more, and the like) markers present specifically on HSCs or markers shared by cancer cells and HSCs and/or one or several effector cell activating molecules. In one embodiment, the specific HSC marker can be CD34 and/or CD133. In another embodiment the marker shared by HSCs and cancer cells can be CD34 and/or CD133. In one embodiment of the invention, the antibody can be a bi-specific antibody directed to CD34 and/or CD133 and an effector cell-activating molecule. In a particular embodiment, the antibody can be a bi-specific BiTE directed to CD3 and CD34. In a further embodiment, the antibody can be a bi-specific BiTE directed to CD3 and CD133. BiTEs like these could be used to directly target tumor cells and cancer stem cells. While the CD34 and/or CD133 molecules are also expressed on healthy hematopoietic stem cells, the treatment with a BiTE targeting CD3 and CD34 or CD3 and CD133 can be combined with autologous or in particular allogeneic hematopoietic stem cell transplantation to address the effects resulting from the possible targeting of the patient's healthy hematopoietic stem cells. The antibodies/BiTEs of the invention can thus be used as a pre-treatment prior to HSCT. In an allogeneic HSCT the patient's own HSCs and immune system is exchanged for HSCs and white blood cells from a healthy individual. When the new HSCs are infused, the effect of the antibody/BiTE (on for example CD34 expressing cells) is already over, since the antibody has a finite half-life and has cleared out before infusion of new stem cells. The end result is that malignant cells expressing CD34 are gone and a new healthy immune and hematopoietic system can repopulate the patient. Also healthy cells expressing CD34 can be targeted, giving rise to an indirect immunosuppressive effect and reducing the risk of GVHD, in particular since less chemotherapy during preparatory treatment before HSCT will be needed.

To our knowledge no one has created bi-specific antibodies with one of the two specificities against the molecules CD34 or CD133, such as BiTEs with the dual specificity for CD34 or CD133, which are expressed on hematopoietic stem cells (HSCs), and CD3 expressed on T cells, or used said antibodies in a pre-treatment prior to stem cell transplantation or re-transplantation.

There are several BiTEs in clinical trials today, such as Blinatumomab directed towards CD19 (a surface molecule expressed on B-cells) for the treatment of non-Hodgkin's lymphoma and ALL. For example, patent application US2011262440 relates to such BiTEs for treating pediatric acute lymphoblastic leukemia. These may be used either prior or after stem cell transplantation to convert the MRD positive ALL into an MRD negative status. Since antibodies directed against CD19 targets more differentiated cells than the antibodies of the invention, using such an antibody as a pre-treatment prior to stem cell transplantation could induce a much harsher reaction than the antibodies of the invention, and one of the major reasons for using the new antibodies of the invention instead of commonly used pre-treatment is to get a milder pre-treatment with less side-effects. Further, in the case of treating a subject suffering from cancer, the beneficial effect of killing CSCs will not be achieved using the CD19 specific BiTE. Also the prolonged indirect immunosuppressive effect obtained by killing the recipient's own HSCs before transplantation would not be attained. The CD19 antibody targets the B-cells and not the HSCs, and could therefore not be used in a pre-treatment prior to HSCT wherein the HSCs need to be targeted or for treatment of malignancies/disorders such as T-ALL, AML or MDS. The CD19 specific BiTE would therefore not be suitable as an alternative to the antibodies of the invention for use as a pre-treatment prior to stem cell transplantation.

The paper of C Arndt et al. ("Redirection of T cells with a first fully humanized bi-specific CD33-CD3 antibody efficiently eliminates AML blasts without harming hematopoietic stem cells"; *Leukemia* 2013, 27: 964-967) describes a BiTE directed towards CD33, for the treatment of AML. CD33 is a transmembrane receptor expressed on cells of myeloid lineage (granulocyte precursor cells in bone marrow or spinal cord), and is considered to be myeloid-specific but can also be found on some lymphoid cells. CD33 has been the target for a mono-specific monoclonal antibody for the treatment of AML, but has been withdrawn from the market. Since CD33 is expressed on almost all cells of myeloid lineage it too, will have the same drawbacks as the CD19 BiTE discussed above. It will give rise to more side effects and will not target the CSCs or the HSCs, or give the indirect immunosuppressive effect obtained by the antibodies of the invention. Due to this a CD33/CD3 directed BiTE cannot be used efficiently in a pre-conditioning regimen prior to HSCT. Further, according to Arndt et al. an important aspect of the CD33/CD3 BiTE is that it does not affect CD34+ HSCPs, which would lead the person skilled in the art reading this paper away from the current invention.

To directly kill stem cells (HSCs) BiTEs directed against CD45 and myosin light chain has been tried in in vitro models in the paper of C Zhao T C et al. ("Targeting human CD34+ hematopoietic stem cells with anti-CD45 x anti-myosin light-chain bi-specific antibody preserves cardiac function in myocardial infarction"; *J Appl Physiol* 2008, 104(6): 1793-1800). CD45 is a type I transmembrane protein that is in various forms present on all differentiated hematopoietic cells except erythrocytes and plasma cells, and CD45 assists in the regulation of those cells. It is expressed in lymphomas, B-cell chronic lymphocytic leukemia, hairy cell leukemia, and acute nonlymphocytic leukemia. CD45 is expressed on HSCs in different isoforms during development, e.g. CD45YA, CD45RB and CD45RO, however since it is also expressed on all other cells in the hematopoietic system, such as B-cell, T-cells and macrophages, a treatment with a BiTE directed against CD3 and CD45 would induce such a massive reaction that the patient most likely would not survive the treatment.

The antibodies of the present invention should be directed to markers specific for HSCs or shared by HSCs and malignant cells, but not shared by most other hematopoietic cells, such as less than half, to avoid a too harsh reaction. Accordingly, since the reaction would most probably be life threatening, a CD45 specific BiTE should not be used as a pre-treatment before stem cell transplantation, as the antibodies of the present invention.

Thus, for the first time is presented bi- or multi-specific antibodies directed against HSCs for use in pre-treatment prior to HSCT, a first HSCT or a HSC re-transplantation, targeting CD34, CD133, Thy1/CD90$^+$ and/or C-kit/CD117 [or combinations of bi-specific antibodies].

The bone marrow produces white blood cells that build up our immune system, red blood cells that carry oxygen to all body cells and platelets that enable the blood to efficiently clot. Hematopoietic stem cell transplantation (HSCT), or bone marrow transplantation which it was called earlier, is nowadays an established treatment for a range of diseases that affect the body's blood stem cells such as leukemia, severe anemia, immune defects, and some more unusual enzyme deficiency diseases. These illnesses often lead to the patient needing to have his bone marrow replaced by new, healthy blood cells.

HSCT is often allogeneic stem cell transplantation, which means that the patient receives stem cells from another individual of the same species, either a sibling, matched related, haploidentical related or unrelated, volunteer donor. Today, it is estimated that about 30% of patients in need of HSCT have access to a sibling whose tissue type is suitable. The other 70 percent must rely on the matching of an unrelated, volunteer donor or the availability of a haploidentical, related donor. Today, there are more than 20 million volunteer donors in registries around the world. It is important that donor and patient cell characteristics are comparable. On the surface of a person's cells are tissue markers that are specific for each individual. These are called MHC molecules (HLA in humans) and help the white blood cells to recognize what is "own" and "non-own". Cells with "foreign" (non-own) MHC are perceived as alien and are killed. The HSCT could also be autologous, in which the transplanted cells are originating from the subject itself, i.e. the donor and the recipient are the same individual. Further, the transplantations could be syngeneic, i.e. from a genetically identical individual such as a twin, or in an additional aspect the transplantations could be xenogneic, i.e. originating from a different species, which is particularly interesting when lacking donors, such as for organ transplantations.

Before the transplant, patients undergo a pre-treatment, in which they are often treated with chemotherapy and/or radiation. The purpose of this pre-treatment is to remove as many undesired/malignant/cancer cells in the body as possible and/or to remove the patient's own immune system so that the new, healthy marrow is not rejected. Donor's healthy stem cells are then given to the patient intravenously, or in some cases intraosseously. Although the donor and the patient's cells appear to be equal in terms of tissue type, i.e. the MHC molecules are matched (or haploidentical); there are still minor differences between these individuals that immune cells can perceive as dangerous. This means that the new immune system (white blood cells from the new stem cells) perceive the new body as "foreign", which provokes an immune attack. This reaction, called graft-versus-host disease (GVHD), affects primarily the remaining blood cells from the patient's "old" marrow and kills them. The type of white blood cell that is responsible for this attack (which also affects the cancer cells) is called a T cell. A GVHD reaction can also affect other body parts and if the reaction becomes excessive it can become life-threatening to the patient. In more severe GVHD, there is no effective treatment today. It is also well known that it is easier to prevent than treat GVHD. It is therefore of great importance to develop new methods to prevent the occurrence of GVHD.

All patients after HSCT have an increased risk of infections due to absence of white blood cells before the new marrow begins to function. This period can in some cases last for many months until the new immune system have matured. Some of these opportunistic infections after HSCT may be life-threatening. However, the most common life-threatening complication in patients with malignant disease after HSCT is relapse. Today, we have developed methods for early detection of patients that are at increased risk of relapse. In these patients, the anti-cancer effect after HSCT can be enhanced by additional new immune cells from the original donor. However, this is also associated with an increased risk of severe GVHD. In addition, cancer cells have developed several ways to avoid being attacked. The most serious complications after HSCT are therefore GVHD, infections and relapse of the malignancy.

Thus, an improved pre-treatment method before stem cell transplantation, which reduces the risk of infections, rejection, GVHD and other side effects by harsh pre-treatment methods in the art and, when the subject is suffering from a malignant disease, increases the destruction/killing of malignant cells, is desired. Herein, is therefore provided new antibodies that, by killing the recipients HSCs prior to transplantation but not all other immune cells, keep a partly active immune defense to combat infections right after transplantation, but at the same time provide an indirect immunosuppressive effect due to the subject's inability to form new immune cells from its own HSCs. Since the pre-treatment is milder, and with less serious side effects, it induces less GVHD. When the stem cell transplant is given to a cancer patient, the antibodies of the invention attack the cancer cells, both the tumor cells and the often missed cancer stem cells, thus reducing the risk of relapse. Accordingly, herein is presented new antibodies, and a new pre-treatment method prior to stem cell transplantation using these antibodies, which minimize side effects seen in other pre-treatments and also efficiently kills undesired/malignant/cancer cells.

A primary object of the invention is to destroy/kill undesired cells, including, but not limited to, malignant cells and/or hematopoietic stem cells, before transplantation or after (before re-transplantation) if relapse of the underlying malignancy occurs, using one or more monoclonal antibodies of the present invention. In one aspect of the invention, the transplantation is an allogeneic transplantation. In another aspect, the transplantation is an autologous transplantation. In a particular aspect, the transplantation is hematopoietic stem cell transplantation (HSCT).

The antibodies of the invention could be used in a pre-treatment before HSCT, independent of the reason for the subject to undergo HSCT. For example, the antibodies of the invention could be used to treat any non-malignant condition/disorder wherein stem cell transplantation could be beneficial, such as Severe aplastic anemia (SAA), Wiskott Aldrich Syndrome, Hurlers Syndrome, FHL, CGD, Kostmanns syndrome, Severe immunodeficiency syndrome (SCID), other autoimmune disorders such as SLE, Multiple sclerosis, IBD, Crohns Disease, Ulcerative colitis, Sjögrens syndrome, vasculitis, Lupus, Myasthenia Gravis, Wegeners disease, inborn errors of metabolism and/or other immunodeficiencies. Further, the antibodies of the invention could be used to treat any disorder/malignancy wherein stem cell transplantation could be beneficial, such as hematologic diseases, hematological malignancies or solid tumors. Common types of hematological diseases/malignancies that could be treated with the claimed methods and antibodies are leukemias, lymphomas and myelodysplastic syndromes. Leukemia is a type of cancer of the blood or bone marrow characterized by an abnormal increase of immature white blood cells called blast cells, and the term leukemia includes; acute lymphoblastic leukemia (ALL), acute myelogenous leukemia (AML), acute monocytic leukemia (AMoL), chronic lymphocytic leukemia (CLL), chronic myelogenous leukemia (CML) and other leukemias (such as hairy cell leukemia (HCL), T-cell prolymphocytic leukemia (T-PLL), large granular lymphocytic leukemia and adult T-cell leukemia). In one aspect of the invention, the leukemia treated is acute leukemia. In a further aspect, the leukemia is ALL, AML or AMoL. Myelodysplastic syndrome (MDS) is the name of a group of conditions that occur when the blood-forming cells in the bone marrow are damaged. This damage leads to low numbers of one or more type of blood cells. MDS is subdivided into 7 categories; Refractory cytopenia with unilineage dysplasia (RCUD), Refractory anemia with ringed sideroblasts (RARS), Refractory cytopenia with multilineage dysplasia (RCMD), Refractory anemia with excess blasts-1 (RAEB-1), Refractory anemia with excess blasts-2 (RAEB-2), Myelodysplastic syndrome, unclassified (MDS-U), and Myelodysplastic syndrome associated with isolated del (5q).

The antibodies of the invention are directed to specific HSC markers/marker antigens or, when treating a malignant disease, to markers/marker antigens for both stem cells and malignant cells, such as cancer cells, wherein the cancer cells targeted are both tumor cells and cancer stem cells. The markers of the invention are specific for HSCs or those shared in stem cells and cancer cells, and are generally not present on other cells since this can lead to a massive immune reaction, which might result in death of the subject treated. Thus a common trait for the markers used in the invention is that they almost solely are expressed on stem cells, and not expressed, or expressed very little, on more mature healthy cells in the hematopoietic system. Suitable such markers include, but are not limited, CD34, CD133, $CD59^+$, $Thy1/CD90^+$ $C-kit/CD117$ and any combination thereof.

The antibodies of the invention could be monoclonal antibodies with a mono specificity for a specific HSC marker or a stem cell marker shared with a malignant cell, such as a cancer cell, as described above. However, in a particular embodiment the antibodies are multi-specific, such as bi-specific, trispecific or tetraspecific, with at least one specificity directed to a marker present on stem cells and/or shared in stem cells and malignant cells. In one embodiment, the multi-specific antibodies are directed to at least one marker present on stem cells and malignant cells and at least one activating molecule present on effector cells that include, but are not limited to, T cells, NK cells and/or macrophages. Targeting activating molecules can enhance the response of an antibody in an effector cell, thus rendering the antibody treatment more effective. The activating molecules of the invention can be, for example, CD3, TCR, CD16, or NK receptors such as NKG2D, NKp44, NKp46, NKp30, and DNAM, or other activating molecules. In one aspect of the invention, an antibody can be a bi-specific antibody directed to CD34 and to an activating molecule, such as CD3, TCR or CD16. In another aspect of the invention, an antibody can be a bi-specific antibody directed to CD133 and to an activating molecule, such as CD3, TCR, CD16, and/or NK receptors such as NKG2D, NKp44, NKp46, NKp30, and/or DNAM and/or other activating molecules.

In a particular embodiment, the antibodies of the invention are bi-specific antibodies directed to one specific HSC marker or a marker shared in HSCs and malignant cells, and one activating molecule. In order to overcome manufacturing difficulties, a first-generation bi-specific monoclonal antibody, called trifunctional antibody, have been developed in the art. The antibody consists of two heavy and two light chains, one each from two different antibodies. The two Fab regions (antibody binding fragment arms) are directed against two antigens. The Fc region (the cell binding fragment foot) is made up from the two heavy chains and forms the third binding site; hence the name. Other types of bi-specific antibodies have been designed, they include chemically linked Fabs, consisting only of the Fab regions, and various types of bivalent and trivalent single-chain variable fragments (scFvs), fusion proteins mimicking the variable domains of two antibodies. The furthest developed of these newer formats are the bi-specific T-cell engagers (BiTEs) and mAb2's, antibodies engineered to contain an Fcab antigen-binding fragment instead of the Fc constant region. In a bi-specific antibody one of the two paratopes (that form the tops of the variable domains) can be directed against a tumor antigen and the other against a T-lymphocyte antigen like CD3. In the case of trifunctional antibodies, the Fc region additionally binds to a cell that expresses Fc receptors, like a macrophage, a natural killer cell or a dendritic cell. In sum, the tumor cell is connected to one or two cells of the immune system, which subsequently destroy it.

Bi-specific antibodies hold advantages over ordinary mono-specific antibodies. Cancer immunotherapy with ordinary monoclonal antibodies does not activate T-lymphocytes because this type of cell does not generally possess Fc receptors, so the Fc region cannot bind to them, and the Fab regions are already used for binding the tumor cells. Bi-specific antibodies have a higher cytotoxic potential. They bind to antigens that are expressed relatively weakly. The effective dose is around 0.01 milligrams per square meter body surface area per day, several orders of magnitude lower than for ordinary antibodies.

The bi-specific antibodies of the invention might be for example BiTEs, Diabodies, mAB2, Duobodies or any other suitable bi-specific antibody construct known in the art. Examples of different classes of bi-specific antibodies include but are not limited to i) IgG-like molecules with complementary CH3 domains to force heterodimerisation, e.g. Triomab/Quadroma (Trion Pharma/Fresenius Biotech), the Knobs-into-Holes (Genentech), CrossMAbs (Roche) and the electrostatically-matched (Amgen), the LUZ-Y (Genentech), the Strand Exchange Engineered Domain body (SEEDbody)(EMD Serono), the Biclonic (Merus) and the DuoBody (Genmab A/S), ii) recombinant IgG-like dual targeting molecules, wherein the two sides of the molecule each contain the Fab fragment or part of the Fab fragment of at least two different antibodies, e.g. Dual Targeting (DT)-Ig (GSK/Domantis), Two-in-one Antibody (Genentech), Cross-linked Mabs (Karmanos Cancer Center), mAb2 (F-Star) and CovX-body (CovX/Pfizer), iii) IgG fusion molecules, wherein full length IgG antibodies are fused to extra Fab fragment or parts of Fab fragment, e.g. Dual Variable Domain (DVD)-Ig (Abbott), IgG-like Bi-specific (ImClone/Eli Lilly), Ts2Ab (MedImmune/AZ) and BsAb (Zymogenetics), HERCULES (Biogen Idec) and TvAb (Roche) iv) Fc fusion molecules, wherein single chain Fv molecules or stabilized diabodies are fused to heavy-chain constant-domains, Fc-regions or parts thereof, e.g. ScFv/Fc Fusions (Academic Institution), SCORPION (Emergent BioSolutions/Trubion, Zymogenetics/BMS), Dual Affinity Retargeting Technology (Fc-DART) (MacroGenics) and Dual(ScFv)2-Fab (National Research Center for Antibody Medicine—China), v) Fab fusion molecules, wherein different Fab-fragments are fused together, e.g. F(ab)2 (Medarex/AMGEN), Dual-Action or Bis-Fab (Genentech), Dock-and-Lock (DNL) (ImmunoMedics), Bivalent Bi-specific (Biotecnol) and Fab-Fv (UCB-Celltech), vi) ScFv- and diabody-based and heavy chain antibodies (e.g., domain antibodies, nanobodies) wherein different single chain Fv molecules or different diabodies or different heavy-chain antibodies (e.g. domain antibodies, nanobodies) are fused to each other or to another protein or carrier molecule, e.g. Bi-specific T Cell Engager (BiTE) (Micromet, Tandem Diabody (Tandab) (Affimed), Dual Affinity Retargeting Technology (DART) (MacroGenics), Single-chain Diabody (Academic), TCR-like Antibodies (AIT, ReceptorLogics), Human Serum Albumin ScFv Fusion (Merrimack) and COMBODY (Epigen Biotech), dual targeting nanobodies (Ablynx), dual targeting heavy chain only domain antibodies.

Bi-specific T-cell engagers (BiTEs) constitute a class of bi-specific single-chain antibodies for the polyclonal activation and redirection of cytotoxic T cells against pathogenic target cells. BiTEs are a class of artificial bi-specific monoclonal antibodies, which direct the T cells' cytotoxic activity against for example cancer cells. BiTEs combine a unique set of properties that have not yet been reported for any other kind of bi-specific antibody construct, namely extraordinary potency and efficacy against target cells at low T-cell numbers without the need for T-cell co-stimulation. BiTEs are fusion proteins consisting of two single-chain variable fragments (scFvs) of different antibodies, or amino acid sequences from four different genes, on a single peptide chain of about 55 kilo Daltons. One of the scFvs "arms" binds to T cells via the epsilon (epsilon) subunit of human CD3 receptor, a protein component of the signal-transducing complex of the T-cell receptor on T-cells. With the other arm, the BiTE recognizes an antigen on target cells, e.g. a tumor specific molecule on a tumor cell. T-cell activation is only seen when BiTEs are presented to T-cells while the BITE is on the surface of target cells. BiTEs transiently tether T-cells and target cells. T-cell activation by BiTEs involves upregulation of CD69, CD25 and various cell adhesion molecules, de novo expression and release of cytokines (e.g., IFN-gamma, TNF-alpha, IL-6, IL-2, IL-4 and IL-10), upregulation of granzyme and perforin expression, and cell proliferation. Redirected target cell lysis by BiTEs is independent of T-cell receptor specificity, presence of MHC class I and beta2 microglobulin, and of any co-stimulatory stimuli. This independence from regular T-cell signals and recognition molecules may be explained by the induction through BiTEs of regular cytolytic synapses and maximum membrane proximity. Displacement of negative regulatory proteins such as CD45 from BiTE-induced synapses may alleviate the need for co-stimulation. BiTEs show redirected lysis in vitro with previously unstimulated peripheral polyclonal CD8- and CD4-positive T-cells. No activity is seen with naive CD8- or CD4-positive T-cells. CD4 T-cells can upregulate granzyme B and perforin expression when stimulated with BiTEs and thereby contribute to CD8-mediated target cell lysis. In vitro, redirected lysis is seen at low picomolar concentrations, suggesting that very low numbers of BiTE molecules need to be bound to target cells for triggering T-cells. In SCID mouse models, sub-mg doses of BiTEs have been shown to completely prevent tumor outgrowth and to eradicate solid tumors up to 200 mm3.

Like some other bi-specific antibodies, and unlike ordinary monoclonal antibodies, BiTEs form a link between T cells and tumor cells. This causes T cells to exert cytotoxic activity on tumor cells by producing proteins like perforin and granzymes, independently of the presence of MHC I or co-stimulatory molecules. These proteins enter tumor cells and initiate the cell's apoptosis. This action mimics physiological processes observed during T cell attacks against tumor cells. In one embodiment the bi-specific antibody of the invention is a BiTE. In one aspect, the antibody of the invention is a BiTE targeting CD3 and CD34. In another aspect of the invention the antibody is a BiTE targeting CD3 and CD133. In another aspect of the invention the antibody is a BiTE targeting CD3 and CD59⁺. In a further aspect of the invention the antibody is a BiTE targeting CD3 and Thy1/CD90⁺. In another aspect of the invention the antibody is a BiTE targeting CD3 and C-kit/CD117.

The CD34, CD133, CD59⁺, Thy1/CD90⁺ or C-kit/CD117-specific bi-specific T-cell engagers of the present invention comprise a first binding domain that immunospecifically binds to the T-cell antigen CD3 and a second binding domain that immunospecifically binds to CD34, CD133 CD59⁺, Thy1/CD90⁺ or C-kit/CD117. In one embodiment, the first binding domain immunospecifically binds to CD3. In a specific embodiment, the first binding domain immunospecifically binds to one or more of any subunit of CD3 (e.g., the gamma, delta, zeta, or eta subunit). In a preferred embodiment, the first binding domain immunospecifically binds to the epsilon (epsilon) subunit of CD3. In a specific embodiment, the first binding domain immunospecifically binds to the epsilon (epsilon) subunit of CD3 when said subunit is complexed with the delta subunit of CD3. In another embodiment, the binding domain that binds to CD3 is deimmunized [i.e., humanised]. In another specific embodiment, the second binding domain immunospecifically binds to the extracellular domain of CD34, CD133, CD59⁺, Thy1/CD90⁺ or C-kit/CD117. In a preferred embodiment, the second binding domain of the CD34, CD133, CD59⁺, Thy1/CD90⁺ or C-kit/CD117-BiTEs, which are used in the treatment, prevention and/or management of cancer, immunospecifically binds to epitopes on CD34, CD133, CD59⁺, Thy1/CD90⁺ or C-kit/CD117 that are selectively exposed and/or increased on cancer cells as compared to non-cancer cells. In another embodiment, the second binding domain of the CD34, CD133, CD59⁺, Thy1/CD90⁺ or C-kit/CD117-BiTEs of the invention immunospecifically binds to epitopes on CD34, CD133, CD59⁺, Thy1/CD90⁺ or C-kit/CD117 that are selectively exposed and/or increased on non-cancer hyperproliferative cells as compared to non-hyperproliferative cells (more mature cells).

In a specific embodiment, a CD34, CD133, CD59⁺, Thy1/CD90⁺ or C-kit/CD117-BiTE of the invention comprises: (1) a first binding domain comprises a variable heavy (VH) domain and a variable light (VL) domain of an antibody that immunospecifically binds to the T-cell antigen CD3; and (2) a second binding domain that comprises a VH domain and a VL domain of an antibody that immunospecifically binds to CD34, CD133, CD59⁺, Thy1/CD90⁺ or C-kit/CD117. In a specific embodiment, the VH domain and VL domains of the first binding domain are linked together by a linker of sufficient length to enable the domains to fold in such a way as to permit binding to the T-cell antigen CD3. In another specific embodiment, the VH domain and VL domains of the second binding domain are linked together by a linker of sufficient length to enable the domains to fold in such a way as to permit binding to CD34, CD133, CD59⁺, Thy1/CD90⁺ or C-kit/CD117. In another specific embodiment, the first and second binding domains are linked together by a linker of sufficient length to enable the domains to fold in such a way as to permit binding to the T-cell antigen CD3 and to CD34, CD133, CD59⁺, Thy1/CD90⁺ or C-kit/CD117.

In specific embodiments, a CD34-BiTE of the invention can include, but is not limited to, any of the following arrangements in the 5' to 3' direction: (1) VH CD3-VL CD3-VH CD34-VL-CD34; (2) VL CD3-VH CD3-VH CD34-VL CD34; (3) VL CD3-VH CD3-VL CD34-VH-CD34; (4) VH CD3-VL CD3-VL CD34-VH CD34; (5) VH CD34-VL CD34-VH CD3-VL CD3; (6) VL CD34-VH CD34-VH CD3-VL CD3; (7) VL CD34-VH CD34-VL CD3-VH CD3; or (8) VH CD34-VL CD34-VL CD3-VH-CD3. In further specific embodiments, a CD133-BiTE of the invention can include, but is not limited to, any of the following arrangements in the 5' to 3' direction: (9) VH CD3-VL CD3-VH CD133-VL-CD133; (10) VL CD3-VH CD3-VH CD133-VL CD133; (11) VL CD3-VH CD3-VL CD133-VH-CD133; (12) VH CD3-VL CD3-VL CD133-VH CD133; (13) VH CD133-VL CD133-VH CD3-VL CD3; (14) VL CD133-VH CD133-VH CD3-VL CD3; (15) VL CD133-VH CD133-VL CD3-VH CD3; or (16) VH CD133-VL CD133-VL CD3-VH-CD3.

The present invention further provides compositions comprising the CD34, CD133, CD59⁺, Thy1/CD90⁺ and/or C-kit/CD117-BiTEs of the invention. In particular, the present invention provides pharmaceutical compositions comprising the CD34, CD133, CD59⁺, Thy1/CD90⁺ and/or C-kit/CD117-BiTEs of the invention and one or more pharmaceutical carriers or excipients. The present invention provides aqueous formulations, lyophilized formulations, gels, and surgical implants containing one or more of any of the CD34, CD133, CD59⁺, Thy1/CD90⁺ or C-kit/CD117-BiTEs of the invention. The present invention also provides kits comprising one or more CD34, CD133, CD59⁺, Thy1/CD90⁺ or C-kit/CD117-BiTEs of the invention, in one or more containers, and/or instructions for use of such CD34, CD133, CD59⁺, Thy1/CD90⁺ or C-kit/CD117-BiTEs.

Diabody refers to a bivalent antibody fragment constructed by gene fusion (Holliger P et al., Proc. Natl. Acad. Sci. USA 90: 6444-6448 (1993); EP 404,097; WO 93/11161; etc.). Diabody is a dimer comprising two peptide chains; in each polypeptide chain, an L chain variable region (V L) is connected to an H chain variable region (V H) on the same chain via a linker that is too short to allow pairing between the two regions (for example, about 5 residues). V L and V H encoded on the same polypeptide chain form a dimer because they cannot form a single-stranded variable region fragment due to the short linker between them. Thus, a diabody ends up with two antigen-binding sites.

The CD34, CD133, CD59⁺, Thy1/CD90⁺ or C-kit/CD117-bi-specific antibodies, such as CD34, CD133, CD59⁺, Thy1/CD90⁺ or C-kit/CD117-BiTEs, of the invention can be administered in combination with one or more other cancer therapies or used in combination with one or more other stem cell transplantation pre-treatment method. In particular, the present invention provides methods of treating, preventing and/or managing cancer, and/or methods for indirect immunosuppression, and/or for preventing infection and/or for preventing GVHD, the methods comprising administering to a subject in need thereof a therapeutically or prophylactically effective amount of one or more CD34, CD133, CD59⁺, Thy1/CD90⁺ or C-kit/CD117-bi-specific antibodies of the invention in combination with the administration of a therapeutically or prophylactically effective amount of one or more other therapies or in combination with the use of one or more stem cell transplant pre-treatment methods, or methods used after HSCT prior to a re-transplantation if relapse of the underlying malignancy occurs. Examples of other therapies/pre-treatments include chemotherapies, hormonal therapies, biological therapies/immunotherapies, radiation, surgery and stem cell transplantation.

The antibodies of the invention may also be multi-specific, targeting at least one of the markers CD34, CD133, CD59+, Thy1/CD90+ or C-kit/CD117, and at least one activating molecule, such as CD3, TCR, CD16, or NK receptors such as NKG2D, NKp44, NKp46, NKp30, and DNAM, or other activating molecules. Any combination of said markers and activating molecules are comprised within the present invention. The multi-specific antibody might be directed to at least one, such as two or three markers of the inventions, and at least one, such as two or three activating molecules of the invention.

The antibodies of the invention may be manufactured by any known suitable method used in the art. Methods of preparing bi-specific antibodies of the present invention include BiTE (Micromet), DART (MacroGenics), Fcab and Mab² (F-star), Fc-engineered IgG1 (Xencor) or DuoBody (based on Fab arm exchange, Genmab). Examples of other platforms useful for preparing bi-specific antibodies include but are not limited to those described in WO 2008/119353 (Genmab), WO 2011/131746 (Genmab) and reported by van der Neut-Kolfschoten et al. (Science. 2007 Sep. 14; 317 (5844): 1554-7). Traditional methods such as the hybrid hybridoma and chemical conjugation methods (Marvin and Zhu (2005) Acta Pharmacol Sin 26: 649) can also be used. Co-expression in a host cell of two antibodies, consisting of different heavy and light chains, leads to a mixture of possible antibody products in addition to the desired bi-specific antibody, which can then be isolated by, e.g., affinity chromatography or similar methods.

The bi-specific antibodies of the present invention are for example recombinant antibodies, generated using gene recombination techniques (see, e.g., Borrebaeck C A K and Larrick J W, Therapeutic Monoclonal Antibodies, Published in the United Kingdom by Macmillan Publishers LTD, 1990). A recombinant antibody can be obtained by cloning an antibody-encoding DNA from antibody-producing cells, such as hybridomas or sensitized lymphocytes, incorporating the DNA into an appropriate vector, and introducing the vector into a host for antibody production. A bi-specific antibody can also be prepared by chemically cross-linking Fab's. A bi-specific F(ab') 2 can be produced, for example, by maleimidating a Fab' prepared from one antibody with o-PDM (ortho-phenylenedi-maleimide) and reacting the product with a Fab' prepared from another antibody, so as to cross-link Fab's derived from different antibodies (Keler T et al. Cancer Research 1997, 57: 4008-4014). Further, a method for chemically connecting antibody fragments such as a Fab'-thionitrobenzoic acid (TNB) derivative and Fab'-thiol (SH) is also known (Brennan M et al. Science 1985, 229: 81-83). Instead of cross linkage, a leucine zipper derived from Fos and Jun or the like can be used. Although Fos and Jun also form a homodimer, their preferential heterodimer formation is utilized. A Fab' added with a Fos leucine zipper and a second Fab' added with a Jun leucine zipper are expressed for preparation. By mixing and reacting monomeric Fab'-Fos and Fab'-Jun, which have been reduced under mild conditions, a bi-specific F(ab') 2 can be formed (Kostelny S A et al. J. of Immunology, 1992, 148: 1547-53). This method is not limited to Fab' and can also be applied to scFv, Fv, etc. A bi-specific antibody can also be prepared in a form of diabody. A bi-specific diabody is a heterodimer comprising two cross-over scFv fragments. That is, a bi-specific diabody can be prepared by constructing a heterodimer using V H(A)-V L(B) and V H(B)-V L(A), which have been formed by connecting V H and V L derived from two types of antibodies: A and B, with a relatively short linker of about 5 amino acid residues (Holliger P et al. Proc. of the National Academy of Sciences of the USA 1993, 90: 6444-6448). In this case, construction of a bi-specific diabody of interest can be promoted by performing appropriate amino acid substitutions (knobs-into-holes: Zhu Z et al. Protein Science. 1997, 6: 781-788) so as to link two types of scFv's with a flexible and relatively long linker of about 15 amino acid residues (a single-chain diabody: Kipriyanov S M et al. J. of Molecular Biology. 1999, 293: 41-56).

The antibodies of the present invention include, but are not limited to, human antibody, mouse antibody, rat antibody and such, without any limitation on their origins, and may be genetically, structurally, chemically and/or in other ways modified antibodies such as chimera antibody and humanized antibody. Methods for obtaining human antibodies are known, and a human antibody of interest can be obtained, for example, by immunizing a transgenic animal having all repertoires of human antibody genes with an antigen of interest (see WO 93/12227, WO 92/03918, WO 94/02602, WO 94/25585, WO 96/34096, WO 96/33735). Genetically modified antibodies can be produced by known methods. Specifically, for example, a chimera antibody comprises variable regions from the H and L chains of an antibody from immunized animals, and constant regions from the H and L chains of a human antibody. A chimera antibody can be obtained by linking a DNA encoding the variable region of an antibody derived from immunized animals with a DNA encoding the constant region of a human antibody, inserting the resulting DNA into an expression vector, and introducing the recombinant vector into a host for production. A humanized antibody is a modified antibody also referred to as reshaped human antibody. A humanized antibody is constructed by grafting the complementarity determining region (CDR) of an antibody derived from immunized animals into the CDR of a human antibody. General genetic engineering technologies are also known.

One object of the invention is a new pre-treatment method to be used prior to stem cell transplantation, or after (e.g. prior to a re-transplantation) if relapse of the underlying malignancy occurs. The new pre-treatment method of the invention includes the administration of new antibodies of the invention, for the killing of undesired cells, which will give rise to fewer side effects (as compared to conventional treatments) and also to beneficial effects for the condition being treated by the stem cell transplantation.

One object of the invention is to kill malignant cells, in particular cancer cells such as tumor cells and/or cancer stem cells using the antibodies of the invention. The antibodies could be used in the treatment of a hematological malignancy, such as leukemia, for example ALL or AML, or a hematologic disease such as MDS, by killing malignant/undesired cells related to the malignancy/disorder (e.g., CSCs). Another object is to kill healthy and/or diseased stem cells, such as HSCs, using the antibodies of the invention. The antibody treatment can then be followed by a stem cell transplantation, in particular an allogeneic or an autologous HSCT, the antibodies reducing the risk for infection, having an indirect immunosuppressive function and preventing a GVHD reaction after transplantation, in particular since less chemotherapy will be needed in the preparatory treatment before HSCT. In a particular embodiment, the antibody treatment kills both malignant cells and stem cells before transplantation, thus treating a hematological malignancy, reducing risk of a post-transplantation infection and preventing GVHD.

Another object of the invention is to treat hematologic diseases or hematological malignancies using monoclonal antibodies directed to targets present on both undesired/malignant/cancer cells and stem cells. In one aspect, the hematological malignancy is leukemia, such as ALL, AML or AMoL. In another aspect the hematological disorder is MDS. In a further aspect the malignancy/disorder/condition is any malignancy/disorder/condition requiring or benefitting from stem cell transplantation, such as CML, CLL, other leukemias and lymphoma. One object of the invention is to treat hematological malignancies/disorders, such as ALL, AML, AMoL or MDS, requiring a stem cell transplantation, such as a allogeneic HSCT, by destroying malignant/undesired cells prior to transplantation or re-transplantation using monoclonal bi-specific antibodies, such as BiTEs, directed to targets present on both stem cells and tumor cells, such as CD34 or CD133. In one aspect, MDS is treated using a BiTE targeting CD3 and CD34, or CD3 and CD133. In another aspect, ALL is treated using a BiTE targeting CD3 and CD34, or CD3 and CD133. In another aspect, AML is treated using a BiTE targeting CD3 and CD34, or CD3 and CD133.

The treatment with this bi- or multi-specific antibody can be used either prior to a transplantation, in the preconditioning regimen, as a chemotherapeutic agent to kill off malignant clones to make patients ready for stem cell transplantation. The alternative is that patients that relapse in their underlying malignant disease after stem cell transplantation receive treatment with this invention in order to make them eligible for a re-transplantation.

To clarify the scope of the invention further, we hereby define some of the components in more detail.

As used herein, the term "undesired cell" is referring to a type of cell that is, in the current context used, negative for the wellbeing of the subject, thus considered as undesired. For example, an undesired cell could be a malignant cell, such as a cancer cell. In the context of treating for example hematological malignancies, cancer cells, such as tumor cells and/or cancer stem cells are considered undesired cells. In the context of stem cell transplants, both malignant cells present in the recipient and immune cells of the recipient may be considered undesired cells. Immune cells that contribute to rejection of the transplant or that provoke GVHD, are thus considered undesired cells in this context. Also, diseased or healthy HSCs in the recipient mediating rejection and/or obstructing the recovery of the recipient after receiving a transplant may be considered undesired in this context.

As used herein, the term "stein cell" is referring to non-fully undifferentiated biological cells, which can further differentiate into more specialized cells and can divide (through mitosis) to produce more stem cells. The term "progenitor cell" may also be used, even though the progenitor cells cannot replicate indefinitely as stem cells can they still can give rise to more differentiated daughter cells. One type of stem cells is the hematopoietic stem cell, HSC, which is the blood cell that gives rise to all the other blood cells. The hematopoietic stem cells give rise to the myeloid (monocytes and macrophages, neutrophils, basophils, eosinophils, erythrocytes, megakaryocytes/platelets, dendritic cells), and lymphoid lineages (T-cells, B-cells, NK-cells). In the context of the invention, stem cells are mostly referring to HSCs, if not denoted otherwise.

As used herein, the term "malignant cell" is referring to a cell that is contributing to a disease, disorder or unwanted condition in the subject treated. Such cells are for example cancer cells, both tumor cells and cancer stem cells. Other examples may be HSCs or immune cells originating from HSCs of a transplant recipient, which are attacking the transplant and give rise to GVHD.

As used herein, the term "cancer cell" is referring to cells that grow and divide at an unregulated, quickened pace. Cancer cells are malignant neoplastic cells that may form tumors and give rise to cancer disorders in the afflicted subject. Cancer cells may include both cancer stem cells and tumor cells.

As used herein, the term "cancer stem cell" (CSC) is referring to cancer cells, found within e.g. tumors or hematological cancers, that possess characteristics associated with normal stem cells, specifically the ability to give rise to all cell types found in a particular cancer sample. CSCs are therefore tumorigenic (tumor-forming), perhaps in contrast to other non-tumorigenic cancer cells. CSCs may generate tumors through the stem cell processes of self-renewal and differentiation into multiple cell types. Such cells are proposed to persist in tumors as a distinct population and cause relapse and metastasis by giving rise to new tumors.

As used herein, the term "tumor cell" is referring to a neoplastic cell that together with other tumor cells form a cell aggregation or lump called a tumor. Malignant tumor cells are considered to be cancer cells.

As used herein, the term "bone marrow transplantation" or "stem cell transplantation" used herein should be considered as interchangeable, referring to the transplantation of stem cells in some form to a recipient. The stem cells do not necessarily have to be derived from bone marrow, but could also be derived from other sources such as umbilical cord blood.

As used herein, the term "HSCT" is referring to a transplantation of hematopoietic stem cells (HSCs) to a recipient, wherein the stem cells usually are collected from bone marrow, peripheral blood, or umbilical cord blood.

As used herein, the term "allogeneic transplantation" is referring to a transplantation wherein the recipient and donor are different individuals, wherein the term "autologous transplantation" is referring to a transplantation wherein the recipient and donor are the same individual, i.e. the transplant originates from the patient him/herself.

As used herein, the term "first transplantation" is referring to a transplantation given to a subject for the treatment of a condition, who has not received such transplantation before, or who has not received such transplantation for the treatment of said condition before. The term "re-transplantation" is considering a transplantation given to a subject who has already received such transplantation one or several times before.

As used herein, the term "prior to transplantation" in the context of administering an antibody of the invention, is referring to a timeframe of hours, days or weeks before the transplantation. In particular, the antibodies of the invention are administered for a few days up to a few weeks, such as 1-7 days or 1-4 weeks before the transplantation. The antibodies may be administered continuously during this time period, or at a single or a few occasions. The antibody should be administered in an effective dose, at a number of occasions and for a sufficient time before the transplantation, so that malignant cells and/or other undesired cells are killed. Such an administration protocol is considered close at hand for the skilled person having access to the specific antibody used. For example, the antibody may be administered continuously once a day during a one-week period prior to transplantation, and allowed to clear out of the system for a couple of days before transplantation. It is important that the time between the administration of the antibody and the stem cell transplantation should be sufficient for the antibody to have been cleared from the system of the recipient before the recipient is given the stem cell transplant, to avoid the antibody from attacking the HSCs in the transplant. Any such time frames are known or readily determined by the person skilled in the art having access to the half-life data of the antibody.

As used herein, the terms "subject" and "patient" are used interchangeably. As used herein, a subject is an animal, preferably a mammal such as a non-primate (e.g., cows, pigs, horses, cats, dogs, rats, etc.) and a primate (e.g., monkey (e.g., a rhesus monkey, a cynomolgus monkey or chimpanzee) and human), and most preferably a human.

As used herein, the term "subject in need thereof" in the context of therapy, is referring to a subject or patient suffering from a disorder or disease, and that will benefit from said therapy, i.e. is in need thereof.

As used herein, the term "recipient" in the context of transplantation is referring to the subject receiving the transplantation, in contrast to the "donor", which is the subject the material (cells) to be transplanted originates from. In an allogeneic setting, the recipient and the donor are different individuals, in an autologous setting, the recipient and the donor is the same individual. In a syngeneic setting, the donor and recipient are different individuals but are genetically identical. Xenogeneic setting means the donor is from another species than the recipient.

As used herein, the terms "administering", or "administration" an antibody of the invention to a subject refers to the delivering of said antibody to the subject by any suitable method known in the art. The administration could be intravenous, peripherally, oral, intramuscular, parenteral or any other suitable way to administer an antibody.

As used herein, the terms "treat", "treatment" and "treating" in the context of administering a therapy(ies) to a subject refer to the reduction or amelioration of the progression, severity, and/or duration of a disorder, and/or the amelioration of one or more symptoms thereof resulting from the administration of one or more therapies (including, but not limited to, the administration of one or more prophylactic or therapeutic agents). In the current invention, a treatment with antibodies of the invention increases the chance of success and minimizes the risks of succeeding stem cell transplantation. The treatment herein thus includes the administration of the antibodies of the invention.

As used herein, the term "pre-treatment" is referring to a treatment that is performed prior to another treatment or therapy. Also used is the term "pre-conditioning" which refers generally to what occurs when an animal is exposed to a stressor or stimulus in order to prepare it for a later encounter with a similar stressor or stimulus. For example, in vaccinations, a human is exposed to an artificially weakened virus in order to stimulate the body's immune system to produce antibodies that fight the virus. Then, when the live virus is encountered, the body can vigorously defend against it, already having produced the relevant antibodies. The antibodies of the invention might be used as a pre-conditioning before transplantation. In a particular embodiment of the current invention, the pre-treatment is a treatment performed prior to stem cell transplantation. The preferred pre-treatments of the invention are antibody-based immunotherapies using the new antibodies of the invention.

As used herein, the term "effective amount" refers to the amount of a therapy (e.g., a prophylactic or therapeutic agent) which is sufficient to reduce and/or ameliorate the severity and/or duration of a disorder, or a symptom thereof, prevent the advancement of said disorder, cause regression of said disorder, prevent the recurrence, development, or onset of one or more symptoms associated with said a disorder, or enhance or improve the prophylactic or therapeutic effect(s) of another therapy (e.g., another prophylactic or therapeutic agent). An "effective amount" of the antibodies of the invention used in a pre-treatment prior to stem cell transplantation, or after if relapse of the underlying malignancy occur, is thus the amount which is sufficient to reduce and/or ameliorate the severity and/or duration and/or relapse of a disorder such as a hematological disorder, and/or prevent the recurrence, development, or onset of one or more symptoms associated with said disorder, and/or an amount sufficient to reduce the risk of GVHD upon a succeeding stem cell transplantation, and/or efficiently eliminate a sufficient number of HSCs in order to prevent rejection of the donor graft or treat relapse after stem cell transplantation by eliminating HSC/malignant cells of recipient origin.

As used herein, the terms "prevent," "preventing," and "prevention" in the context of therapies administered to a subject refer to the reduction or inhibition of the development, onset, spread or recurrence/relapse of a disorder associated with the use of another pre-treatment before stem cell transplantation or no pre-treatment at all, or a symptom thereof in a subject, resulting from the administration of a therapy (e.g., a prophylactic or therapeutic agent), or the administration of a combination of therapies (e.g., a combination of prophylactic or therapeutic agents). In a specific embodiment, the terms "prevent," "preventing," and "prevention" in the context of therapies administered to a subject refer to the increase in the time to recurrence or a decrease in the spread or progression of a disorder, wherein the disorder is associated with the use of another pre-treatment before stem cell transplantation or no pre-treatment at all. For example the pre-treatment using the antibodies of the invention might prevent the relapse of a malignant disease and/or prevent or minimize the occurrence or risk of GVHD, in particular since less chemotherapy will be needed in the preparatory treatment given before HSCT.

As used herein, the term "indirect immunosuppressive" effect/action is referring to an immunosuppressive effect which is indirect or delayed due to the eradication of HSCs in the recipient subject before receiving HSCT, since the recipient subject's matured immune cells are still present but the subject is unable to form more mature immune cells originating from his/her own HSCs. The effect of said indirect immunosuppressive treatment will also last longer and/or be more permanent, than striking mature immune cells directly.

As used herein, the term "marker" is referring to genes and their protein products used by scientists to isolate and/or identify a certain cell type. In the context of the invention, an antibody directed to a certain marker is referring to an antibody directed to an antigen wherein the antigen itself is a marker of a certain cell type.

As used herein, the terms "specific HSC marker" or "HSC specific marker" are used interchangeably herein and are referring to markers commonly used to identify HSCs, and which are almost solely expressed on HSCs and usually not present, or present in very low amounts, on other more mature cells in the hematopoietic system (or other cells for example endothelial cells), and thus considered as HSC-specific. Such markers include CD34, CD133, CD59$^+$, Thy1/CD90$^+$ and C-kit/CD117. Targeting these markers will thus mostly target HSCs and not other more mature hematopoietic cells or cells in other tissues.

As used herein, the term "marker shared by" two/several different cells refers to a marker that is present on/in both/all cells, or used to identify both/all cells, said to share that marker. An antibody targeting said marker antigen can thus bind to all cells sharing said marker antigen. A shared tumor/stem cell or tumor/HSC marker is referring to a marker, which may be used to identify both tumor cells and stem cells, such as HSCs.

As used herein, the term "activating molecule" is referring to substance/compound/molecule that, when targeted by an antibody, enhances the response to said antibody in effector cells, such as T cells, NK cells or macrophages. Thus, an antibody selective for an activating molecule and a second target will have a stronger effector cell response than an antibody only targeting said second target. The activating molecules of the invention could be for example CD3, TCR, CD16, or other activating molecules. Additional, non-limiting examples of activating molecules include NK receptors such as NKG2D, NKp44, NKp46, NKp30, and/or DNAM.

As used herein, the term "non-malignant" disorder or condition refers to conditions that affect the wellbeing and health of the subject suffering from said non-malignant conditions/disorders, but without the presence of malignant cells. Such conditions include but are not limited to Severe aplastic anemia (SAA), Wiskott Aldrich Syndrome, Hurlers Syndrome, FHL, CGD, Kostmanns syndrome, Severe immunodeficiency syndrome (SCID), other autoimmune disorders such as SLE, Multiple sclerosis, IBD, Crohns Disease, Ulcerative colitis, Sjögrens syndrome, vasculitis, Lupus, Myasthenia Gravis, Wegeners disease, inborn errors of metabolism and/or other immunodeficiencies.

As used herein, the term "hematologic diseases" or "hematological disorders" is used interchangeable herein, and is referring to disorders that primarily affect the cells of hematological origin, in common language denoted as cells of the blood. Hematological disease includes myeloid, hematological malignancies, and miscellaneous disorders.

As used herein, the term "hematological malignancies" or "hematological cancers" should be considered as interchangeable, and refers to the types of cancer that affect blood, bone marrow, and lymph nodes, these includes lymphomas, myelomas, plasmacytoma, and leukemias.

As used herein, the terms "antibody" or "antibodies" refer to molecules that contain an antigen binding site, e.g., immunoglobulin molecules and immunologically active fragments of immunoglobulin molecules that contain an antigen binding site. Immunoglobulin molecules can be of any type (e.g., IgG, IgE, IgM, IgD, IgA and IgY), class (e.g., IgG1, IgG2, IgG3, IgG4, IgA1 and IgA2) or a subclass of immunoglobulin molecule. Antibodies include, but are not limited to, synthetic antibodies, monoclonal antibodies, single domain antibodies, single chain antibodies, recombinantly produced antibodies, multi-specific antibodies (including bi-specific antibodies), human antibodies, humanized antibodies, chimeric antibodies, intrabodies, scFvs (e.g., including mono-specific and bi-specific, etc.), Fab fragments, F(ab') fragments, disulfide-linked Fvs (sdFv), anti-idiotypic (anti-Id) antibodies, and epitope-binding fragments of any of the above.

As used herein, the term antibody "directed to" or "directed against" are used interchangeably herein and refer to an antibody that is constructed to direct its binding specificity(ies) at a certain target/marker/epitope/antigen, i.e. an antibody that immunospecifically binds to a target/marker/epitope/antigen. Also, the expression antibodies "selective for" a certain target/marker/epitope may be used, having the same definition as "directed to" or "directed against". A bi-specific antibody directed to (selective for) two different targets/markers/epitopes/antigens binds immunospecifically to both targets/markers/epitopes/antigens. If an antibody is directed to a certain target antigen, such as CD34, it is thus assumed that said antibody could be directed to any suitable epitope present on said target antigen structure.

As used herein, the term "antibody fragment" is a portion of an antibody such as F(ab').sub.2, F(ab).sub.2, Fab', Fab, Fv, scFv and the like. Regardless of structure, an antibody fragment binds with the same antigen that is recognized by the intact antibody. For example, an anti-HLA-DR antibody fragment binds to HLA-DR The term "antibody fragment" also includes isolated fragments consisting of the variable regions, such as the "Fv" fragments consisting of the variable regions of the heavy and light chains and recombinant single chain polypeptide molecules in which light and heavy variable regions are connected by a peptide linker ("scFv proteins"). As used herein, the term "antibody fragment" does not include portions of antibodies without antigen binding activity, such as Fc fragments or single amino acid residues.

As used herein, the term "epitope" or "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation.

As used herein, the term "T-cell receptor" or "TCR" is used as a common nominator for all variants of TCRs, i.e. both if they are consisting of an alpha and Beta chain, or a gamma and delta chain. It also involves all variants of the four chain types alpha, beta, delta and gamma.

As used herein, the term "immunospecifically binds to" CD34, CD133, CD59$^+$, Thy1/CD90$^+$ or C-kit/CD117, and analogous terms in the context of anti-CD34, anti-CD133, anti-CD59$^+$, anti-Thy1/CD90$^+$ or anti-C-kit/CD117 antibodies, CD34, CD133, CD59$^+$, Thy1/CD90$^+$ or C-kit/CD117-BiTEs, and binding domains of CD34, CD133, CD59$^+$, Thy1/CD90$^+$ or C-kit/CD117-BiTEs, refer proteinaceous agents, including antibodies and the binding domains of CD34, CD133, CD59$^+$, Thy1/CD90$^+$ or C-kit/CD117-BiTEs that specifically bind to an CD34, CD133, CD59$^+$, Thy1/CD90$^+$ or C-kit/CD117 polypeptide, and do not specifically bind to non-CD34, CD133, CD59$^+$, Thy1/CD90$^+$ or C-kit/CD117 polypeptides. Preferably, antibodies and binding domains of CD34, CD133, CD59$^+$, Thy1/CD90$^+$ or C-kit/CD117-BiTEs, that specifically bind to an CD34, CD133, CD59$^+$, Thy1/CD90$^+$ or C-kit/CD117 polypeptide do not cross-react with other non-related antigens. In specific embodiments, anti-CD34, anti-CD133, anti-CD59$^+$, anti-Thy1/CD90$^+$ or anti-C-kit/CD117 antibodies of the invention bind to an CD34, CD133, CD59$^+$, Thy1/CD90$^+$ or C-kit/CD117 polypeptide with little or no cross-reactivity with other non-related antigens, as measured by a standard assay known in the art, such as an ELISA assay. In certain embodiments, antibodies and binding domains of CD34, CD133, CD59$^+$, Thy1/CD90$^+$ or C-kit/CD117-BiTEs that immunospecifically bind to a CD34, CD133, CD59$^+$, Thy1/CD90$^+$ or C-kit/CD117 polypeptide may be cross-reactive with related antigens. Preferably, antibodies or fragments thereof that immunospecifically bind to a CD34, CD133, CD59$^+$, Thy1/CD90$^+$ or C-kit/CD117 polypeptide can be identified, for example, by immunoassays or other techniques known to those of skill in the art. An antibody or fragment thereof binds specifically to a CD34, CD133, CD59+, Thy1/CD90+ or C-kit/CD117 polypeptide when it binds to a CD34, CD133, CD59+, Thy1/CD90+ or C-kit/CD117 polypeptide with higher affinity than to any cross-reactive antigen as determined using experimental techniques, such as radioimmunoassays (RIAs) and enzyme-linked immunosorbent assays (ELISAs). See, e.g., Paul, ed., 1989, Fundamental Immunology, 2 nd ed., Raven Press, New York at pages 332-336 for a discussion regarding antibody specificity. Preferably, antibodies and binding domains of CD34, CD133, CD59+, Thy1/CD90+ or C-kit/CD117-BiTEs that immunospecifically bind to a CD34, CD133, CD59+, Thy1/CD90+ or C-kit/CD117 polypeptide only modulate a CD34, CD133, CD59+, Thy1/CD90+ or C-kit/CD117 activity(ies) and do not significantly affect other activities. As used herein, the term "immunospecifically binds to CD3" and analogous terms refer to proteinaceous agents that specifically bind to CD3 or a subunit thereof, and do not specifically bind to other antigens. Preferably, antibodies and binding domains of CD34, CD133, CD59+, Thy1/CD90+ or C-kit/CD117-BiTEs that immunospecifically bind to CD3 do not cross-react with non-related antigens. As used herein, the term "immunospecifically binds to" and analogous terms in general refer to proteinaceous agents that specifically bind to a specific antigen or a subunit thereof, and do not specifically bind to other antigens.

As used herein, the term "bi-specific antibody" refers to an antibody that immunospecifically bind two target antigens. A bi-specific antibody according to the present invention is a molecule comprising two types of antibodies or antibody fragments having specificities for different antigens. The bi-specific antibody is, not particularly limited, but preferably monoclonal.

As used herein, the term "BITE" refers to a bi-specific antibody with one specificity for T cells, such as via the CD3 receptor, and the other specificity for a second cell type, such as a tumor cell via a tumor specific molecule. When targeting cancer, the action of BiTEs mimics the physiological processes observed during T-cell attacks against tumor cells, the BiTEs form a link between T-cells and tumor cells causing T-cells to exert cytotoxic activity on tumor cells and initiate the target cell's apoptosis.

Specifically, one embodiment of the invention includes a pre-treatment or pre-conditioning method for use prior to stem cell transplantation, wherein monoclonal antibodies directed to hematopoietic stem cell (HSC) specific marker(s) and/or marker(s) shared by malignant cells and HSC, are administered to a subject in need thereof.

The method above, wherein the method is used for decreasing, destroying or killing undesired cells in a patient prior to stem cell transplantation.

The method above, wherein the hematopoietic stem cell markers are chosen from CD34, CD133, CD59+, Thy1/CD90+ and/or C-kit/CD117 or any combination thereof.

The method above, wherein the stem cell transplantation is HSCT. The method above, wherein the HSCT transplantation is allogeneic or autologous.

The method above, wherein the undesired cells are HSCs or malignant cells, wherein the malignant cells are cancer cells, such as tumor cells or cancer stem cells (CSCs).

The method above, wherein the stem cell transplantation is used as a therapy for a non-malignant condition, disorder or malignancy. In a particular embodiment, the non-malignant condition, disorder or malignancy is hematologic.

The method above, wherein the hematologic disorder is MDS.

The method above, wherein the hematological malignancy is leukemia, wherein the leukemia is ALL, AML or AMoL.

The method above, wherein the non malignant condition is Severe aplastic anemia (SAA), Wiskott Aldrich Syndrome, Hurlers Syndrome, FHL, CGD, Kostmanns syndrome, Severe immunodeficiency syndrome (SCID), other autoimmune disorders such as SLE, Multiple sclerosis, IBD, Crohns Disease, Ulcerative colitis, Sjögrens syndrome, vasculitis, Lupus, Myasthenia Gravis, Wegeners disease, inborn errors of metabolism and/or other immunodeficiencies.

The method above, wherein the method is used for preventing and/or reducing GVHD.

The method above, wherein the monoclonal antibody is multi-specific. The method above, wherein the monoclonal antibody is bi-specific.

The method above, wherein the antibody is directed to at least one activating molecule on effector cells and at least one marker specific for HSC and/or shared by malignant cells and HSC.

The method above, wherein the activating molecule is CD3, TCR, CD16, NKG2D, NKp44, NKp46, NKp30, and/or DNAM.

The method above, wherein the marker is CD34. The method above, wherein the marker is CD133, CD59+, Thy1/CD90+ and/or C-kit/CD117.

The method above, wherein the bi-specific antibody is a BiTE. The method above, wherein the bi-specific antibody is a BiTE directed to CD3 and CD34. The method above, wherein the bi-specific antibody is a BiTE directed to CD3 and CD133, CD3 and CD59+, CD3 and Thy1/CD90+, or CD3 and C-kit/CD117.

The method above, wherein the stem cell transplantation is a first stem cell transplantation.

The method above, wherein the stem cell transplantation is a re-transplantation, e.g. after relapse.

The invention further includes a monoclonal antibody directed to HSC specific markers and/or markers shared by malignant cells and HSCs.

The antibody above, wherein the antibody is multi-specific.

The antibody above, wherein the antibody is bi-specific.

The antibody above, wherein the antibody is directed to at least one activating molecule on effector cells and at least one marker specific for HSCs and/or shared by malignant cells and HSCs.

The antibody above, wherein the activating molecule(s) is CD3, TCR, CD16, NKG2D, NKp44, NKp46, NKp30, and/or DNAM.

The antibody above, wherein the marker(s) is CD34, CD133, CD59+, Thy1/CD90+ and/or C-kit/CD117.

The antibody above, wherein the malignant cells are cancer cells. The antibody above, wherein the cancer cells are CSCs and/or tumor cells.

The antibody above, wherein the antibody is a BiTE. The antibody above, wherein the BiTE is directed to CD3 and CD34. The antibody above, wherein the BiTE is directed to CD3 and CD133, CD3 and CD59+, CD3 and Thy1/CD90+, or CD3 and C-kit/CD117.

The antibody above, for use in the treatment of a condition, disorder or malignancy.

Use of the antibody as above, in the treatment of a non-malignant condition, disorder or malignancy. The use as above, wherein the malignancy is a hematological malignancy or hematologic disorder. The use as above, wherein the hematologic disorder is MDS. The use as above, wherein the hematological malignancy is leukemia. The use as above, wherein the leukemia is ALL, AML or AMoL. The use as above, wherein the non malignant condition is Severe aplastic anemia (SAA), Wiskott Aldrich Syndrome, Hurlers Syndrome, FHL, CGD, Kostmanns syndrome, Severe immunodeficiency syndrome (SCID), other autoimmune disorders such as SLE, Multiple sclerosis, IBD, Crohns Disease, Ulcerative colitis, Sjögrens syndrome, vasculitis, Lupus, Myasthenia Gravis, Wegeners disease, inborn errors of metabolism and/or other immunodeficiencies.

The use as above, for prevention or reduction of GVHD.

The antibody as defined above, for destroying undesired cells in a patient prior to stem cell transplantation.

Use of the antibody defined above, for destroying undesired cells in a patient prior to bone marrow transplantation.

The use as above, wherein the undesired cells are stem cells. The use as above, wherein the stem cells are HSC.

The use as above, wherein the undesired cells are malignant cells. The use as above, wherein the malignant cells are cancer cells. The use as above, wherein the cancer cells are CSCs. The use as above, wherein the cancer cells are tumor cells.

The invention will now be described with reference to the following figures and examples. It should be appreciated that these examples are not intended to limit the scope of the claims to the invention, but are rather intended to be exemplary of certain embodiments. Any variations in the exemplified methods that occur to the skilled artisan are intended to fall within the scope of the invention.

Accordingly, a first aspect of the invention provides a therapeutic agent comprising or consisting of:
(a) one or more binding moiety with specificity for hematopoietic stem cells and/or hematopoietic progenitor cells; and
(b) one or more binding moiety with specificity for one or more type of effector cell.

By "an agent" we include any purified or isolated natural or chemically-synthesised entity comprising one or more molecule.

By "binding moiety" we include a region or regions of the agent of the invention capable of reversibly and/or irreversibly associating with a region or regions of another molecule or molecules by covalent and/or ionic interaction.

The agent may be produced as a fusion compound by recombinant DNA techniques whereby a length of DNA comprises respective regions encoding the two moieties of the agent of the invention either adjacent one another or separated by a region encoding a linker peptide which does not destroy the desired properties of the agent. Conceivably, the two portions of the agent may overlap wholly or partly.

By "effector cell" we include cells of the immune system directly involved in cell-mediated immunity, such as neutrophils, eosinophils, mast cells, monocytes, T cells (e.g., cytotoxic T cells), Natural Killer (NK) cells, NKT cells, macrophages and macrophage-like cells. The immune effector cells may be cytotoxic, for example, T cells (e.g., cytotoxic T cells), NK cells and NKT cells.

By "binding moiety with specificity for" we mean a binding moiety which is capable of binding to its target cell and/or ligand. It is preferred that the binding moiety is capable of binding to its target cell and/or ligand in vivo, i.e. under the physiological conditions in which the target exists inside the body. Such binding specificity may be determined by methods well known in the art, such as e.g. ELISA, immunohistochemistry, immunoprecipitation, Western blots and flow cytometry using transfected cells expressing the cognate ligand(s).

In another embodiment, the binding moiety is capable of binding to its target cell and/or ligand selectively. By "capable of binding selectively" we include binding moieties which bind at least 10-fold more strongly to its target cell and/or ligand than to another target cell and/or ligand; for example at least 50-fold more strongly or at least 100-fold more strongly. The binding moiety may be capable of binding selectively to its target cell and/or ligand under physiological conditions, e.g. in vivo. Suitable methods for measuring relative binding strengths include immunoassays, for example where the binding moiety is an antibody (see Harlow & Lane, "Antibodies: A Laboratory", Cold Spring Harbor Laboratory Press, New York, which is incorporated herein by reference). Alternatively, binding may be assessed using competitive assays or using Biacore® analysis (Biacore International AB, Sweden).

In an alternative or additional embodiment the agent comprises or consist of binding moieties selected from the group consisting of:
(i) an antibody or antigen-binding fragment thereof, or a variant, fusion or derivative of said antibody or antigen-binding fragment, or a fusion of a said variant or derivative thereof;
(ii) antibody mimics (for example, based on non-antibody scaffolds);
(iii) RNA aptamers;
(iv) Small molecules; and
(v) CovX-bodies.

CovX-Bodies are created by covalently joining a pharmacophore via a linker to the binding site of a specially-designed antibody, effectively reprogramming the antibody (Tryder et al., 2007, *Bioorg. Med. Chem. Lett.*, 17:501-6). The result is a new class of chemical entities that is Banned where each component contributes desirable traits to the intact CovX-Body—in particular, the entity has the biologic actions of the peptide and the extended half-life of the antibody.

Preferably, the target cell and/or ligand is a human target or ligand, but it may be from any mammal such as a domesticated mammal (preferably of agricultural or commercial significance including a horse, pig, cow, sheep, dog and cat). By "mammalian protein" we include any protein found in, derived from, and/or isolated from, one or more cells of a mammal; for example, the term "human protein" includes a protein found in, derived from, and/or isolated from one or more cells of a human.

In an alternative or additional embodiment the effector cell is selected from the group consisting of neutrophils, eosinophils, monocytes, mast cells, T cells (e.g., cytotoxic T cells), Natural Killer (NK) cells, NKT cells, macrophages and macrophage-like cells. Hence, the effector cell may be a cytotoxic effector cell such as a cytotoxic effector cell may be selected from the group consisting of T cells (e.g., cytotoxic T cells and/or gamma/delta T cells), NK cells and NKT cells. Hence, the effector cell may be a T cell, such as a cytotoxic T cell.

In an alternative or additional embodiment the one or more binding moiety with specificity for one or more type of effector cell has specificity for a ligand selected from the group consisting of CD3, TCR, CD16, NKG2D, NKp44, NKp46, NKp30 and DNAM.

In an alternative or additional embodiment the ligands of the invention are used as sole markers. In an alternative or additional embodiment the ligands of the invention are used in combination.

Hence, the one or more binding moiety with specificity for one or more type of effector cell may have specificity for a ligand selected from the group consisting of CD3, TCR or CD16.

In an alternative or additional embodiment the one or more binding moiety with specificity for one or more type of effector cell has specificity for an activating moiety or the ligand of the binding moiety with specificity for one or more type of effector cell is an activating moiety.

By "activating moiety" we include any cell or cell-derived moiety capable of initiating an immune response in a cell. In particular we include cell surface proteins capable of initiating a cell-mediated immunity in a cell such as a T cell. Suitable activating molecules include CD3 and TCR.

Hence, in an alternative or additional embodiment the one or more binding moiety with specificity for one or more type of effector cell is capable of activating a cell-mediated immune response in the one or more type of effector cell.

In an alternative or additional embodiment the one or more binding moiety with specificity for one or more type of effector cell has specificity for CD3. The CD3 may be selected from the group of proteins described by database accession numbers NP_000723.1 (CD3 delta), NP_000724.1 (CD3 epsilon) and NP_000064.1 (CD3 gamma). Hence, the one or more binding moiety may have binding specificity for the CD3 delta, epsilon and/or gamma subunits.

In an alternative or additional embodiment the hematopoietic stem cells and/or hematopoietic progenitor cells comprise or consist of cancer stem cells and/or normal (i.e., non-cancer) stem cells. Hence, the one or more type of stem cell may exclude cancer stem cells or normal (i.e., non-cancer) stem cells.

In an alternative or additional embodiment the one or more binding moiety with specificity for hematopoietic stem cells and/or hematopoietic progenitor cells has specificity for a ligand selected from the group consisting of CD34, CD133, CD59, Thy1/CD90 and C-kit/CD117.

In an alternative or additional embodiment the binding moiety with specificity for hematopoietic stem cells and/or hematopoietic progenitor cells has specificity for CD34.

In an alternative or additional embodiment the CD34 is described by database accession number NP_001020280.1.

In an alternative or additional embodiment the one or more binding moiety with specificity for hematopoietic stem cells and/or hematopoietic progenitor cells has specificity for CD133, for example, the protein described by database accession number NP_001139319.1.

In an alternative or additional embodiment the ligand of the one or more binding moiety with specificity for hematopoietic stem cells and/or hematopoietic progenitor cells is localized on the surface of a stem cell.

By "localised on the surface of a stem cell" we include the meaning that the ligand is associated with the cell such that one or more region of the ligand is present on outer face of the cell surface. For example, the ligand may be inserted into the cell plasma membrane (i.e., orientated as a transmembrane protein) with one or more region presented on the extracellular surface. Alternatively, the entire ligand may be outside the cell with covalent and/or ionic interactions localising it to a specific region or regions of the cell surface. The stem cell may be a cancer stem cell and/or a normal (non-cancer) stem cell.

In an alternative or additional embodiment the one or more binding moiety with specificity for hematopoietic stem cells and/or hematopoietic progenitor cells:

(a) has specificity for greater than 50% the daughter cells of the hematopoietic stem cells and/or hematopoietic progenitor cells, for example, greater than or equal to 55%, ≥60%, ≥65%, ≥70%, ≥75%, ≥80%, ≥85%, ≥90%, ≥95%, ≥96%, ≥97%, ≥98%, ≥99% or 100% of the daughter cells of the hematopoietic stem cells and/or hematopoietic progenitor cells;

(b) does not have specificity for the daughter cells of the hematopoietic stem cells and/or hematopoietic progenitor cells; or (c) has specificity for less than or equal to 50% of the daughter cells of the hematopoietic stem cells and/or hematopoietic progenitor cells, for example, ≤45%, ≤40%, ≤35%, ≤30%, ≤25%, ≤20%, ≤15%, ≤10%, ≤5%, ≤4%, ≤3%, ≤2%, ≤1%, ≤0.5% or ≤0.1% of the daughter cells of the hematopoietic stem cells and/or hematopoietic progenitor cells.

By 'daughter cells of the hematopoietic stem cells and/or hematopoietic progenitor cells' we include any non-stem cell produced by the division of a hematopoietic stem cell and/or hematopoietic progenitor cell. Hence, the daughter cells may include or exclude progenitor cells. The daughter cells may relate to fully differentiated daughter cells only.

In an alternative or additional embodiment the agent comprises one or more binding moiety with specificity for hematopoietic stem cells and/or hematopoietic progenitor cells, for example, 2, 3, 4, 5, 6, 7, 8, 9 or 10 binding moieties with specificity for one or more type of stem cell.

In an alternative or additional embodiment the agent comprises one or more binding moiety with specificity for one or more type of effector cell, for example, 2, 3, 4, 5, 6, 7, 8, 9 or 10 binding moieties with specificity for one or more type of effector cell.

Hence, in an alternative or additional embodiment the agent comprises one or more binding moiety for CD3, one or more binding moiety for CD34 and one or more binding moiety for CD133.

In an alternative or additional embodiment the one or more binding moiety with specificity for hematopoietic stem cells and/or hematopoietic progenitor cells and/or the one or more binding moiety with specificity for one or more type of effector cell are selected from the group consisting of: antibody or antigen-binding fragment thereof, or a variant, fusion or derivative of said antibody or antigen-binding fragment, or a fusion of a said variant or derivative thereof.

By "antibody" we include substantially intact antibody molecules, as well as chimaeric antibodies, humanised antibodies, human antibodies (wherein at least one amino acid is mutated relative to the naturally occurring human antibodies), single chain antibodies, bispecific antibodies, antibody heavy chains, antibody light chains, homodimers and heterodimers of antibody heavy and/or light chains, and antigen binding fragments and derivatives of the same. For example, the antibody or antigen-binding fragment, or variant, fusion or derivative thereof, may comprise, consist or consist essentially of an intact antibody. By "consist essentially of" we mean that the antibody or antigen-binding fragment, variant, fusion or derivative thereof consists of a portion of an intact antibody sufficient to retain binding specificity for its ligand.

The term 'antibody' also includes all classes of antibodies, including IgG, IgA, IgM, IgD and IgE. Thus, the antibody may be an IgG molecule, such as an IgG1, IgG2, IgG3, or IgG4 molecule.

In an alternative or additional embodiment the one or more binding moiety with specificity for hematopoietic stem cells and/or hematopoietic progenitor cells and/or the one or more binding moiety with specificity for one or more type of effector cell comprises or consists of an antigen-binding fragment selected from the group consisting of Fv fragments (e.g., single chain Fv, disulphide-bonded Fv and domain antibodies), and Fab-like fragments (e.g., Fab fragments, Fab' fragments and F(ab)$_2$ fragments).

In an alternative or additional embodiment the antigen binding fragment is a Fab fragment. The Fab fragment may include single domain antibodies from cameloids, single domain antibodies from sharks and isolated $V_H$ or $V_L$ domains from humans.

In an alternative or additional embodiment the antibody is, or the antibody fragment was derived from, an IgG antibody, for example, an IgG2 or IgG4 antibody (such as an IgG4 antibody in which the Serine amino acid at position 241 has been substituted with a Proline residue ((i.e. S241P)—such a substitution is known to stabilise the disulphide bridges in IgG4 molecule, resulting in a more stable antibody (Angal et al., 1993, Mol. Immunol., 30:105-8).

In an alternative or additional embodiment the antibody is a recombinant antibody.

In an alternative or additional embodiment wherein the antibody is an unnatural antibody.

By 'unnatural antibody' we include antibodies and fragments thereof that are not found in nature and/or natural antibodies that have been subsequently modified.

In an alternative or additional embodiment the antibody is a monoclonal antibody.

In an alternative or additional embodiment the agent is in an isolated and/or purified form.

In an alternative or additional embodiment the antibody is a non-naturally occurring antibody. In an alternative or additional embodiment, where the antibody is a naturally occurring antibody, it is provided in an isolated form (i.e. distinct from that in which it is found in nature).

In an alternative or additional embodiment the antibody or antigen-binding fragment thereof is human or deimmunized (humanised).

It will be appreciated by persons skilled in the art that, for human therapy or diagnostics, humanised antibodies may be used. Humanised forms of non-human (e.g. murine) antibodies are genetically engineered chimaeric antibodies or antibody fragments having minimal-portions derived from non-human antibodies. Humanised antibodies include antibodies in which complementary determining regions of a human antibody (recipient antibody) are replaced by residues from a complementary determining region of a non human species (donor antibody) such as mouse, rat of rabbit having the desired functionality. In some instances, Fv framework residues of the human antibody are replaced by corresponding non-human residues. Humanised antibodies may also comprise residues which are found neither in the recipient antibody nor in the imported Complementarity Determining Region (CDR) or framework sequences. In general, the humanised antibody will comprise substantially all of at least one, and typically two, variable domains, in which all or substantially all of the complementarity determining regions correspond to those of a non-human antibody and all, or substantially all, of the framework regions correspond to those of a relevant human consensus sequence. Humanised antibodies optimally also include at least a portion of an antibody constant region, such as an Fc region, typically derived from a human antibody (see, for example, Jones et al., 1986. Nature 321:522-525; Riechmann et al., 1988, Nature 332:323-329; Presta, 1992, Curr. Op. Struct. Biol. 2:593-596, which are incorporated herein by reference).

Methods for humanising non-human antibodies are well known in the art. Generally, the humanised antibody has one or more amino acid residues introduced into it from a source which is non-human. These non-human amino acid residues, often referred to as imported residues, are typically taken from an imported variable domain. Humanisation can be essentially performed as described (see, for example, Jones et al., 1986, Nature 321:522-525; Reichmann et al., 1988. Nature 332:323-327; Verhoeyen et al., 1988, Science 239: 1534-15361; U.S. Pat. No. 4,816,567, which are incorporated herein by reference) by substituting human complementarity determining regions with corresponding rodent complementarity determining regions. Accordingly, such humanised antibodies are chimaeric antibodies, wherein substantially less than an intact human variable domain has been substituted by the corresponding sequence from a non-human species. In practice, humanised antibodies may be typically human antibodies in which some complementarity determining region residues and possibly some framework residues are substituted by residues from analogous sites in rodent antibodies.

Human antibodies can also be identified using various techniques known in the art, including phage display libraries (see, for example, Hoogenboom & Winter, 1991, J. Mol. Biol. 227:381; Marks et al., 1991, J. Mol. Biol. 222:581; Cole et al., 1985, In: Monoclonal antibodies and Cancer Therapy, Alan R. Liss, pp. 77; Boerner et al., 1991. J. Immunol. 147:86-95, Soderlind et al., 2000, Nat Biotechnol 18:852-6 and WO 98/32845 which are incorporated herein by reference).

Once suitable antibodies are obtained, they may be tested for activity, such as binding specificity or a biological activity of the antibody, for example by ELISA, immunohistochemistry, flow cytometry, immunoprecipitation, Western blots, etc. The biological activity may be tested in different assays with readouts for that particular feature.

It will be appreciated by persons skilled in the art that the binding specificity of an antibody or antigen binding fragment thereof is conferred by the presence of Complementarity Determining Regions (CDRs) within the variable regions of the constituent heavy and light chains.

The variable heavy ($V_H$) and variable light ($V_L$) domains of the antibody are involved in antigen recognition, a fact first recognised by early protease digestion experiments. Further confirmation was found by "humanisation" of rodent antibodies. Variable domains of rodent origin may be fused to constant domains of human origin such that the resultant antibody retains the antigenic specificity of the rodent-parented antibody (Morrison et al (1984) Proc. Natl. Acad. Sci. USA 81, 6851-6855).

Antigenic specificity is conferred by variable domains and is independent of the constant domains, as known from experiments involving the bacterial expression of antibody fragments, all containing one or more variable domains. These molecules include Fab-like molecules (Better et al (1988) Science 240, 1041); Fv molecules (Skerra et al (1988) Science 240, 1038); single-chain Fv (ScFv) molecules where the $V_H$ and $V_L$ partner domains are linked via a flexible oligopeptide (Bird et al (1988) Science 242, 423; Huston et al (1988) Proc. Natl. Acad. Sci. USA 85, 5879) and single domain antibodies (dAbs) comprising isolated V domains (Ward et al (1989) Nature 341, 544). A general review of the techniques involved in the synthesis of antibody fragments which retain their specific binding sites is to be found in Winter & Milstein (1991) Nature 349, 293-299.

Thus, by "antigen-binding fragment" we include functional fragments of an antibody that is capable of binding to its ligand.

Exemplary antigen-binding fragments of the invention may be selected from the group consisting of Fv fragments (e.g. single chain Fv and disulphide-bonded Fv), and Fab-like fragments (e.g. Fab fragments, Fab' fragments and F(ab)₂ fragments).

In a preferred embodiment, the antigen-binding fragment is an scFv.

The advantages of using antibody fragments, rather than whole antibodies, are several-fold. The smaller size of the fragments may lead to improved pharmacological properties, such as better penetration of solid tissue. Moreover, antigen-binding fragments such as Fab, Fv, ScFv and dAb antibody fragments can be expressed in and secreted from *E. coli* or yeast, thus allowing the facile production of large amounts of the said fragments.

Also included within the scope of the invention are modified versions of antibodies and an antigen-binding fragments thereof, e.g. modified by the covalent attachment of polyethylene glycol or other suitable polymer.

Methods of generating antibodies and antibody fragments are well known in the art. For example, antibodies may be generated via any one of several methods which employ induction of in vivo production of antibody molecules, screening of immunoglobulin libraries (Orlandi. et al, 1989. *Proc. Natl. Acad. Sci. U.S.A.* 86:3833-3837; Winter et al., 1991, *Nature* 349:293-299) or generation of monoclonal antibody molecules by cell lines in culture. These include, but are not limited to, the hybridoma technique, the human B-cell hybridoma technique, and the Epstein-Barr virus (EBV)-hybridoma technique (Kohler et al., 1975. *Nature* 256:4950497; Kozbor et al., 1985. *J. Immunol. Methods* 81:31-42; Cote et al., 1983. *Proc. Natl. Acad. Sci. USA* 80:2026-2030; Cole et al., 1984. *Mol. Cell. Biol.* 62:109-120).

The antibody or antigen-binding fragment or derivative thereof may be produced by recombinant means.

Preferably, the antibody is a monoclonal antibody.

Suitable monoclonal antibodies to selected antigens may be prepared by known techniques, for example those disclosed in "*Monoclonal Antibodies: A manual of techniques*", H Zola (CRC Press, 1988) and in "*Monoclonal Hybridoma Antibodies: Techniques and Applications*", J G R Hurrell (CRC Press, 1982), which are incorporated herein by reference.

Antibody fragments can also be obtained using methods well known in the art (see, for example, Harlow & Lane, 1988, "*Antibodies: A Laboratory Manual*", Cold Spring Harbor Laboratory, New York, which is incorporated herein by reference). For example, antibody fragments according to the present invention can be prepared by proteolytic hydrolysis of the antibody or by expression in *E. coli* or mammalian cells (e.g. Chinese hamster ovary cell culture or other protein expression systems) of DNA encoding the fragment. Alternatively, antibody fragments can be obtained by pepsin or papain digestion of whole antibodies by conventional methods. Alternatively, antibody fragments can be obtained by cell-free in vitro expression, as is known in the art.

In an alternative or additional embodiment the antibody or antigen binding fragment comprises a framework region sequence consisting of:

```
(4C8 anti-CD34 antibody heavy chain constant
region)
                                    SEQ ID NO: 1
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK (4C8 anti-CD34 antibody light chain constant
region)
                                    SEQ ID NO: 2
TVAAPSVFIFPPSDEQLKSGTASVVCLLNNFYPREAKVQWKVDNALQSGN

SQESVTEQDSKDSTYSLSSTLTLSKADYEKHKVYACEVTHQGLSSPVTKS

FNRGEC (anti-CD34-HC-anti-CD3-scFv heavy chain constant
region)
                                   SEQ ID NO: 64
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPGK
```

In an alternative or additional embodiment a binding moiety with specificity for hematopoietic stem cells and/or hematopoietic progenitor cells comprises one or more CDR sequences selected from the group consisting of:

```
SEQ ID NO: 3 (4C8 anti-CD34 antibody heavy chain
CDR1):
GYTFTNYGMN;

SEQ ID NO: 4 (4C8 anti-CD34 antibody heavy chain
CDR2:
WINTNTGEPKYAEEFKG;

SEQ ID NO: 5 (4C8 anti-CD34 antibody heavy chain
CDR3):
GYGNYARGAWLAY;

SEQ ID NO: 6 (4C8 anti-CD34 antibody light chain
CDR1):
RSSQTIVHSNGNTYLE;

(4C8 anti-CD34 antibody light chain CDR2):
QVSNRFS;
and (4C8 anti-CD34 antibody light chain CDR3):
FQGSHVPRT.
```

The term 'amino acid' as used herein includes the standard twenty genetically-encoded amino acids and their corresponding stereo-isomers in the 'D' form (as compared to the natural 'L' form), omega-amino acids other naturally-occurring amino acids, unconventional amino acids (e.g. α,α-disubstituted amino acids, N-alkyl amino acids, etc.) and chemically derivatised amino acids (see below).

When an amino acid is being specifically enumerated, such as 'alanine' or 'Ala' or 'A', the term refers to both L-alanine and D-alanine unless explicitly stated otherwise. Other unconventional amino acids may also be components of polypeptide sequences defined herein, as long as the desired functional property is retained by the polypeptide sequence. For the polypeptide sequences shown herein, each encoded amino acid residue, where appropriate, is represented by a single letter designation, corresponding to the trivial name of the conventional amino acid.

In one embodiment, the polypeptides of the invention comprise or consist of L-amino acids.

By "retains the binding specificity" we mean that the antibody or antigen-binding fragment, or variant, fusion or derivative thereof, is capable of competing for binding to its target ligand with one or more of the exemplary antibodies for the target/epitope in question.

By "capable of competing" for binding to a target ligand we mean that the tested antibody, antigen-binding fragment, variant, fusion or derivative thereof is capable of inhibiting or otherwise interfering, at least in part, with the binding of an antibody molecule with one or more of the exemplary antibodies for the target/epitope in question.

In an alternative or additional embodiment a binding moiety with specificity for hematopoietic stem cells and/or hematopoietic progenitor cells comprises a heavy chain variable region comprising or consisting of the amino acid sequence of:

(a) SEQ ID NO: 14 (4C8 anti-CD33 antibody heavy chain):
QIQLVQSGSELKKPGASVKVSCKASGYTFTNYGMNWVRQAPGQGLKWMGW
INTNTGEPKYAEEFKGRFALSLDTSVSTAYLQINSLKAEDTAVYFCARGY
GNYARGAWLAYWGQGTLVTVSS (b) SEQ ID NO: 15 (mMy10 anti-CD34 antibody heavy chain):
EVQLVESGGGLVQPGGSLRLSCAVSGFSLTSHGVHWVRQAPGKGLEWLGV
IWGAGRTDYNAAFISRLSISRDISKSQVYLQMNSLRAEDTAVYYCARNRY
ESYFDYWGQGTLVTVSS (c) SEQ ID NO: 16 (202 anti-CD133 antibody heavy chain 47):
LEVKLVESGPELKKPGETVKISCKASGYTFTDYSMHWVNQAPGKGLKWMG
WINTETGEPSYADDFKGRFAFSLETSASTAYLQINNLKNEDTATYFCATD
YGDYFDYWGQGTTLTVSSAKTTPPSVTSGQ;

(d) SEQ ID NO: 17 (202 anti-CD133 antibody heavy chain 48):
LEVKLVESGPELKKPGETVKISCKASGYTFTDYSMHWVNQAPGKGLKWMG
WINTETGEPSYADDFKGRFAFSLETSASTAYLQINNLKNEDTATYFCATD
YGDYFDYWGQGTTLTVSSAKTTPPSVTSGQAGQ;

(e) SEQ ID NO: 18 (202 anti-CD133 antibody heavy chain 49):
PEVMLVESGPELKKPGETVKISCKASGYTFTDYSMHWVNQAPGKGLKWMG
WINTETGEPSYADDFKGRFAFSLETSASTAYLQINNLKNEDTATYFCATD
YGDYFDYWGQGTTLTVSSAKTTPPSVTSGQAGQ;

(f) SEQ ID NO: 19 (202 anti-CD133 antibody heavy chain 50):
LEVKLVESGPLKKPGETVKISCKASGYTFTDYSMHWVNQAPGKGLKWMG
WINTETGEPSYADDFKGRFAFSLETSASTAYLQINNLKNEDTATYFCATD
YGDYFDYWGQGTTLTVSSAKTTPPSVTSGQAGQ;

(g) SEQ ID NO: 20 (202 anti-CD133 antibody heavy chain 51):
LEVHLVESGPELKKPGETVKISCKASGYTFTDYSMHWVNQAPGKGLKWM
GWINTETGEPSYADDFKGRFAFSLETSASTAYLQINNLKNEDTATYFCA
TDYGDYFDYWGQGTTLTVSSAKTTPPSVTSGQAGQ;

(h) SEQ ID NO: 21 (202 anti-CD133 antibody heavy chain 52):
LEVKLVESGPELKKPGETVKISCKASGYTFTDYSMHWVNQAPGKGLKWM
GWINTETGEPSYADDFKGRFAFSLETSASTAYLQINNLKNEDTATYFCA
TDCGDYFDYWGQGTTLTVSSAKTTPPSVTSGQAGQ;

(i) SEQ ID NO: 22 (202 anti-CD133 antibody heavy chain 53):
LEVKLVESGPELKKPGETVKISCKASGYTFTDYSMHWVNQAPGKGLKWMG
WINTETGEPSYADDFKGRFAFSLETSASTAYLQINNLKNEDTATYFCATD
YGDYFDYWGQGTTLTVSSAKTTPPSVTSGQAGQ;

(j) SEQ ID NO: 23 (202 anti-CD133 antibody heavy chain 54):
LEVKLVESGPELKKPGETVKISCKASGYTFTDYSMHWVNQAPGKGLKWMG
WINTETGEPSYADDFKGRFAFSLETSASTAYLQINNLKNEDTATYFCATD
YGDYFDYWGQGTTLTVSSAKTTAPSVTSGQAGQ;
or (k) SEQ ID NO: 24 (202 anti-CD133 antibody heavy chain 55):
LEVQLVESGPELKKPGETVKISCKASGYTFTDYSMHWVNQAPGKGLKWMG
WINTETGEPSYADDFKGRFAFSLETSASTAYLQINNLKNEDTATYFCATD
YGDYFDYWGQGTTLTVSSAKTTAPSVTSGQAGQ.

In an alternative or additional embodiment a binding moiety with specificity for hematopoietic stem cells and/or hematopoietic progenitor cells comprises a light chain variable region comprising or consisting of the amino acid sequence of:

(a) SEQ ID NO: 25 (4C8 anti-CD34 antibody light chain):
DVLLTQSPLSLPVTLGQPASISCRSSQTIVHSNGNTYLEWFQQRPGQSPRLLIYQVSNRFSGVPDRFSGSGS
GTDFTLKISRVEAEDVGVYYCFQGSHVPRTFGGGTKVEIKRTVAAPSVFIFPPSDEQLKSGTASVVCLLNNF
YPREAKVQWKVDNALQSGNSQESVTEQDSKDSTYSLSSTLTLSKADYEKHKVYACEVTHQGLSSPVTKSFNR
GEC -continued (b) SEQ ID NO: 26 (mMY10 anti-CD34 antibody light chain):
DIQMTQSPSSLSASVGDRVTITCRSSQNLVHSNGNTYLHWYQQKPGKAPKLLIYKVSNRFSGVPDRFSGSGS

GTEFTLTISSLQPEDFATYYCSQSTHVPLTFGQGTKVEIKR (c) SEQ ID NO: 27 (202 anti-CD133 antibody light chain 47):
AQAAELDIVLTQSPAIMSASPGEKVTISCSASSSVGYMYWYQQKPGSSPKPWIYRPSNLASGVPARFSGSGS

GTSYSLTISSMEAEDAATYYCQQYHSYFFTFGAGTKLELK (d) SEQ ID NO: 28 (202 anti-CD133 antibody light chain 48):
AQAAELDIVLTQSPAIMSASPGEKVTISCSASSSVSYMYWYQQKPGSSPKPWIYRTSNLASGVPARFSG

SGSGTSYSLTISSMEAEDAATYYCQQYHSYPPTFGAGTKLELK (e) SEQ ID NO: 29 (202 anti-CD133 antibody light chain 49):
AQAAELDIVLTQSPAIMSASPGEKVTISCSASSSVSYMYWYQQKPGSSPKPWIYRPSNLASGVPARFSGSGSGTS

YSLTISSMEAEDAATYYCQQYHSYPPTFGAGTKLELK (f) SEQ ID NO: 30 (202 anti-CD133 antibody light chain 50):
AQAAELDIVLTQSPAIMSASPGEKVTISCSASSSVSYMYWYQQKPGQPPRLLTYLVSNLESGVPARFSGSGSGTD

FTLNIHPVEEEDAATYYCQQYHSYPPTFGAGTKLEIK (g) SEQ ID NO: 31 (202 anti-CD133 antibody light chain 51):
AQAAELDIVLTQSPAIMSASPGEKVTISCSASSSVSYMYWYQQKPGSSPKPWIYRPSNLASGVPARFSGSGSGTS

YSLTISSMEAEDAATYYCQQYHSYPPTFGAGTKLELK (h) SEQ ID NO: 32 (202 anti-CD133 antibody light chain 52):
AQAAELDIVLSQSPAIMSASPGEKVTISCSASSSVSYMYWYQQKPGSPPKPWIYRTSNLASGVPARFSGSGSGTS

YSLTISSMEAEDAATYYCQQYHSYPPTFGAGTKLELK (i) SEQ ID NO: 33 (202 anti-CD133 antibody light chain 53):
AQAAELDIVLSQSPAIMSASPGEKVTISCSASSSVSYMYWYQQKPGSSPKPWIYRTSNLASGVPARFSGSGSGTS

YSLTISSMEAEDAATYYCQQYHSYPPTFGAGTKLELK (j) SEQ ID NO: 34 (202 anti-CD133 antibody light chain 54):
AQAAELDIVLTQSPAIMSASPGEKVTISCSASSSVSYMYWYQQKPGSSPKPWIYRPSNLASGVPARFSGSGSGTS

YSLTISSMEAEDAATYYCQQYHSYPPTFGAGTKLELK (k) SEQ ID NO: 35 (202 anti-CD133 antibody light chain 55):
AQAAELDIVLTQSPAIMSASPGEKVTISCSASSSVSYMYWYQQKPGSSPKPWIYRPSNLASGVPARFSGSGSGTS

YSLTISSMEAEDAATYYCQQYHSYPPTFGAGTKLELK

In an alternative or additional embodiment the antibody, antigen-binding fragment, variant, fusion or derivative thereof comprises a heavy chain variable region as defined above and a light chain variable region as defined above, or variants, derivatives or fusions thereof that retain, at least in part, the ability to bind to their target antigen.

As defined herein, the binding moiety may be a variant, fusion or derivative thereof of an antibody or antigen-binding fragment, provided such variants, fusions and derivatives retain binding specificity for the ligand of the parent antibody.

Variants may be made using the methods of protein engineering and site-directed mutagenesis well known in the art using the recombinant polynucleotides (see example, see *Molecular Cloning: a Laboratory Manual,* 3rd edition, Sambrook & Russell, 2001, Cold Spring Harbor Laboratory Press, which is incorporated herein by reference).

By 'variants' of the antibody or antigen-binding fragment of the invention we include insertions, deletions and substitutions, either conservative or non-conservative. In particular we include variants of the sequence of the antibody or antigen-binding fragment where such variations do not substantially alter the activity of the antibody or antigen-binding fragment. In particular, we include variants of the antibody or antigen-binding fragment where such changes do not substantially alter the binding specificity for its ligand.

The polypeptide variant may have an amino acid sequence which has at least 70% identity with one or more of the amino acid sequences of the antibody or antigen-binding fragment of the invention as defined herein—for example, at least 75%, at least 80%, at least 90%, at least 95%, at least 96%, at least 97%, at least 98%, or at least 99% identity with one or more of the amino acid sequences of the antibody or antigen-binding fragment of the invention as defined herein.

The percent sequence identity between two polypeptides may be determined using suitable computer programs, for example the GAP program of the University of Wisconsin Genetic Computing Group and it will be appreciated that percent identity is calculated in relation to polypeptides whose sequences have been aligned optimally.

The alignment may alternatively be carried out using the Clustal W program (as described in Thompson et al., 1994, *Nucl. Acid Res.* 22:4673-4680, which is incorporated herein by reference).

The parameters used may be as follows:

Fast pair-wise alignment parameters: K-tuple(word) size; 1, window size; 5, gap penalty; 3, number of top diagonals; 5. Scoring method: x percent.

Multiple alignment parameters: gap open penalty; 10, gap extension penalty; 0.05.

Scoring matrix: BLOSUM.

Alternatively, the BESTFIT program may be used to determine local sequence alignments.

The antibody or antigen-binding fragment, variant, fusion or derivative of the invention may comprise one or more amino acids which have been modified or derivatised.

Chemical derivatives of one or more amino acids may be achieved by reaction with a functional side group. Such derivatised molecules include, for example, those molecules in which free amino groups have been derivatised to form amine hydrochlorides, p-toluene sulphonyl groups, carboxybenzoxy groups, t-butyloxycarbonyl groups, chloroacetyl groups or formyl groups. Free carboxyl groups may be derivatised to form salts, methyl and ethyl esters or other types of esters and hydrazides. Free hydroxyl groups may be derivatised to form O-acyl or O-alkyl derivatives. Also included as chemical derivatives are those peptides which contain naturally occurring amino acid derivatives of the twenty standard amino acids. For example: 4-hydroxyproline may be substituted for proline; 5-hydroxylysine may be substituted for lysine; 3-methylhistidine may be substituted for histidine; homoserine may be substituted for serine and ornithine for lysine. Derivatives also include peptides containing one or more additions or deletions as long as the requisite activity is maintained. Other included modifications are amidation, amino terminal acylation (e.g. acetylation or thioglycolic acid amidation), terminal carboxylamidation (e.g. with ammonia or methylamine), and the like terminal modifications.

It will be further appreciated by persons skilled in the art that peptidomimetic compounds may also be useful. Thus, the present invention includes peptidomimetic compounds which are capable of binding to target ligands. The term 'peptidomimetic' refers to a compound that mimics the conformation and desirable features of a particular peptide as a therapeutic agent.

For example, the antibody, antigen-binding fragment, variant, fusion or derivative thereof of the invention include not only molecules in which amino acid residues are joined by peptide (—CO—NH—) linkages but also molecules in which the peptide bond is reversed. Such retro-inverso peptidomimetics may be made using methods known in the art, for example such as those described in Meziere et al. (1997) *J. Immunol.* 159, 3230-3237, which is incorporated herein by reference. This approach involves making pseudopeptides containing changes involving the backbone, and not the orientation of side chains. Retro-inverse peptides, which contain NH—CO bonds instead of CO—NH peptide bonds, are much more resistant to proteolysis. Alternatively, the antibody, antigen-binding fragment, variant, fusion or derivative thereof of the invention may be a peptidomimetic compound wherein one or more of the amino acid residues are linked by a -y(CH$_2$NH)— bond in place of the conventional amide linkage.

In a further alternative, the peptide bond may be dispensed with altogether provided that an appropriate linker moiety which retains the spacing between the carbon atoms of the amino acid residues is used; it may be advantageous for the linker moiety to have substantially the same charge distribution and substantially the same planarity as a peptide bond.

It will be appreciated that the antibody, antigen-binding fragment, variant, fusion or derivative thereof of the invention may conveniently be blocked at its N- or C-terminus so as to help reduce susceptibility to exo-proteolytic digestion.

A variety of un-coded or modified amino acids such as D-amino acids and N-methyl amino acids have also been used to modify mammalian peptides. In addition, a presumed bioactive conformation may be stabilised by a covalent modification, such as cyclisation or by incorporation of lactam or other types of bridges, for example see Veber et al., 1978, *Proc. Natl. Acad. Sci. USA* 75:2636 and Thursell et al., 1983, *Biochem. Biophys. Res. Comm.* 111:166, which are incorporated herein by reference.

A common theme among many of the synthetic strategies has been the introduction of some cyclic moiety into a peptide-based framework. The cyclic moiety restricts the conformational space of the peptide structure and this frequently results in an increased specificity of the peptide for a particular biological receptor. An added advantage of this strategy is that the introduction of a cyclic moiety into a peptide may also result in the peptide having a diminished sensitivity to cellular peptidases.

Thus, exemplary antibody, antigen-binding fragment, variant, fusion or derivative thereof of the invention may comprise terminal cysteine amino acids. Such polypeptides may exist in a heterodetic cyclic form by disulphide bond formation of the mercaptide groups in the terminal cysteine amino acids or in a homodetic form by amide peptide bond formation between the terminal amino acids. As indicated above, cyclising small peptides through disulphide or amide bonds between the N- and C-terminus cysteines may circumvent problems of specificity and half-life sometime observed with linear peptides, by decreasing proteolysis and also increasing the rigidity of the structure, which may yield higher specificity compounds. Polypeptides cyclised by disulphide bonds have free amino and carboxy-termini which still may be susceptible to proteolytic degradation, while peptides cyclised by formation of an amide bond between the N-terminal amine and C-terminal carboxyl and hence no longer contain free amino or carboxy termini. Thus, peptides can be linked either by a C—N linkage or a disulphide linkage.

The present invention is not limited in any way by the method of cyclisation of peptides, but encompasses peptides whose cyclic structure may be achieved by any suitable method of synthesis. Thus, heterodetic linkages may include, but are not limited to formation via disulphide, alkylene or sulphide bridges. Methods of synthesis of cyclic homodetic peptides and cyclic heterodetic peptides, including disulphide, sulphide and alkylene bridges, are disclosed in U.S. Pat. No. 5,643,872, which is incorporated herein by reference. Other examples of cyclisation methods are discussed and disclosed in U.S. Pat. No. 6,008,058, which is incorporated herein by reference.

A further approach to the synthesis of cyclic stabilised peptidomimetic compounds is ring-closing metathesis (RCM). This method involves steps of synthesising a peptide precursor and contacting it with an RCM catalyst to yield a conformationally restricted peptide. Suitable peptide precursors may contain two or more unsaturated C—C bonds. The method may be carried out using solid-phase-peptide-synthesis techniques. In this embodiment, the precursor, which is anchored to a solid support, is contacted with a RCM catalyst and the product is then cleaved from the solid support to yield a conformationally restricted peptide.

Another approach, disclosed by D. H. Rich in Protease Inhibitors, Barrett and Selveson, eds., Elsevier (1986), which is incorporated herein by reference, has been to design peptide mimics through the application of the transition state analogue concept in enzyme inhibitor design. For example, it is known that the secondary alcohol of staline mimics the tetrahedral transition state of the scissile amide bond of the pepsin substrate.

In summary, terminal modifications are useful, as is well known, to reduce susceptibility by proteinase digestion and therefore to prolong the half-life of the peptides in solutions, particularly in biological fluids where proteases may be present. Polypeptide cyclisation is also a useful modification because of the stable structures formed by cyclisation and in view of the biological activities observed for cyclic peptides.

By 'fusion' we include an antibody or antigen-binding fragment (as defined herein) fused to any other polypeptide. For example, the antibody or antigen-binding fragment may be fused to a polypeptide such as glutathione-S-transferase (GST) or protein A in order to facilitate its purification. Examples of such fusions are well known to those skilled in the art. Similarly, the said antibody or antigen-binding fragment may be fused to an oligo-histidine tag such as His6 or to an epitope recognised by a further antibody (such as the well-known Myc tag epitope).

The fusion may comprise a further portion which confers a desirable feature on the antibody or antigen-binding fragment of the invention; for example, the portion may be useful in detecting or isolating the antibody or antigen-binding fragment, or promoting cellular uptake of the antibody or antigen-binding fragment. The portion may be, for example, a biotin moiety, a radioactive moiety, a fluorescent moiety, for example a small fluorophore or a green fluorescent protein (GFP) fluorophore, as well known to those skilled in the art. The moiety may be an immunogenic tag, for example a Myc tag, as known to those skilled in the art, or may be a lipophilic molecule or polypeptide domain that is capable of promoting cellular uptake, as known to those skilled in the art.

Methods for conjugating additional moieties to an antibody (or a fusion, variant or derivative thereof) are well known in the art. Exemplary methods are described in Bioconjugate Techniques, 2nd Edition (2008); Hermanson (Academic Press, Inc.) and in Veronese et al., (1999; Farmaco 54(8): 497-516); Stayton et al., (2005; Orthod Craniofac Res 8(3): 219-225); Schrama et al., (2006; Nat Rev Drug Discov 5(2): 147-159); Doronina et al. (2003; Nat Biotechnol 21(7): 778-784); Carter et al., (2008; Cancer J 14(3): 154-169); Torchilin (2006; Annu Rev Biomed Eng 8: 343-375); Rihova (1998; Adv Drug Deliv Rev 29(3): 273-289); Goyal et al. (2005; Acta Pharm 55(1): 1-25); Chari (1998; Adv Drug Deliv Rev 31(1-2): 89-104); Garnett (2001; Adv Drug Deliv Rev 53(2): 171-216); Allen (2002; Nat Rev Cancer 2(10): 750-763).

In an alternative aspect, the invention provides an agent according wherein the binding moiety is an antibody mimic (such as a non-antibody scaffold).

It will be appreciated that antibody mimics (for example, non-antibody scaffold structures that have a high degree of stability yet allow variability to be introduced at certain positions) may be used to create molecular libraries from which binding moieties can be derived. Those skilled in the arts of biochemistry will be familiar with many such molecules. Such molecules may be used as a binding moiety in the agent of the present invention.

Exemplary antibody mimics are discussed in Skerra et al. (2007, Curr. Opin. Biotech., 18: 295-304) and include: affibodies (also called Trinectins; Nygren, 2008, FEBS J, 275, 2668-2676); CTLDs (also called Tetranectins; *Innovations Pharmac. Technol.* (2006), 27-30); adnectins (also called monobodies; *Meth. Mol. Biol.*, 352 (2007), 95-109); anticalins (*Drug Discovery Today* (2005), 10, 23-33); DARPins (ankyrins; *Nat. Biotechnol.* (2004), 22, 575-582); avimers (*Nat. Biotechnol.* (2005), 23, 1556-4561); microbodies (*FEBS J*, (2007), 274, 86-95); peptide aptamers (*Expert. Opin. Biol. Ther.* (2005), 5, 783-797); Kunitz domains (*J. Pharmacol. Exp. Ther.* (2006) 318, 803-809); affilins (*Trends. Biotechnol.* (2005), 23, 514-522).

Accordingly, it is preferred that the antibody mimic is selected from the group comprising or consisting of affibodies, tetranectins (CTLDs), adnectins (monobodies), anticalins, DARPins (ankyrins), avimers, iMabs, microbodies, peptide aptamers, Kunitz domains and affilins.

In a further aspect, the invention provides an agent wherein the binding moiety is an RNA aptamer.

RNA aptamers represent a unique emerging class of therapeutic agents (Que-Gewirth et al, Gene Ther. 74:283 (2007); Ireson et al, MoI. Cancer Ther. 5:2957 (2006)). They are relatively short (12-30 nucleotide) single-stranded RNA oligonucleotides that assume a stable three-dimensional shape to tightly and specifically bind selected protein targets to elicit a biological response. In contrast to antisense oligonucleotides, RNA aptamers can effectively target extracellular targets. Like antibodies, aptamers possess binding affinities in the low nanomolar to picomolar range. In addition, aptamers are heat stable, non-immunogenic, and possess minimal inter-batch variability. Chemical modifications, such as amino or fluoro substitutions at the 2' position of pyrimidines, may reduce degradation by nucleases. The biodistribution and clearance of aptamers can also be altered by chemical addition of moieties such as polyethylene glycol and cholesterol.

Aptamers may be developed by iterative selection methods such as SELEX (systematic evolution of ligands by exponential enrichment) to specifically recognize and tightly bind their targets by means of well-defined complementary three-dimensional structures. Further, SELEX (and other such methods) allows selection from libraries to generate high-affinity oligonucleotide ligands to purified biochemical targets. Recently, the aptamer pegaptanib was approved for the treatment of age-related macular degeneration (Wong et al, Lancet 370:204 (2007)). With regard to the field of oncology, the DNA aptamer GBI-10, derived from a human glioblastoma cell line, was recently demonstrated to bind tenascin-C (Daniels et al, Proc. Natl Acad. ScL USA 100: 15416 (2003)). Similarly, RNA aptamers have been demonstrated to target the Ku DNA repair proteins with resulting sensitization of breast cancer cells to etoposide (Zhang et al, Int. J. Mol. Med. 74:153 (2004)).

In a further aspect, the invention provides an agent wherein the binding moiety is a small molecule.

By "small molecule" we mean a low molecular weight organic compound of 900 Daltons or less. Although large biopolymers such as nucleic acids, proteins, and polysaccharides (such as starch or cellulose) are not included as "small molecules", their constituent monomers (ribo- or deoxyribonucleotides, amino acids, and monosaccharides, respectively) and oligomers (i.e. short polymers such as dinucleotides, peptides such as the antioxidant glutathione, and disaccharides such as sucrose) are included.

The production of small molecules is described in Mayes & Whitcombe, 2005, *Adv. Drug Deliv. Rev.* 57:1742-78 and Root-Bernstein & Dillon, 2008, *Curr. Pharm. Des.* 14:55-62.

It is preferred that, where the binding moiety is an antibody mimic, RNA aptamer or small molecule, the agent of the invention is in an isolated and/or purified form.

Preferably, the agent of the invention further comprises a detectable moiety.

By a "detectable moiety" we include the meaning that the moiety is one which, when located at the target site following administration of an agent of the invention to a patient, may be detected, typically non-invasively from outside the body and the site of the target located.

The detectable moiety may be a single atom or molecule which is either directly or indirectly involved in the production of a detectable species. Thus, the agents of this embodiment of the invention are useful in imaging and diagnosis.

Suitable detectable moieties are well known in medicinal chemistry and the linking of these moieties to polypeptides and proteins is well known in the art. Examples of detectable moieties include, but are not limited to, the following: radioisotopes (e.g. $^3$H, $^{14}$C, $^{35}$S, $^{123}$I, $^{125}$I, $^{131}$I, $^{99}$Tc, 111In, $^{90}$Y, $^{188}$Re), radionuclides (e.g. $^{11}$C, $^{18}$F, $^{64}$Cu), fluorescent labels (e.g. FITC, rhodamine, lanthanide phosphors, carbocyanine), enzymatic labels (e.g. horseradish peroxidase, β-galactosidase, luciferase, alkaline phosphatase), chemiluminescent, biotinyl groups and predetermined polypeptide epitopes recognised by a secondary reporter (e.g. leucine zipper pair sequences, binding sites for secondary antibodies, metal binding domains, epitope tags). In some embodiments, labels are attached by spacer arms of various lengths to reduce potential steric hindrance.

Preferably, the detectable moiety comprises a radioactive atom, such as a radioactive atom selected from the group consisting of: technetium-99; technitium-99m; iodine-123; iodine-124; iodine-131; indium-111; fluorine-18; fluorine-19; carbon-11; carbon-13; copper-64; nitrogen-13; nitrogen-15; oxygen-15; oxygen-17; arsenic-72; gadolinium; manganese; iron; deuterium; tritium; yttrium-86; zirconium-89.

The radio- or other labels may be incorporated into the agents of the invention in known ways. For example, if the binding moiety is a polypeptide it may be biosynthesised or may be synthesised by chemical amino acid synthesis using suitable amino acid precursors involving, for example, fluorine-19 in place of hydrogen. Labels such as $^{99m}$Tc, $^{123}$I, $^{186}$Rh, $^{188}$Rh and $^{111}$In can, for example, be attached via cysteine residues in the binding moiety. Yttrium-90 can be attached via a lysine residue. The IODOGEN method (Fraker et al (1978) *Biochem. Biophys. Res. Comm.* 80, 49-57, which is incorporated herein by reference) can be used to incorporate $^{123}$I. Reference ("Monoclonal Antibodies in Immunoscintigraphy", J-F Chatal, CRC Press, 1989, which is incorporated herein by reference) describes other methods in detail.

In an alternative or additional embodiment a binding moiety with specificity for one or more type of effector cell comprises one or more CDR sequences selected from the group consisting of:

(1252 anti-CD3 antibody heavy chain CDR1):
GFTFDDYT;

(1268 anti-CD3 antibody heavy chain CDR1):
GFTFDDFT;

(1284 anti-CD3 antibody heavy chain CDR1):
GFTFDDYT;

(1300 anti-CD3 antibody heavy chain CDR1):
GFTFRSYA;

(1316 anti-CD3 antibody heavy chain CDR1):
GFTFRSYG;

(1330 anti-CD3 antibody heavy chain CDR1):
GYTFTRYT;

(1254 anti-CD3 antibody heavy chain CDR2):
ISWNSGSI;

(1270 anti-CD3 antibody heavy chain CDR2):
ISWNSGSI;

(1286 anti-CD3 antibody heavy chain CDR2):
ISWNSGSI;

(1302 anti-CD3 antibody heavy chain CDR2):
VYYDGNNQ;

(1318 anti-CD3 antibody heavy chain CDR2):
IYYDGKNK;

(1331 anti-CD3 antibody heavy chain CDR2):
INPSRGYT;

SEQ ID NO: 36 (1256 anti-CD3 antibody heavy chain CDR3):
AKDNSGYGHYYYGMDV;

SEQ ID NO: 37 (1272 anti-CD3 antibody heavy chain CDR3):
AKDNSGYGYYYGMDV;

SEQ ID NO: 48 (1288 anti-CD3 antibody heavy chain CDR3):
AKDNSGYGHYYYGMDV;

SEQ ID NO: 39 (1304 anti-CD3 antibody heavy chain CDR3):
ARGPGYNWLDP;

SEQ ID NO: 40 (1320 anti-CD3 antibody heavy chain CDR3):
ARGPGYNWLDP;

SEQ ID NO: 41 (1332 anti-CD3 antibody heavy chain CDR3):
ARYYDDHYCLDY;

(1260 anti-CD3 antibody light chain CDR1):
QSVSSN;

(1276 anti-CD3 antibody light chain CDR1):
HSVSRN;

(1292 anti-CD3 antibody light chain CDR1):
QSVSSN;

(1308 anti-CD3 antibody light chain CDR1):
QSVSRN;

(1324 anti-CD3 antibody light chain CDR1):
QRISSN;

SEQ ID NO: 44 (1334 anti-CD3 antibody light chain CDR1):
LSCRASQSVSY;

(1262 anti-CD3 antibody light chain CDR2):
GAS;

(1335 anti-CD3 antibody light chain CDR2):
DTS;

(1264 anti-CD3 antibody light chain CDR3):
QHYINWPLT;

(1280 anti-CD3 antibody light chain CDR3):
QQYNNWPLT;

(1296 anti-CD3 antibody light chain CDR3):
QHYINWPLT;

(1312 anti-CD3 antibody light chain CDR3):
QQYNNWPLT;

(1328 anti-CD3 antibody light chain CDR3):
QQHHNWPLT;

(1336 anti-CD3 antibody light chain CDR3):
QQWSSNPLT;

In an alternative or additional embodiment a binding moiety with specificity for one or more type of effector cell comprises a heavy chain variable region comprising or consisting of the amino acid sequence of:

(a) (anti-CD3 heavy chain)
SEQ ID NO: 43
DIKLQQSGAELARPGASVKMSCKTSGYTFTRYTMHWVKQRPGQGLEWIGYINPSRGYT
NYNQKFKDKATLTTDKSSSTAYMQLSSLTSEDSAVYYCARYYDDHYCLDYWGQGTTL
TVSS;

(b) (253 anti-CD3 heavy chain)
SEQ ID NO: 44
QVQLVQSGAEVRKPGASVRVTMHWVRQAPGHGLEWIGYINPSRGYTNYNQKFKDRVT
MTTDKSFSTAIMDLRSLRSDDSAVYYCARYYDDHYCLDYWGQGTTVTVSSSCKASGYT
FTRY;

(c) (1250 anti-CD3 antibody heavy chain):
SEQ ID NO: 45
EVQLVESGGGLVQPGRSLRLSCAASGFTFDDYTMHWVRQAPGKGLEWVSGISWNSGSI
GYADSVKGRFTISRDNAKKSLYLQMNSLRAEDTALYYCAKDNSGYGHYYYGMDV;

(d) (1266 anti-CD3 antibody heavy chain):
SEQ ID NO: 46
EVQLVESGGGLVQPGGSLRLSCAATGFTFDDFTMHWVRQAPGKGLEWVSGISWNSGSI
GYVDSVKGRFTISRDNAKNSLYLQMNSLRAEDTALYYCAKDNSGYGYYYYGMDVWG
QGTTVTVSS;

(e) (1282 anti-CD3 antibody heavy chain).
SEQ ID NO: 47
EVQLVESGGGLVQPGRSLRLSCAASGFTFDDYTMHWVRQAPGKGLEWVSGISWNSGSI
GYADSVKGRFTISRDNAKKSLYLQMNSLRAEDTALYYCAKDNSGYGHYYYGMDVWG
QGTTVTVAS;

(f) (1298 anti-CD3 antibody heavy chain):
SEQ ID NO: 48
QVQLVESGGGVVQPGRSLRLSCAASGFTFRSYAMHWVRQAPGKGLEWVAMVYYDGN
NQYYADSVRGRFTISRDNSKNTLYLQMNSLRADDTAVYFCARGPGYNWLDPWGQGTL
VTVSS;

(g) (1314 anti-CD3 antibody heavy chain):
SEQ ID NO: 49
QVQLVESGGGVVQPGRSLRLACVASGFTFRSYGMHWVRQAPGKGLQWVAMIYYDGK
NKYYADSVRGRFTISRDNSKNTLYLQMNNLRVEDTAMYFCARGPGYNWLDPWGQGTL
VTVSS;
or -continued (h) (1329 anti-CD3 antibody heavy chain):
SEQ ID NO: 50
DVQLVQSGAEVKKPGASVKVSCKASGYTFTRYTMHWVRQAPGQGLEWIGYINPSRGY

TNYADSVKGRFTITTDKSTSTAYMELSSLRSEDTATYYCARYYDDHYCLDYWGQGTTV

TVSS.

In an alternative or additional embodiment a binding moiety with specificity for one or more type of effector cell comprises a light chain variable region comprising or consisting of the amino acid sequence of:

(a) (anti-CD3 light chain)
SEQ ID NO: 65
DDIQLTQSPAIMSASPGEKVTMTCRASSSVSYMNWYQQKSGTSPKRWIYDTSKVASGVP

YRFSGSGSGTSYSLTISSMEAEDAATYYCQQWSSNPLTFGAGTKLELK;

(b) (253 anti-CD3 antibody light chain)
SEQ ID NO: 51
EIVLTQSPATLSLSPGERATLSCSASSSVSYMNWYQQKPGQAPRRWIYDTSKLASGIPAR

FSGSGSGTDFTLTISSLEPEDFATYYCQQWSSNPFTFGGGTKVEIKR;

(c) (1258 anti-CD3 antibody light chain):
SEQ ID NO: 52
AEIVMTQSPATLSVSPGERATLSCRASQSVSSNLAWYQQKPGQAPRLLIYGASTRATGIP

ARFSGSGSGTEFTLTISSLQSEDFAVYYCQHYINWPLTFGGGTKVEIK;

(d) (1274 anti-CD3 antibody light chain):
SEQ ID NO: 53
EIVMTQSPATLSVSPGERATLSCRASHSVSRNSAWYQQKPGQAPRLLIYGASTRATGIPA

RFSGSGSGTEFTLTISSLQSEDFAIYYCQQYNNWPLTFGGGTKVEIK;

(e) (1290 anti-CD3 antibody light chain):
SEQ ID NO: 54
EIVMTQSPATLSVSPGERATLSCRASQSVSSNLAWYQQKPGQAPRLLIYGASTRATGIPA

RFSGSGSGTEFTLTISSLQSEDFAVYYCQHYINWPLTFGGGTKVEIK;

(f) (1306 anti-CD3 antibody light chain):
SEQ ID NO: 55
EIVMTQSPATLSVSPGERATLSCRASQSVSRNLAWYQQKPGQAPRLLIYGASTRATGIPA

RFSGSGSGTDFTLTISSLQSEDFAVYYCQQYNNWPLTFGGGTKVVIK;

(g) (1322 anti-CD3 antibody light chain):
SEQ ID NO: 56
EIVMTQSPATLSVSPGERATLSCRASQRISSNLAWYQQKPGQAPRLLIYGASTRATGSPA RFSGSGSGTDFTLTISSLQSEDVAVYYCQQHHNWPLTFGGGTKVEIK;
or (h) (1333 anti-CD3 antibody light chain):
SEQ ID NO: 57
DIVLTQSPATLSLSPGERATLSCRASQSVSYMNWYQQKPGKAPKRWIYDTSKVASGVPA

RFSGSGSGTDYSLTINSLEAEDAATYYCQQWSSNPLTFGGGTKVEIK.

In an alternative or additional embodiment, the present invention includes the use of the antibodies described in US 2010/0311955 A1, U.S. Pat. No. 7,635,472 A, U.S. Pat. No. 8,927,696 A, US 2013/224202 A, WO 11/089211 A, U.S. Pat. No. 7,635,472, US 2014/088295 and/or EP 1 394 253 and/or one or more of the CDRs, variable regions and constant regions described therein. The disclosures of these documents is incorporated herein by reference. It will be appreciated by those skilled in the art that an antibody or fragment thereof may have one, two, three, four, five or six CDRs. Preferably three CDRs from a light chain and three from a heavy chain. Preferably the CDRs from the light chain and heavy chain are from antibodies that specifically bind the same epitope. Preferably the CDRs from the light chain and heavy chain are from the same antibody.

In an alternative or additional embodiment the antibody, antigen-binding fragment, variant, fusion or derivative thereof comprises a heavy chain variable region as defined above and a light chain variable region as defined above, or variants, derivatives or fusions thereof that retain, at least in part, the ability to bind to their target antigen.

In an alternative or additional embodiment the heavy and light chain variable regions are linked by a linker which does not destroy the desired properties of the agent.

In an alternative or additional embodiment the linker is of sufficient length to enable the domains to fold in such a way as to permit binding to target antigen.

The linker may be a peptide linker. The peptide linker may comprise between 1 and 50 amino acids, for example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 amino acids. Suitable linkers may include those listed in Kola, 1999, *J. Immunol. Meth.,* 231:177 which is incorporated herein by reference.

Alternatively, the linker may be absent.

In an alternative or additional embodiment the binding moiety with specificity for hematopoietic stem cells and/or hematopoietic progenitor cells and the binding moiety with specificity for one or more type of effector cell additionally comprise:

(c) a linker linking the binding moieties.

In an alternative or additional embodiment the linker is of sufficient length to enable the domains to fold in such a way as to permit binding to target antigen and/or does not destroy the desired properties of the agent.

The linker may be a peptide linker. The peptide linker may comprise between 1 and 50 amino acids, for example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 amino acids.

In an alternative or additional embodiment the linker comprises or consists of the amino acid sequence of:

```
(a)
                                         SEQ ID NO: 58
GGGGSGGGGSGGGGS (b) (253 anti-CD3 linker 1)
                                         SEQ ID NO: 59
NSTYRVVSVLTVLHQDWLNGKEYKCK (c)(253 anti-CD3 linker 2)
                                         SEQ ID NO: 60
FQNALLVRYTKKVPQVSTPTLVEVS (d) (253 anti-CD3 linker 3)
                                         SEQ ID NO: 61
ASADDAKKDAAKKDDAKKDDAKKDL (e) (202 anti-CD133 antibody linker):
                                         SEQ ID NO: 62
SSGGGGSGGGGGGSSRSS
```

Suitable linkers may include those listed in Völkel et al., 2001, *Protein Eng.,* 14(10):815-823 which is incorporated herein by reference.

Alternatively, the linker may be absent.

In an alternative or additional embodiment the agent comprises or consists of a multi-specific antibody, for example, di-, tri-, tetra-, penta-, hexa-, hepta- or octo-specific antibody.

In an alternative or additional embodiment the multi-specific antibody is selected from the group consisting of trifunctional antibodies; bi-specific T-cell engagers (BiTEs); mAB2; duobodies; IgG-like molecules with complementary CH3 domains; recombinant IgG-like dual targeting molecules; IgG fusion molecules; Fc fusion molecules; Fab fusion molecules; ScFv- and/or diabody-based heavy chain antibodies.

In an alternative or additional embodiment the agent comprises or consists of the amino acid sequence of:

```
(f) (anti-CD34-HC-anti-CD3-scFv)
                                         SEQ ID NO: 63
QIQLVQSGSELKKPGASVKVSCKASGYTFTNYGMNWVRQAPGQGLKWMGW

INTNTGEPKYAEEFKGRFALSLDTSVSTAYLQINSLKAEDTAVYFCARGY
```

```
-continued
GNYARGAWLAYWGQGTLVTVSSASTKGPSVFPLAPSSKSTSGGTAALGCL

VKDYFPEPVTVSWNSGALTSGVHTFPAVLQSSGLYSLSSVVTVPSSSLGT

QTYICNVNHKPSNTKVDKKVEPKSCDKTHTCPPCPAPELLGGPSVFLFPP

KPKDTLMISRTPEVTCVVVDVSHEDPEVKFNWYVDGVEVHNAKTKPREEQ

YNSTYRVVSVLTVLHQDWLNGKEYKCKVSNKALPAPIEKTISKAKGQPRE

PQVYTLPPSREEMTKNQVSLTCLVKGFYPSDIAVEWESNGQPENNYKTTP

PVLDSDGSFFLYSKLTVDKSRWQQGNVFSCSVMHEALHNHYTQKSLSLSP

GKGGGGSGGGGSGGGGSDIKLQQSGAELARPGASVKMSCKTSGYTFTRYT

MHWVKQRPGQGLEWIGYINPSRGYTNYNQKFKDKATLTTDKSSSTAYMQL

SSLTSEDSAVYYCARYYDDHYCLDYWGQGTTLTVSSVEGGSGGSGGSGGS

GGVDDIQLTQSPAIMSASPGEKVTMTCRASSSVSYMNWYQQKSGTSPKRW

IYDTSKVASGVPYRFSGSGSGTSYSLTISSMEAEDAATYYCQQWSSNPLT

FGAGTKLELK
```

A second aspect of the invention provides a nucleic acid molecule encoding a polypeptide as defined in the first aspect of the invention.

In an alternative or additional embodiment the nucleic acid molecule is a DNA molecule.

In an alternative or additional embodiment the nucleic acid molecule is codon optimized (e.g., codon optimized for expression in a host cell).

A third aspect of the invention provides a vector comprising a nucleic acid molecule as defined in the second aspect of the invention.

In an alternative or additional embodiment the vector is an expression vector.

In brief, expression vectors may be constructed comprising a nucleic acid molecule which is capable, in an appropriate host, of expressing the polypeptide encoded by the nucleic acid molecule.

A variety of methods have been developed to operably link nucleic acid molecules, especially DNA, to vectors, for example, via complementary cohesive termini. For instance, complementary homopolymer tracts can be added to the DNA segment to be inserted into the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. The DNA segment, e.g. generated by endonuclease restriction digestion, is treated with bacteriophage T4 DNA polymerase or *E. coli* DNA polymerase I, enzymes that remove protruding, 3'-single-stranded termini with their 3'-5'-exonucleolytic activities, and fill in recessed 3'-ends with their polymerising activities.

The combination of these activities therefore generates blunt-ended DNA segments. The blunt-ended segments are then incubated with a larger molar excess of linker molecules in the presence of an enzyme that is able to catalyse the ligation of blunt-ended DNA molecules, such as bacteriophage T4 DNA ligase. Thus, the products of the reaction are DNA segments carrying polymeric linker sequences at their ends. These DNA segments are then cleaved with the appropriate restriction enzyme and ligated to an expression vector that has been cleaved with an enzyme that produces termini compatible with those of the DNA segment.

Synthetic linkers containing a variety of restriction endonuclease site are commercially available from a number of sources including International Biotechnologies Inc., New Haven, Conn., USA.

A desirable way to modify the DNA encoding the polypeptide of the invention is to use PCR. This method may be used for introducing the DNA into a suitable vector, for example by engineering in suitable restriction sites, or it may be used to modify the DNA in other useful ways as is known in the art.

In this method the DNA to be enzymatically amplified is flanked by two specific primers which themselves become incorporated into the amplified DNA. The said specific primers may contain restriction endonuclease recognition sites which can be used for cloning into expression vectors using methods known in the art.

The DNA (or in the case of retroviral vectors, RNA) is then expressed in a suitable host to produce a polypeptide. Thus, the DNA encoding the polypeptide may be used in accordance with known techniques, appropriately modified in view of the teachings contained herein, to construct an expression vector, which is then used to transform an appropriate host cell for the expression and production of the polypeptide of the invention or binding moiety thereof.

A fourth aspect of the invention provides a host cell comprising a nucleic acid molecule as defined in the second aspect of the invention or a vector according to the third aspect of the invention.

The DNA (or in the case or retroviral vectors, RNA) encoding the polypeptide may be joined to a wide variety of other DNA sequences for introduction into an appropriate host. The companion DNA will depend upon the nature of the host, the manner of the introduction of the DNA into the host, and whether episomal maintenance or integration is desired.

Generally, the DNA is inserted into an expression vector, such as a plasmid, in proper orientation and correct reading frame for expression. If necessary, the DNA may be linked to the appropriate transcriptional and translational regulatory control nucleotide sequences recognised by the desired host, although such controls are generally available in the expression vector. The vector is then introduced into the host through standard techniques. Generally, not all of the hosts will be transformed by the vector. Therefore, it will be necessary to select for transformed host cells. One selection technique involves incorporating into the expression vector a DNA sequence, with any necessary control elements, that codes for a selectable trait in the transformed cell, such as antibiotic resistance. Alternatively, the gene for such selectable trait can be on another vector, which is used to co-transform the desired host cell.

Host cells that have been transformed by the expression vector are then cultured for a sufficient time and under appropriate conditions known to those skilled in the art in view of the teachings disclosed herein to permit the expression of the polypeptide, which can then be recovered.

Many expression systems are known, including bacteria (for example, *E. coli* and *Bacillus subtilis*), yeasts (for example *Saccharomyces cerevisiae*), filamentous fungi (for example *Aspergillus*), plant cells, animal cells and insect cells.

The vectors typically include a prokaryotic replicon, such as the ColE1 ori, for propagation in a prokaryote, even if the vector is to be used for expression in other, non-prokaryotic, cell types. The vectors can also include an appropriate promoter such as a prokaryotic promoter capable of directing the expression (transcription and translation) of the genes in a bacterial host cell, such as *E. coli*, transformed therewith.

A promoter is an expression control element formed by a DNA sequence that permits binding of RNA polymerase and transcription to occur. Promoter sequences compatible with exemplary bacterial hosts are typically provided in plasmid vectors containing convenient restriction sites for insertion of a DNA segment.

Typical prokaryotic vector plasmids are pUC18, pUC19, pBR322 and pBR329 available from Biorad Laboratories, (Richmond, Calif., USA) and pTrc99A and pKK223-3 available from Pharmacia, Piscataway, N.J., USA.

A typical mammalian cell vector plasmid is pSVL available from Pharmacia, Piscataway, N.J., USA. This vector uses the SV40 late promoter to drive expression of cloned genes, the highest level of expression being found in T antigen-producing cells, such as COS-1 cells.

An example of an inducible mammalian expression vector is pMSG, also available from Pharmacia. This vector uses the glucocorticoid-inducible promoter of the mouse mammary tumour virus long terminal repeat to drive expression of the cloned gene.

Useful yeast plasmid vectors are pRS403-406 and pRS413-416 and are generally available from Stratagene Cloning Systems, La Jolla, Calif. 92037, USA. Plasmids pRS403, pRS404, pRS405 and pRS406 are Yeast Integrating plasmids (YIps) and incorporate the yeast selectable markers HIS3, TRP1, LEU2 and URA3. Plasmid pRS413-416 is a Yeast Centromere plasmids (Ycps).

Other vectors and expression systems are well known in the art for use with a variety of host cells.

The host cell can be either prokaryotic or eukaryotic. Bacterial cells are preferred prokaryotic host cells and typically are a strain of *E. coli* such as, for example, the *E. coli* strains T7 (available from New England Biolabs, Ipswich, Mass., USA), DH5 (available from Bethesda Research Laboratories Inc., Bethesda, Md., USA), and RR1 (available from the American Type Culture Collection (ATCC) of Rockville, Md., USA; No. ATCC 31343). Preferred eukaryotic host cells include yeast, insect and mammalian cells, preferably vertebrate cells such as those from a mouse, rat, monkey or human fibroblastic and kidney cell lines. Yeast host cells include YPH499, YPH500 and YPH501 which are generally available from Stratagene Cloning Systems, La Jolla, Calif. 92037, USA. Preferred mammalian host cells include Chinese hamster ovary (CHO) cells available from the ATCC as CRL 1658 and 293 cells which are human embryonic kidney cells. Preferred insect cells are Sf9 cells which can be transfected with baculovirus expression vectors.

Transformation of appropriate cell hosts with a DNA construct is accomplished by well known methods that typically depend on the type of vector used. With regard to transformation of prokaryotic host cells, see, for example, Cohen et al. (1972) *Proc. Natl. Acad. Sci. USA* 69, 2110 and *Molecular Cloning: a Laboratory Manual*, 3rd edition, Sambrook & Russell, 2001, Cold Spring Harbor Laboratory Press. Transformation of yeast cells is described in Sherman et al (1986) *Methods In Yeast Genetics, A Laboratory Manual*, Cold Spring Harbor, N.Y. The method of Beggs (1978) *Nature* 275, 104-109 is also useful. With regard to vertebrate cells, reagents useful in transfecting such cells, for example calcium phosphate and DEAE-dextran or liposome formulations, are available from Stratagene Cloning Systems, or Life Technologies Inc., Gaithersburg, Md.

20877, USA. The relevant disclosures in the above documents are hereby incorporated by reference.

Electroporation is also useful for transforming and/or transfecting cells and is well known in the art for transforming yeast cells, bacterial cells, insect cells and vertebrate cells.

For example, many bacterial species may be transformed by the methods described in Luchansky et al (1988) *Mol. Microbiol.* 2, 637-646, the relevant disclosures in which document are hereby incorporated by reference. The greatest number of transformants is consistently recovered following electroporation of the DNA-cell mixture suspended in 2.5 PEB using 6250V per cm at 25 µFD.

Methods for transformation of yeast by electroporation are disclosed in Becker & Guarente (1990) *Methods Enzymol.* 194, 182, the relevant disclosures in which document are hereby incorporated by reference.

Successfully transformed cells, i.e. cells that contain a DNA construct encoding a polypeptide, can be identified by well known techniques. For example, cells resulting from the introduction of an expression construct of the present invention can be grown to produce the polypeptide of the invention. Cells can be harvested and lysed and their DNA content examined for the presence of the DNA using a method such as that described by Southern (1975) *J. Mol. Biol.* 98, 503 or Berent et al (1985) *Biotech.* 3, 208, the relevant disclosures in which document are hereby incorporated by reference. Alternatively, the presence of the protein in the supernatant or the cell pellet can be detected using antibodies.

In addition to assaying directly for the presence of recombinant DNA, successful transformation can be confirmed by well known immunological methods when the recombinant DNA is capable of directing the expression of the protein. For example, cells successfully transformed with an expression vector produce proteins displaying appropriate antigenicity.

Samples of cells suspected of being transformed are harvested and assayed for the protein using suitable antibodies.

The host cell may be a host cell within a non-human animal body. Thus, transgenic non-human animals which express a polypeptide by virtue of the presence of the transgene are included. Preferably, the transgenic non-human animal is a rodent such as a mouse. Transgenic non-human animals can be made using methods well known in the art (see below).

Methods of cultivating host cells and isolating recombinant proteins are well known in the art. It will be appreciated that, depending on the host cell, the compounds of the invention (or binding moieties thereof) produced may differ. For example, certain host cells, such as yeast or bacterial cells, either do not have, or have different, post-translational modification systems which may result in the production of font's of compounds of the invention (or binding moieties thereof) which may be post-translationally modified in a different way.

In one embodiment, the polypeptides for use in the methods of the invention are produced in a eukaryotic system, such as a mammalian cell.

Polypeptides can also be produced in vitro using a commercially available in vitro translation system, such as rabbit reticulocyte lysate or wheatgerm lysate (available from Promega). Preferably, the translation system is rabbit reticulocyte lysate. Conveniently, the translation system may be coupled to a transcription system, such as the TNT transcription-translation system (Promega). This system has the advantage of producing suitable mRNA transcript from an encoding DNA polynucleotide in the same reaction as the translation.

A fifth aspect of the invention provides a method for producing an agent as defined in the first aspect of the invention comprising culturing a population of host cells as defined in the third aspect of the invention under conditions in which the polypeptide is expressed, and isolating the polypeptide therefrom.

A sixth aspect of the invention provides a pharmaceutical composition comprising an effective amount of an agent as defined in the first aspect of an invention and a pharmaceutically-acceptable diluent, carrier or excipient.

In an alternative or additional embodiment the pharmaceutical composition is adapted for delivery by a route selected from the group comprising: intravenous; intramuscular; subcutaneous; intra-articular; pulmonary; intranasal; intraocular; intrathecal.

As used herein, 'pharmaceutical composition' means a therapeutically effective formulation according to the invention.

A 'therapeutically effective amount', or 'effective amount', or 'therapeutically effective', as used herein, refers to that amount which provides a therapeutic effect for a given condition and administration regimen. This is a pre-determined quantity of active material calculated to produce a desired therapeutic effect in association with the required additive and diluent, i.e. a carrier or administration vehicle. Further, it is intended to mean an amount sufficient to reduce or prevent a clinically significant deficit in the activity, function and response of the host. Alternatively, a therapeutically effective amount is sufficient to cause an improvement in a clinically significant condition in a host. As is appreciated by those skilled in the art, the amount of a compound may vary depending on its specific activity. Suitable dosage amounts may contain a predetermined quantity of active composition calculated to produce the desired therapeutic effect in association with the required diluent.

In the methods and use for manufacture of compositions of the invention, a therapeutically effective amount of the active component is provided. A therapeutically effective amount can be determined by the ordinary skilled medical or veterinary worker based on patient characteristics, such as age, weight, sex, condition, complications, other diseases, etc., as is well known in the art.

The agents, medicaments and pharmaceutical compositions of the invention may be delivered using an injectable sustained-release drug delivery system. These are designed specifically to reduce the frequency of injections. An example of such a system is Nutropin Depot which encapsulates recombinant human growth hormone (rhGH) in biodegradable microspheres that, once injected, release rhGH slowly over a sustained period. Preferably, delivery is performed intra-muscularly (i.m.) and/or sub-cutaneously (s.c.) and/or intravenously (i.v.).

The agents, medicaments and pharmaceutical compositions of the invention can be administered by a surgically implanted device that releases the drug directly to the required site. For example, Vitrasert releases ganciclovir directly into the eye to treat CMV retinitis. The direct application of this toxic agent to the site of disease achieves effective therapy without the drug's significant systemic side-effects.

Electroporation therapy (EPT) systems can also be employed for the administration of the agents, medicaments and pharmaceutical compositions of the invention. A device which delivers a pulsed electric field to cells increases the permeability of the cell membranes to the drug, resulting in a significant enhancement of intracellular drug delivery.

The agents, medicaments and pharmaceutical compositions of the invention can also be delivered by electro-incorporation (EI). EI occurs when small particles of up to 30 microns in diameter on the surface of the skin experience electrical pulses identical or similar to those used in electroporation. In EI, these particles are driven through the stratum corneum and into deeper layers of the skin. The particles can be loaded or coated with drugs or genes or can simply act as "bullets" that generate pores in the skin through which the drugs can enter.

An alternative method of delivery of the agents, medicaments and pharmaceutical compositions of the invention is the ReGel injectable system that is thermo-sensitive. Below body temperature, ReGel is an injectable liquid while at body temperature it immediately forms a gel reservoir that slowly erodes and dissolves into known, safe, biodegradable polymers. The active substance is delivered over time as the biopolymers dissolve.

The agents, medicaments and pharmaceutical compositions of the invention can also be delivered orally. The process employs a natural process for oral uptake of vitamin $B_{12}$ and/or vitamin D in the body to co-deliver proteins and peptides. By riding the vitamin $B_{12}$ and/or vitamin D uptake system, the agents, medicaments and pharmaceutical compositions of the invention can move through the intestinal wall. Complexes are synthesised between vitamin $B_{12}$ analogues and/or vitamin D analogues and the drug that retain both significant affinity for intrinsic factor (IF) in the vitamin $B_{12}$ portion/vitamin D portion of the complex and significant bioactivity of the active substance of the complex.

The agents, medicaments and pharmaceutical compositions of the invention can be introduced to cells by "Trojan peptides". These are a class of polypeptides called penetratins which have translocating properties and are capable of carrying hydrophilic compounds across the plasma membrane. This system allows direct targeting of oligopeptides to the cytoplasm and nucleus, and may be non-cell type specific and highly efficient. See Derossi et al. (1998), Trends Cell Biol 8, 84-87.

Preferably, the medicaments and/or pharmaceutical compositions of the present invention is a unit dosage containing a daily dose or unit, daily sub-dose or an appropriate fraction thereof, of the active ingredient.

The agents, medicaments and pharmaceutical compositions of the invention will normally be administered orally or by any parenteral route, in the form of a pharmaceutical composition comprising the active ingredient, optionally in the form of a non-toxic organic, or inorganic, acid, or base, addition salt, in a pharmaceutically acceptable dosage form. Depending upon the disorder and patient to be treated, as well as the route of administration, the compositions may be administered at varying doses.

In human therapy, the agents, medicaments and pharmaceutical compositions of the invention can be administered alone but will generally be administered in admixture with a suitable pharmaceutical excipient, diluent or carrier selected with regard to the intended route of administration and standard pharmaceutical practice.

For example, the agents, medicaments and pharmaceutical compositions of the invention can be administered orally, buccally or sublingually in the form of tablets, capsules, ovules, elixirs, solutions or suspensions, which may contain flavouring or colouring agents, for immediate-, delayed- or controlled-release applications. The agents, medicaments and pharmaceutical compositions of the invention may also be administered via intracavernosal injection.

Such tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, cellulose, milk sugar or high molecular weight polyethylene glycols. For aqueous suspensions and/or elixirs, the agents, medicaments and pharmaceutical compositions of the invention may be combined with various sweetening or flavouring agents, colouring matter or dyes, with emulsifying and/or suspending agents and with diluents such as water, ethanol, propylene glycol and glycerin, and combinations thereof.

The agents, medicaments and pharmaceutical compositions of the invention can be administered parenterally, for example, intravenously, intra-arterially, intraperitoneally, intra-thecally, intraventricularly, intrasternally, intracranially, intra-muscularly or subcutaneously, or they may be administered by infusion techniques. They are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

Medicaments and pharmaceutical compositions suitable for parenteral administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The medicaments and pharmaceutical compositions may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

For oral and parenteral administration to human patients, the daily dosage level of the agents, medicaments and pharmaceutical compositions of the invention will usually be from 0.002 to 0.4 mg/kg and/or 0.1 mg/kg to 20 mg/kg administered in single or divided doses.

Thus, for example, the tablets or capsules of the medicaments and pharmaceutical compositions of the invention may contain from 5 mg to 1400 mg (for example, from 7 mg to 1400 mg, or 5 mg to 1000 mg) and may preferably contain 5 mg to 200 mg of active agent for administration singly or two or more at a time, as appropriate.

In one embodiment, the agents, medicaments and pharmaceutical compositions of the invention are administered at a dosage ranging from 0.02 mg/kg to 2 mg/kg and at a frequency ranging from twice per week to once per month.

The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention.

The agents, medicaments and pharmaceutical compositions of the invention can also be administered intranasally or by inhalation and are conveniently delivered in the form of a dry powder inhaler or an aerosol spray presentation from a pressurised container, pump, spray or nebuliser with the use of a suitable propellant, e.g. dichlorodifluoromethane, trichlorofluoromethane, dichlorotetrafluoro-ethane, a hydrofluoroalkane such as 1,1,1,2-tetrafluoroethane (HFA 134A3 or 1,1,1,2,3,3,3-heptafluoropropane (HFA 227EA3), carbon dioxide or other suitable gas. In the case of a pressurised aerosol, the dosage unit may be determined by providing a valve to deliver a metered amount. The pressurised container, pump, spray or nebuliser may contain a solution or suspension of the active agent, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of an agent of the invention and a suitable powder base such as lactose or starch.

Aerosol or dry powder formulations are preferably arranged so that each metered dose or "puff" contains 5 mg to 1400 mg (for example, from 7 mg to 1400 mg, or 5 mg to 1000 mg) and preferably contain 5 mg to 200 mg of an agent of the invention for delivery to the patient. It will be appreciated that the overall daily dose with an aerosol will vary from patient to patient, and may be administered in a single dose or, more usually, in divided doses throughout the day.

Alternatively, the agents, medicaments and pharmaceutical compositions of the invention can be administered in the form of a suppository or pessary, or they may be applied topically in the form of a lotion, solution, cream, gel, ointment or dusting powder. The agents, medicaments and pharmaceutical compositions of the invention may also be transdermally administered, for example, by the use of a skin patch.

For application topically to the skin, the agents, medicaments and pharmaceutical compositions of the invention can be formulated as a suitable ointment containing the active agent suspended or dissolved in, for example, a mixture with one or more of the following: mineral oil, liquid petrolatum, white petrolatum, propylene glycol, polyoxyethylene polyoxypropylene agent, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouth-washes comprising the active ingredient in a suitable liquid carrier.

Generally, in humans, oral or parenteral administration of the agents, medicaments and pharmaceutical compositions of the invention is the preferred route, being the most convenient.

For veterinary use, the agents, medicaments and pharmaceutical compositions of the invention are administered as a suitably acceptable formulation in accordance with normal veterinary practice and the veterinary surgeon will determine the dosing regimen and route of administration which will be most appropriate for a particular animal.

The agents of the invention may be formulated at various concentrations, depending on the efficacy/toxicity of the compound being used, for example as described in the accompanying Examples. For in vitro applications, formulations may comprise a lower concentration of a compound of the invention.

Thus, the present invention provides a pharmaceutical formulation comprising an amount of an antibody or antigen-binding fragment, or variant, fusion or derivative thereof, of the invention effective to treat various conditions (as described above and further below).

Preferably, the pharmaceutical composition is adapted for delivery by a route selected from the group comprising: intravenous; intramuscular; subcutaneous; intra-articular; pulmonary; intranasal; intraocular; intrathecal.

The present invention also includes pharmaceutical compositions comprising pharmaceutically acceptable acid or base addition salts of the polypeptide binding moieties of the present invention. The acids which are used to prepare the pharmaceutically acceptable acid addition salts of the aforementioned base compounds useful in this invention are those which form non-toxic acid addition salts, i.e. salts containing pharmacologically acceptable anions, such as the hydrochloride, hydrobromide, hydroiodide, nitrate, sulphate, bisulphate, phosphate, acid phosphate, acetate, lactate, citrate, acid citrate, tartrate, bitartrate, succinate, maleate, fumarate, gluconate, saccharate, benzoate, methanesulphonate, ethanesulphonate, benzenesulphonate, p-toluenesulphonate and pamoate [i.e. 1,1'-methylene-bis-(2-hydroxy-3 naphthoate)] salts, among others.

Pharmaceutically acceptable base addition salts may also be used to produce pharmaceutically acceptable salt forms of the agents according to the present invention.

The chemical bases that may be used as reagents to prepare pharmaceutically acceptable base salts of the present agents that are acidic in nature are those that form non-toxic base salts with such compounds. Such non-toxic base salts include, but are not limited to those derived from such pharmacologically acceptable cations such as alkali metal cations (e.g. potassium and sodium) and alkaline earth metal cations (e.g. calcium and magnesium), ammonium or water-soluble amine addition salts such as N-methylglucamine-(meglumine), and the lower alkanolammonium and other base salts of pharmaceutically acceptable organic amines, among others.

The agents and/or polypeptide binding moieties of the invention may be lyophilised for storage and reconstituted in a suitable carrier prior to use. Any suitable lyophilisation method (e.g. spray drying, cake drying) and/or reconstitution techniques can be employed. It will be appreciated by those skilled in the art that lyophilisation and reconstitution can lead to varying degrees of antibody activity loss (e.g. with conventional immunoglobulins, IgM antibodies tend to have greater activity loss than IgG antibodies) and that use levels may have to be adjusted upward to compensate. In one embodiment, the lyophilised (freeze dried) polypeptide binding moiety loses no more than about 20%, or no more than about 25%, or no more than about 30%, or no more than about 35%, or no more than about 40%, or no more than about 45%, or no more than about 50% of its activity (prior to lyophilisation) when re-hydrated.

A seventh aspect of the invention provides:
(a) a kit comprising an agent as defined in the first aspect of the invention or a pharmaceutical composition as defined in the sixth aspect of the invention; and
(b) (optionally) instructions for performing the method or use as defined in the eighth to the twelfth aspects of the invention.

Alternatively, the kit may comprise a detectable antibody or antigen-binding fragment or derivative thereof according to the invention, suitable for use in diagnosis. Such a diagnostic kit may comprise, in an amount sufficient for at least one assay, the diagnostic agent as a separately packaged reagent. Instructions for use of the packaged reagent are also typically included. Such instructions typically include a tangible expression describing reagent concentrations and/or at least one assay method parameter such as the relative amounts of reagent and sample to be mixed, maintenance time periods for reagent/sample admixtures, temperature, buffer conditions and the like.

An eight aspect of the invention provides an agent as defined in the first aspect of the invention for use in medicine.

Methods of manufacturing a medicament using an active agent, such as the agent of the invention, are well known to persons skilled in the art of medicine and pharmacy.

A ninth aspect of the invention provides an agent as defined in the first aspect of the invention for use in treating a disease or condition that would benefit from the clearance of hematopoietic stem cells, hematopoietic progenitor cells and/or hematopoietic cancer stem cells.

In an alternative or additional embodiment the disease or condition is a disease or condition that would benefit from transplantation of hematopoietic stem cells.

In an alternative or additional embodiment the disease or condition is non-malignant. The non-malignant disease or condition may be selected from the group consisting of Severe aplastic anemia (SAA), Wiskott Aldrich Syndrome, Hurlers Syndrome, FHL, CGD, Kostmanns syndrome, Severe immunodeficiency syndrome (SCID), other autoimmune disorders such as SLE, Multiple sclerosis, IBD, Crohns Disease, Ulcerative colitis, Sjögrens syndrome, vasculitis, Lupus, Myasthenia Gravis, Wegeners disease, inborn errors of metabolism and/or other immunodeficiencies.

In an alternative or additional embodiment the disease or condition is malignant. The malignant disease or condition may be selected from the group consisting of the myelodysplastic syndromes (MDS), leukaemia (e.g., acute lymphoblastic leukemia (ALL), acute myelogenous leukemia (AML), acute monocytic leukemia (AMoL), chronic lymphocytic leukemia (CLL), chronic myelogenous leukemia (CML) and other leukemias (such as hairy cell leukemia (HCL), T-cell prolymphocytic leukemia (T-PLL), large granular lymphocytic leukemia and adult T-cell leukemia), lymphoma (e.g., Precursor T-cell leukemia/lymphoma, Burkitt lymphoma, follicular lymphoma, diffuse large B cell lymphoma, mantle cell lymphoma, B-cell chronic lymphocytic leukemia/lymphoma, MALT lymphoma, solid tumours (e.g. renal, hepatic and pancreatic cancer), Mycosis fungoides, Peripheral T-cell lymphoma not otherwise specified, Nodular sclerosis form of Hodgkin lymphoma Mixed-cellularity subtype of Hodgkin lymphoma).

The term "malignant cell" will be understood by those skilled in the art of cell biology, and includes a cell which is capable of, or exhibits, uncontrolled cellular division and/or proliferation and/or the ability to metastasize and/or invade tissues in a body. Such cells may comprise cancerous tumours and are frequently resistant to many anti-proliferative therapies.

In an alternative or additional embodiment the malignant disease is, or is selected from, the myelodysplastic syndromes (MDS).

In an alternative or additional embodiment the malignant disease is leukaemia. The leukaemia may be selected from the group consisting of acute lymphoblastic leukemia (ALL), acute myelogenous leukemia (AML), acute monocytic leukemia (AMoL), chronic lymphocytic leukemia (CLL), chronic myelogenous leukemia (CML) and other leukemias (such as hairy cell leukemia (HCL), T-cell prolymphocytic leukemia (T-PLL), large granular lymphocytic leukemia and adult T-cell leukemia.

In an alternative or additional embodiment the treatment comprises or consists of the step of:
(a) destroying hematopoietic stem cells, hematopoietic progenitor cells and/or hematopoietic cancer stem cells in the individual comprising or consisting of administering a sufficient amount of an agent defined in the first aspect of the invention.

In an alternative or additional embodiment the treatment is capable of destroying at least 50% of the hematopoietic stem cells and/or hematopoietic cancer stem cells in the individual, for example, greater than or equal to 55%, ≥60%, ≥65%, ≥70%, ≥75%, ≥80%, ≥85%, ≥90%, ≥95%, ≥96%, ≥97%, ≥98%, ≥99% or 100% of the stem cells and/or cancer stem cells.

In an alternative or additional embodiment step (a) comprises co-administration of one or more chemotherapeutic agent, radiotherapy and/or immunotherapy.

In an alternative or additional embodiment the one or more chemotherapeutic agent is selected from the group consisting of busulfan, cyclophosphamide, fludarabine, treosulphane, melphalan, and thiotepa.

In an alternative or additional embodiment the radiotherapy is selected from the group consisting of total body irradiation and total lymphoid irradiation.

In an alternative or additional embodiment the treatment comprises the step of:
(b) removal of the agent according to the first aspect of the invention from the individual.

In an alternative or additional embodiment at least 50% of the agent according to the first aspect of the invention in the individual is removed, for example, greater than or equal to 55%, ≥60%, ≥65%, ≥70%, ≥75%, ≥80%, ≥85%, ≥90%, ≥95%, ≥96%, ≥97%, ≥98%, ≥99% or 100% of the agent according to the first aspect of the invention in the individual is removed. The removal may be performed using plasmapheresis.

In an alternative or additional embodiment the treatment comprises the step of:
(c) hematopoietic stem cell transplantation (HSCT).

In an alternative or additional embodiment the hematopoietic stem cell transplantation is autologous, allogeneic, syngeneic or xenogeneic.

In an alternative or additional embodiment the agent is capable of preventing and/or reducing graft-versus-host-disease (GVHD) and/or graft-versus-leukemia (GVL).

In an alternative or additional embodiment the agent is capable of allowing graft-versus-leukemia (GVL).

In an alternative or additional embodiment the stem cell transplantation is a first stem cell transplantation.

In an alternative or additional embodiment the stem cell transplantation is a re-transplantation, e.g. after relapse.

A tenth aspect of the invention provides the use of an agent defined in the first aspect of the invention in the preparation of a medicament for use in treating a disease or condition that would benefit from the clearance of hematopoietic stem cells, hematopoietic progenitor cells and/or hematopoietic cancer stem cells. The same embodiments as the ninth aspect of the invention can be applied to the tenth aspect of the invention.

An eleventh aspect of the invention provides the use of an agent defined in the first aspect of the invention in treating a disease or condition that would benefit from the clearance of hematopoietic stem cells, hematopoietic progenitor cells and/or hematopoietic cancer stem cells. The same embodiments as the ninth aspect of the invention can be applied to the eleventh aspect of the invention.

A twelfth aspect of the invention provides a method of treating a disease or condition that would benefit from the clearance of hematopoietic stem cells, hematopoietic progenitor cells and/or hematopoietic cancer stem cells in an individual comprising administering an effective amount of an agent defined in the first aspect of the invention. The same embodiments as the ninth aspect of the invention can be applied to the twelfth aspect of the invention.

Exemplary database accession numbers for the proteins discussed above include the following:

| Protein | UniProt ID | RefSeq nuc | RefSeq prot | Entrez ID |
|---|---|---|---|---|
| CD34 | P28906 | NM_001025109.1 | NP_001020280.1 | |
| CD3 delta | P04234 | NM_000732.4 | NP_000723.1 | |
| CD3 epsilon | P07766 | NM_000733.3 | NP_000724.1 | |
| CD3 gamma | P09693 | NM_000073.2 | NP_000064.1 | |
| NKG2D | P26718 | NM_007360.3 | NP_031386.2 | |
| NKp44 | O95944 | NM_001199509.1 | NP_001186438.1 | |
| NKp46 | O76036 | NM_001145457.2 | NP_001138929.2 | |
| NKp30 | O14931 | NM_001145466.1 | NP_001138938.1 | |
| DNAM 1 | Q15762 | NM_006566.3 | NP_006557.2 | |
| CD16a | P08637 | NM_000569.6 | NP_000560.5 | |
| CD16b | O75015 | NM_000570.4 | NP_000561.3 | |
| CD133 | O43490 | NM_001145847.1 | NP_001139319.1 | |
| CD59 | P13987 | NM_000611.5 | NP_000602.1 | |
| Thy1/ CD90 | P04216 | NM_006288.3 | NP_006279.2 | |
| C-kit/ CD117 | P10721 | NM_000222.2 | NP_000213.1 | |
| TCR alpha | | | | 6955 |
| TCR beta | | | | 6957 |

The listing or discussion in this specification of an apparently prior-published document should not necessarily be taken as an acknowledgement that the document is part of the state of the art or is common general knowledge.

Preferred, non-limiting examples which embody certain aspects of the invention will now be described, with reference to the following FIGURES:

EXAMPLES

Example 1

A patient suffering from AML is about to undergo allogeneic HSCT. The patient is >70 years with fungal infection and has little chance to survive standard chemotherapy given as conditioning regimen. Before the transplantation the patient needs to undergo a preconditioning to minimize the risk of relapse due to survival of malignant cancer cells, minimize risk for rejection and make space for the new hematopoietic stem cells. In addition, the pre-conditioning will also influence the risk of GVHD. Instead of using the common methods of high dose chemotherapy and irradiation, the patient is treated with antibody-based immunotherapy using a CD34/CD3 BiTE (e.g., the agent of Example 5, below) in combination with or without mild chemotherapy/radiation and with or without T-cell antibodies. This milder variant of pre-conditioning will likely reduce the risk of acute GVHD and the patient will have very little toxicity resulting from the treatment. Due to the target antigen of the antibody-based immunotherapy, a putatively better anti-tumor effect will be achieved against cancer cells with undifferentiated phenotype.

Example 2

A patient suffering from MDS has already received an allogeneic HSCT but has relapsed in the underlying malignant disease. The patient is eligible for a re-transplantation if the patient will be in hematological remission, i.e. no detection of malignant cells in the bone marrow. Patients considered for a re-transplantation are usually in much worse shape clinically than patients prior to primary HSCT. Instead of using the common methods of heavy chemotherapy as induction therapy, these patients greatly benefit from a milder and more efficient treatment in order to achieve remission. Before the re-transplantation the patient is treated with infusion(s) of a CD34/CD3 BiTE (e.g., the agent of Example 5, below) with chemotherapy and with or without T-cell antibodies. This will minimize the risk of another relapse due to survival of malignant cancer cells, and minimize risk for GVHD.

Example 3

A patient suffering from a non-malignant disease, e.g. Severe aplastic anemia (SAA), Wiskott Aldrich Syndrome, Hurlers Syndrome, FHL, CGD, Kostmanns syndrome, Severe immunodeficiency syndrome (SCID), other autoimmune disorders, inborn errors of metabolism or other immunodeficiencies, are eligible for a HSCT to exchange their non-functional hematopoietic cell compartment. Without treatment, the mortality rate for both of these conditions is extremely high. Before transplantation, a milder pretreatment compared to patients with malignant disease is used. While patients with non-malignant disease won't benefit from GVHD or GVL (Graft-versus-leukemia) (which could be beneficial in for example leukemia), an even milder pre-conditioning is warranted in non-malignant diseases. Instead of using conventional chemotherapy with or without irradiation the patient is instead pretreated with a CD34/C3 specific BiTE (e.g., the agent of Example 5, below), T-cell antibodies and very mild chemotherapy. This will make the risk for GVHD decrease further, reduce toxicity and possibly open up the use of allogeneic HSCT in other non-malignant diseases, which are not currently treatable, such as various autoimmune diseases.

Example 4

A patient suffering from MDS is eligible for HSCT. The malignant cells of the patient express CD34. While using the CD34/CD3 specific BiTE (e.g., the agent of Example 5, below) in the pre-conditioning together with standard reduced protocol with chemotherapy treatment prior to HSCT, there will be a reduced risk that the patient will relapse in the underlying malignancy after HSCT. This will be of pivotal importance since relapse of MDS is the most common cause of death after allogeneic HSCT.

Example 5

We started with 50 ml peripheral blood from a healthy individual pretreated with Granolucyte Colony stimulating Factor (G-CSF, Amgen, Calif., US, 10 micrograms/kg for two consecutive days). This growth hormone promotes in vivo growth of lymphocytes and Hematopoetic stem cells (CD34+ cells). When these increase the growth in the bone marrow cells are pushed out into peripheral blood. This increases the frequency of CD34 Hematopoetic stem cells in peripheral blood often to more than >2%. The blood was centrifuged on a ficoll density gradient (Fresenius Kabi, Norway) in order to remove red blood cells. The remaining white blood cells were collected and washed twice in PBS buffer. White blood cells where then resuspended in complete RPMI growth medium (GIBCO, Germany) containing 10% human heat-inactivated serum, penicillin and glutamine (GIBCO, Germany). Cells were then seeded in 6 well plates at a concentration of 1 million cells/ml medium. CD34/CD3 bispecific antibodies or the relevant controls missing one of the binding sites, CD34/(-) or CD3/(-) (for sequences see Appendix 1) were incubated with the white blood cells over night at 37° C., 5% CO2. After incubation the cells were collected and washed before resuspension with PBS (GIBCO, Germany).

In short, for surface staining only, white blood cells were incubated with antibodies for 20 minutes at 4° C. and subsequently stained with dead cell marker 7AAD for 10 minutes at room temperature. Acquisition was performed with the BD LSRII using BD FACS Diva software (BD Biosciences, Franklin Lakes, N.J., USA). Fluorescence-minus-one (FMO) samples were used to obtain proper gating strategies.

The following antibodies were used. For Fluorescein isothiocyanate (FITC) anti-CD3 (SK7); FITC anti-CD34 (8G12); FITC anti-CD19 (HIB19); FITC anti-CD56 (NCAM16.2); phycoerythrin (PE) anti-CD3 (SK7); PE anti-CD56 (MY31), PE anti-IL-2 (MQ1-17H12); 7-Amino-Actinomycin D (7AAD); APC anti-CD4 (RPA-T4); APC anti-CD8 (RPA-T8) where bought from BD Biosciences (Franklin Lakes, N.J.); Qdot605 anti-CD3 (UCHT1) and Pacific Orange anti-CD8 (3B5) came from Invitrogen, Eugene, Oreg., USA. FITC anti-TCR PANγδ (IMMU510) and Krome Orange anti-CD4 (13B8.2) was purchased from Beckman Coulter, Fullerton, Calif., USA.

Data is described in FIG. 1 that shows one representative experiment out of three. All with similar results with blood from different individuals. The peripheral blood contained between 1 and 2% CD34+ hematopoietic stem cells. The data clearly shows that there is a specific effect of the bispecific antibody CD34/CD3 with specific killing effect against CD34+ cells after the overnight culture. (FIG. 1 A). With the increasing concentration of CD34/CD3 bispecific the percentage of dead cells (7AAD+) increases from background (10.8%) to 32.3%. This is in contrast to cells treated with either CD34+/CD3(-) reagent where there is only an increase to 14.2%. In cells treated with CD34(-)/CD3+ reagent there is an increase to 27.2% dead CD34+ cells. This is higher than the other control but lower than the bispecific CD3+/CD34+ bispecific antibody. The effect of the CD34/CD3 bispecific antibody is also specific against CD34+ cells. FIG. 1 B shows that with increasing concentrations of the bispecific antibody there is no increase in the amount of dead B cells (defined as CD3(-)/CD19+). With the lowest concentration there is 3% dead B-cells and with the highest concentration the dead cells are only 2%. The same situation is seen with NK-cells (defined as CD3(-)/CD56+). With the lowest concentration the frequency of dead cells in 26.8% while in the highest concentration it is 29.8%. So there does not seem to be any specific toxicitiy of the bispecific antibody against non-relevant white blood cells such as B-cells and NK-cells.

APPENDIX I anti-CD34 antibody sequences derived from US patent US 2010/0311955 A1.
anti-CD3 scFv sequences based on blinatumomab as described in U.S. Pat. No. 7,635,472.
anti-CD34-HC-anti-CD3-scFv

[SEQ ID NO: 63]
QIQLVQSGSELKKPGASVKVSCKASGYTFTNYGMNWVRQAPGQGLKWMGW

INTNTGEPKYAEEFKGRFALSLDTSVSTAYLQINSLKAEDTAVYFCARGY

GNYARGAWLAYWGQGTLVTVSSASTKGPSVFPLAPSSKSTSGGTAALGCL

VKDYFPEPVTVSWNSGALTSGVHTFPAVLQSSGLYSLSSVVTVPSSSLGT

QTYICNVNHKPSNTKVDKKVEPKSCDKTHTCPPCPAPELLGGPSVFLFPP

KPKDTLMISRTPEVTCVVVDVSHEDPEVKFNWYVDGVEVHNAKTKPREEQ

YNSTYRVVSVLTVLHQDWLNGKEYKCKVSNKALPAPIEKTISKAKGQPRE

PQVYTLPPSREEMTKNQVSLTCLVKGFYPSDIAVEWESNGQPENNYKTTP

PVLDSDGSFFLYSKLTVDKSRWQQGNVFSCSVMHEALHNHYTQKSLSLSP

GKGGGGSGGGGSGGGGSDIKLQQSGAELARPGASVKMSCKTSGYTFTRYT

MHWVKQRPGQGLEWIGYINPSRGYTNYNQKFKDKATLTTDKSSSTAYMQL

SSLTSEDSAVYYCARYYDDHYCLDYWGQGTTLTVSSVEGGSGGSGGSGGS

GGVDDIQLTQSPAIMSASPGEKVTMTCRASSSVSYMNWYQQKSGTSPKRW

IYDTSKVASGVPYRFSGSGSGTSYSLTISSMEAEDAATYYCQQWSSNPLT

FGAGTKLELK anti-CD34-LC
[SEQ ID NO: 26]
DVLLTQSPLSLPVTLGQPASISCRSSQTIVHSNGNTYLEWFQQRPGQSPR

LLIYQVSNRFSGVPDRFSGSGSGTDFTLKISRVEAEDVGVYYCFQGSHVP

RTFGGGTKVEIKRTVAAPSVFIFPPSDEQLKSGTASVVCLLNNFYPREAK

VQWKVDNALQSGNSQESVTEQDSKDSTYSLSST

SEQUENCE LISTING

<160> NUMBER OF SEQ ID NOS: 84

<210> SEQ ID NO 1

<211> LENGTH: 330
<212> TYPE: PRT
<213> ORGANISM: Artificial
<220> FEATURE:
<223> OTHER INFORMATION: 4C8 anti-CD34 antibody heavy chain constant
      region

<400> SEQUENCE: 1

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 2
<211> LENGTH: 106
<212> TYPE: PRT
<213> ORGANISM: Artificial
<220> FEATURE:
<223> OTHER INFORMATION: 4C8 anti-CD34 antibody light chain constant region

<400> SEQUENCE: 2

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 3
<211> LENGTH: 10
<212> TYPE: PRT
<213> ORGANISM: Artificial
<220> FEATURE:
<223> OTHER INFORMATION: 4C8 anti-CD34 antibody heavy chain CDR1

<400> SEQUENCE: 3

Gly Tyr Thr Phe Thr Asn Tyr Gly Met Asn
1               5                   10

<210> SEQ ID NO 4
<211> LENGTH: 17
<212> TYPE: PRT
<213> ORGANISM: Artificial
<220> FEATURE:
<223> OTHER INFORMATION: 4C8 anti-CD34 antibody heavy chain CDR2

<400> SEQUENCE: 4

Trp Ile Asn Thr Asn Thr Gly Glu Pro Lys Tyr Ala Glu Glu Phe Lys
1               5                   10                  15

Gly

<210> SEQ ID NO 5
<211> LENGTH: 13
<212> TYPE: PRT
<213> ORGANISM: Artificial
<220> FEATURE:
<223> OTHER INFORMATION: 4C8 anti-CD34 antibody heavy chain CDR3

<400> SEQUENCE: 5

Gly Tyr Gly Asn Tyr Ala Arg Gly Ala Trp Leu Ala Tyr
1               5                   10

<210> SEQ ID NO 6
<211> LENGTH: 16
<212> TYPE: PRT
<213> ORGANISM: Artificial
<220> FEATURE:
<223> OTHER INFORMATION: 4C8 anti-CD34 antibody light chain CDR1

<400> SEQUENCE: 6

Arg Ser Ser Gln Thr Ile Val His Ser Asn Gly Asn Thr Tyr Leu Glu
1               5                   10                  15

```
<210> SEQ ID NO 7
<211> LENGTH: 7
<212> TYPE: PRT
<213> ORGANISM: Artificial
<220> FEATURE:
<223> OTHER INFORMATION: 4C8 anti-CD34 antibody light chain CDR2

<400> SEQUENCE: 7

Gln Val Ser Asn Arg Phe Ser
1               5

<210> SEQ ID NO 8
<211> LENGTH: 9
<212> TYPE: PRT
<213> ORGANISM: Artificial
<220> FEATURE:
<223> OTHER INFORMATION: 4C8 anti-CD34 antibody light chain CDR3

<400> SEQUENCE: 8

Phe Gln Gly Ser His Val Pro Arg Thr
1               5

<210> SEQ ID NO 9
<211> LENGTH: 8
<212> TYPE: PRT
<213> ORGANISM: Artificial
<220> FEATURE:
<223> OTHER INFORMATION: 1252 anti-CD3 antibody heavy chain CDR1

<400> SEQUENCE: 9

Gly Phe Thr Phe Asp Asp Tyr Thr
1               5

<210> SEQ ID NO 10
<211> LENGTH: 8
<212> TYPE: PRT
<213> ORGANISM: Artificial
<220> FEATURE:
<223> OTHER INFORMATION: 1268 anti-CD3 antibody heavy chain CDR1

<400> SEQUENCE: 10

Gly Phe Thr Phe Asp Asp Phe Thr
1               5

<210> SEQ ID NO 11
<211> LENGTH: 8
<212> TYPE: PRT
<213> ORGANISM: Artificial
<220> FEATURE:
<223> OTHER INFORMATION: 1284 anti-CD3 antibody heavy chain CDR1

<400> SEQUENCE: 11

Gly Phe Thr Phe Asp Asp Tyr Thr
1               5

<210> SEQ ID NO 12
<211> LENGTH: 8
<212> TYPE: PRT
<213> ORGANISM: Artificial
<220> FEATURE:
<223> OTHER INFORMATION: 1300 anti-CD3 antibody heavy chain CDR1

<400> SEQUENCE: 12

Gly Phe Thr Phe Arg Ser Tyr Ala
1               5
```

```
<210> SEQ ID NO 13
<211> LENGTH: 8
<212> TYPE: PRT
<213> ORGANISM: Artificial
<220> FEATURE:
<223> OTHER INFORMATION: 1316 anti-CD3 antibody heavy chain CDR1

<400> SEQUENCE: 13

Gly Phe Thr Phe Arg Ser Tyr Gly
1               5

<210> SEQ ID NO 14
<211> LENGTH: 122
<212> TYPE: PRT
<213> ORGANISM: Artificial
<220> FEATURE:
<223> OTHER INFORMATION: 4C8 anti-CD34 antibody heavy chain

<400> SEQUENCE: 14

Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Lys Trp Met
        35                  40                  45

Gly Trp Ile Asn Thr Asn Thr Gly Glu Pro Lys Tyr Ala Glu Glu Phe
    50                  55                  60

Lys Gly Arg Phe Ala Leu Ser Leu Asp Thr Ser Val Ser Thr Ala Tyr
65                  70                  75                  80

Leu Gln Ile Asn Ser Leu Lys Ala Glu Asp Thr Ala Val Tyr Phe Cys
                85                  90                  95

Ala Arg Gly Tyr Gly Asn Tyr Ala Arg Gly Ala Trp Leu Ala Tyr Trp
            100                 105                 110

Gly Gln Gly Thr Leu Val Thr Val Ser Ser
        115                 120

<210> SEQ ID NO 15
<211> LENGTH: 117
<212> TYPE: PRT
<213> ORGANISM: Artificial
<220> FEATURE:
<223> OTHER INFORMATION: mMY10 anti-CD34 antibody heavy chain

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Thr Ser His
            20                  25                  30

Gly Val His Trp Val Arg Gln Ala Pro Gly Lys Gly Leu Glu Trp Leu
        35                  40                  45

Gly Val Ile Trp Gly Ala Gly Arg Thr Asp Tyr Asn Ala Ala Phe Ile
    50                  55                  60

Ser Arg Leu Ser Ile Ser Arg Asp Ile Ser Lys Ser Gln Val Tyr Leu
65                  70                  75                  80

Gln Met Asn Ser Leu Arg Ala Glu Asp Thr Ala Val Tyr Tyr Cys Ala
                85                  90                  95

Arg Asn Arg Tyr Glu Ser Tyr Phe Asp Tyr Trp Gly Gln Gly Thr Leu
            100                 105                 110

Val Thr Val Ser Ser
        115
```

<210> SEQ ID NO 16
<211> LENGTH: 130
<212> TYPE: PRT
<213> ORGANISM: Artificial
<220> FEATURE:
<223> OTHER INFORMATION: 202 anti-CD133 antibody heavy chain 47

<400> SEQUENCE: 16

```
Leu Glu Val Lys Leu Val Glu Ser Gly Pro Glu Leu Lys Lys Pro Gly
1               5                   10                  15

Glu Thr Val Lys Ile Ser Cys Lys Ala Ser Gly Tyr Thr Phe Thr Asp
            20                  25                  30

Tyr Ser Met His Trp Val Asn Gln Ala Pro Gly Lys Gly Leu Lys Trp
        35                  40                  45

Met Gly Trp Ile Asn Thr Glu Thr Gly Glu Pro Ser Tyr Ala Asp Asp
    50                  55                  60

Phe Lys Gly Arg Phe Ala Phe Ser Leu Glu Thr Ser Ala Ser Thr Ala
65                  70                  75                  80

Tyr Leu Gln Ile Asn Asn Leu Lys Asn Glu Asp Thr Ala Thr Tyr Phe
                85                  90                  95

Cys Ala Thr Asp Tyr Gly Asp Tyr Phe Asp Tyr Trp Gly Gln Gly Thr
            100                 105                 110

Thr Leu Thr Val Ser Ser Ala Lys Thr Thr Pro Pro Ser Val Thr Ser
        115                 120                 125

Gly Gln
    130
```

<210> SEQ ID NO 17
<211> LENGTH: 133
<212> TYPE: PRT
<213> ORGANISM: Artificial
<220> FEATURE:
<223> OTHER INFORMATION: 202 anti-CD133 antibody heavy chain 48

<400> SEQUENCE: 17

```
Leu Glu Val Lys Leu Val Glu Ser Gly Pro Glu Leu Lys Lys Pro Gly
1               5                   10                  15

Glu Thr Val Lys Ile Ser Cys Lys Ala Ser Gly Tyr Thr Phe Thr Asp
            20                  25                  30

Tyr Ser Met His Trp Val Asn Gln Ala Pro Gly Lys Gly Leu Lys Trp
        35                  40                  45

Met Gly Trp Ile Asn Thr Glu Thr Gly Glu Pro Ser Tyr Ala Asp Asp
    50                  55                  60

Phe Lys Gly Arg Phe Ala Phe Ser Leu Glu Thr Ser Ala Ser Thr Ala
65                  70                  75                  80

Tyr Leu Gln Ile Asn Asn Leu Lys Asn Glu Asp Thr Ala Thr Tyr Phe
                85                  90                  95

Cys Ala Thr Asp Tyr Gly Asp Tyr Phe Asp Tyr Trp Gly Gln Gly Thr
            100                 105                 110

Thr Leu Thr Val Ser Ser Ala Lys Thr Thr Pro Pro Ser Val Thr Ser
        115                 120                 125

Gly Gln Ala Gly Gln
    130
```

<210> SEQ ID NO 18
<211> LENGTH: 133
<212> TYPE: PRT

```
<213> ORGANISM: Artificial
<220> FEATURE:
<223> OTHER INFORMATION: 202 anti-CD133 antibody heavy chain 49

<400> SEQUENCE: 18

Pro Glu Val Met Leu Val Glu Ser Gly Pro Glu Leu Lys Lys Pro Gly
1               5                   10                  15

Glu Thr Val Lys Ile Ser Cys Lys Ala Ser Gly Tyr Thr Phe Thr Asp
                20                  25                  30

Tyr Ser Met His Trp Val Asn Gln Ala Pro Gly Lys Gly Leu Lys Trp
            35                  40                  45

Met Gly Trp Ile Asn Thr Glu Thr Gly Glu Pro Ser Tyr Ala Asp Asp
    50                  55                  60

Phe Lys Gly Arg Phe Ala Phe Ser Leu Glu Thr Ser Ala Ser Thr Ala
65                  70                  75                  80

Tyr Leu Gln Ile Asn Asn Leu Lys Asn Glu Asp Thr Ala Thr Tyr Phe
                85                  90                  95

Cys Ala Thr Asp Tyr Gly Asp Tyr Phe Asp Tyr Trp Gly Gln Gly Thr
            100                 105                 110

Thr Leu Thr Val Ser Ser Ala Lys Thr Thr Pro Pro Ser Val Thr Ser
        115                 120                 125

Gly Gln Ala Gly Gln
    130

<210> SEQ ID NO 19
<211> LENGTH: 133
<212> TYPE: PRT
<213> ORGANISM: Artificial
<220> FEATURE:
<223> OTHER INFORMATION: 202 anti-CD133 antibody heavy chain 50

<400> SEQUENCE: 19

Leu Glu Val Lys Leu Val Glu Ser Gly Pro Glu Leu Lys Lys Pro Gly
1               5                   10                  15

Glu Thr Val Lys Ile Ser Cys Lys Ala Ser Gly Tyr Thr Phe Thr Asp
                20                  25                  30

Tyr Ser Met His Trp Val Asn Gln Ala Pro Gly Lys Gly Leu Lys Trp
            35                  40                  45

Met Gly Trp Ile Asn Thr Glu Thr Gly Glu Pro Ser Tyr Ala Asp Asp
    50                  55                  60

Phe Lys Gly Arg Phe Ala Phe Ser Leu Glu Thr Ser Ala Ser Thr Ala
65                  70                  75                  80

Tyr Leu Gln Ile Asn Asn Leu Lys Asn Glu Asp Thr Ala Thr Tyr Phe
                85                  90                  95

Cys Ala Thr Asp Tyr Gly Asp Tyr Phe Asp Tyr Trp Gly Gln Gly Thr
            100                 105                 110

Thr Leu Thr Val Ser Ser Ala Lys Thr Thr Pro Pro Ser Val Thr Ser
        115                 120                 125

Gly Gln Ala Gly Gln
    130

<210> SEQ ID NO 20
<211> LENGTH: 133
<212> TYPE: PRT
<213> ORGANISM: Artificial
<220> FEATURE:
<223> OTHER INFORMATION: 202 anti-CD133 antibody heavy chain 51

<400> SEQUENCE: 20
```

Leu Glu Val His Leu Val Glu Ser Gly Pro Glu Leu Lys Lys Pro Gly
1               5                   10                  15

Glu Thr Val Lys Ile Ser Cys Lys Ala Ser Gly Tyr Thr Phe Thr Asp
                20                  25                  30

Tyr Ser Met His Trp Val Asn Gln Ala Pro Gly Lys Gly Leu Lys Trp
            35                  40                  45

Met Gly Trp Ile Asn Thr Glu Thr Gly Glu Pro Ser Tyr Ala Asp Asp
    50                  55                  60

Phe Lys Gly Arg Phe Ala Phe Ser Leu Glu Thr Ser Ala Ser Thr Ala
65                  70                  75                  80

Tyr Leu Gln Ile Asn Asn Leu Lys Asn Glu Asp Thr Ala Thr Tyr Phe
                85                  90                  95

Cys Ala Thr Asp Tyr Gly Asp Tyr Phe Asp Tyr Trp Gly Gln Gly Thr
            100                 105                 110

Thr Leu Thr Val Ser Ser Ala Lys Thr Thr Pro Pro Ser Val Thr Ser
        115                 120                 125

Gly Gln Ala Gly Gln
        130

<210> SEQ ID NO 21
<211> LENGTH: 133
<212> TYPE: PRT
<213> ORGANISM: Artificial
<220> FEATURE:
<223> OTHER INFORMATION: 202 anti-CD133 antibody heavy chain 52

<400> SEQUENCE: 21

Leu Glu Val Lys Leu Val Glu Ser Gly Pro Glu Leu Lys Lys Pro Gly
1               5                   10                  15

Glu Thr Val Lys Ile Ser Cys Lys Ala Ser Gly Tyr Thr Phe Thr Asp
                20                  25                  30

Tyr Ser Met His Trp Val Asn Gln Ala Pro Gly Lys Gly Leu Lys Trp
            35                  40                  45

Met Gly Trp Ile Asn Thr Glu Thr Gly Glu Pro Ser Tyr Ala Asp Asp
    50                  55                  60

Phe Lys Gly Arg Phe Ala Phe Ser Leu Glu Thr Ser Ala Ser Thr Ala
65                  70                  75                  80

Tyr Leu Gln Ile Asn Asn Leu Lys Asn Glu Asp Thr Ala Thr Tyr Phe
                85                  90                  95

Cys Ala Thr Asp Cys Gly Asp Tyr Phe Asp Tyr Trp Gly Gln Gly Thr
            100                 105                 110

Thr Leu Thr Val Ser Ser Ala Lys Thr Thr Pro Pro Ser Val Thr Ser
        115                 120                 125

Gly Gln Ala Gly Gln
        130

<210> SEQ ID NO 22
<211> LENGTH: 133
<212> TYPE: PRT
<213> ORGANISM: Artificial
<220> FEATURE:
<223> OTHER INFORMATION: 202 anti-CD133 antibody heavy chain 53

<400> SEQUENCE: 22

Leu Glu Val Lys Leu Val Glu Ser Gly Pro Glu Leu Lys Lys Pro Gly
1               5                   10                  15

Glu Thr Val Lys Ile Ser Cys Lys Ala Ser Gly Tyr Thr Phe Thr Asp

```
                  20                  25                  30

Tyr Ser Met His Trp Val Asn Gln Ala Pro Gly Lys Gly Leu Lys Trp
        35                  40                  45

Met Gly Trp Ile Asn Thr Glu Thr Gly Glu Pro Ser Tyr Ala Asp Asp
 50                  55                  60

Phe Lys Gly Arg Phe Ala Phe Ser Leu Glu Thr Ser Ala Ser Thr Ala
 65                  70                  75                  80

Tyr Leu Gln Ile Asn Asn Leu Lys Asn Glu Asp Thr Ala Thr Tyr Phe
                85                  90                  95

Cys Ala Thr Asp Tyr Gly Asp Tyr Phe Asp Tyr Trp Gly Gln Gly Thr
                100                 105                 110

Thr Leu Thr Val Ser Ser Ala Lys Thr Thr Pro Pro Ser Val Thr Ser
            115                 120                 125

Gly Gln Ala Gly Gln
        130

<210> SEQ ID NO 23
<211> LENGTH: 133
<212> TYPE: PRT
<213> ORGANISM: Artificial
<220> FEATURE:
<223> OTHER INFORMATION: 202 anti-CD133 antibody heavy chain 54

<400> SEQUENCE: 23

Leu Glu Val Lys Leu Val Glu Ser Gly Pro Glu Leu Lys Lys Pro Gly
 1               5                  10                  15

Glu Thr Val Lys Ile Ser Cys Lys Ala Ser Gly Tyr Thr Phe Thr Asp
                20                  25                  30

Tyr Ser Met His Trp Val Asn Gln Ala Pro Gly Lys Gly Leu Lys Trp
        35                  40                  45

Met Gly Trp Ile Asn Thr Glu Thr Gly Glu Pro Ser Tyr Ala Asp Asp
 50                  55                  60

Phe Lys Gly Arg Phe Ala Phe Ser Leu Glu Thr Ser Ala Ser Thr Ala
 65                  70                  75                  80

Tyr Leu Gln Ile Asn Asn Leu Lys Asn Glu Asp Thr Ala Thr Tyr Phe
                85                  90                  95

Cys Ala Thr Asp Tyr Gly Asp Tyr Phe Asp Tyr Trp Gly Gln Gly Thr
                100                 105                 110

Thr Leu Thr Val Ser Ser Ala Lys Thr Thr Ala Pro Ser Val Thr Ser
            115                 120                 125

Gly Gln Ala Gly Gln
        130

<210> SEQ ID NO 24
<211> LENGTH: 133
<212> TYPE: PRT
<213> ORGANISM: Artificial
<220> FEATURE:
<223> OTHER INFORMATION: 202 anti-CD133 antibody heavy chain 55

<400> SEQUENCE: 24

Leu Glu Val Gln Leu Val Glu Ser Gly Pro Glu Leu Lys Lys Pro Gly
 1               5                  10                  15

Glu Thr Val Lys Ile Ser Cys Lys Ala Ser Gly Tyr Thr Phe Thr Asp
                20                  25                  30

Tyr Ser Met His Trp Val Asn Gln Ala Pro Gly Lys Gly Leu Lys Trp
        35                  40                  45
```

```
Met Gly Trp Ile Asn Thr Glu Thr Gly Glu Pro Ser Tyr Ala Asp Asp
 50                  55                  60

Phe Lys Gly Arg Phe Ala Phe Ser Leu Glu Thr Ser Ala Ser Thr Ala
 65                  70                  75                  80

Tyr Leu Gln Ile Asn Asn Leu Lys Asn Glu Asp Thr Ala Thr Tyr Phe
                 85                  90                  95

Cys Ala Thr Asp Tyr Gly Asp Tyr Phe Asp Tyr Trp Gly Gln Gly Thr
                100                 105                 110

Thr Leu Thr Val Ser Ser Ala Lys Thr Thr Ala Pro Ser Val Thr Ser
                115                 120                 125

Gly Gln Ala Gly Gln
                130
```

<210> SEQ ID NO 25
<211> LENGTH: 219
<212> TYPE: PRT
<213> ORGANISM: Artificial
<220> FEATURE:
<223> OTHER INFORMATION: 4C8 anti-CD34 antibody light chain

<400> SEQUENCE: 25

```
Asp Val Leu Leu Thr Gln Ser Pro Leu Ser Leu Pro Val Thr Leu Gly
 1               5                  10                  15

Gln Pro Ala Ser Ile Ser Cys Arg Ser Ser Gln Thr Ile Val His Ser
                 20                  25                  30

Asn Gly Asn Thr Tyr Leu Glu Trp Phe Gln Gln Arg Pro Gly Gln Ser
                 35                  40                  45

Pro Arg Leu Leu Ile Tyr Gln Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                 85                  90                  95

Ser His Val Pro Arg Thr Phe Gly Gly Gly Thr Lys Val Glu Ile Lys
                100                 105                 110

Arg Thr Val Ala Ala Pro Ser Val Phe Ile Phe Pro Pro Ser Asp Glu
                115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys
                210                 215
```

<210> SEQ ID NO 26
<211> LENGTH: 113
<212> TYPE: PRT
<213> ORGANISM: Artificial
<220> FEATURE:
<223> OTHER INFORMATION: mMY10 anti-CD34 antibody light chain

<400> SEQUENCE: 26

-continued

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Asn Leu Val His Ser
            20                  25                  30

Asn Gly Asn Thr Tyr Leu His Trp Tyr Gln Gln Lys Pro Gly Lys Ala
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Glu Phe Thr Leu Thr Ile
65                  70                  75                  80

Ser Ser Leu Gln Pro Glu Asp Phe Ala Thr Tyr Tyr Cys Ser Gln Ser
                85                  90                  95

Thr His Val Pro Leu Thr Phe Gly Gln Gly Thr Lys Val Glu Ile Lys
                100                 105                 110

Arg

<210> SEQ ID NO 27
<211> LENGTH: 112
<212> TYPE: PRT
<213> ORGANISM: Artificial
<220> FEATURE:
<223> OTHER INFORMATION: 202 anti-CD133 antibody light chain 47

<400> SEQUENCE: 27

Ala Gln Ala Ala Glu Leu Asp Ile Val Leu Thr Gln Ser Pro Ala Ile
1               5                   10                  15

Met Ser Ala Ser Pro Gly Glu Lys Val Thr Ile Ser Cys Ser Ala Ser
            20                  25                  30

Ser Ser Val Gly Tyr Met Tyr Trp Tyr Gln Gln Lys Pro Gly Ser Ser
        35                  40                  45

Pro Lys Pro Trp Ile Tyr Arg Pro Ser Asn Leu Ala Ser Gly Val Pro
    50                  55                  60

Ala Arg Phe Ser Gly Ser Gly Ser Gly Thr Ser Tyr Ser Leu Thr Ile
65                  70                  75                  80

Ser Ser Met Glu Ala Glu Asp Ala Ala Thr Tyr Tyr Cys Gln Gln Tyr
                85                  90                  95

His Ser Tyr Pro Pro Thr Phe Gly Ala Gly Thr Lys Leu Glu Leu Lys
                100                 105                 110

<210> SEQ ID NO 28
<211> LENGTH: 112
<212> TYPE: PRT
<213> ORGANISM: Artificial
<220> FEATURE:
<223> OTHER INFORMATION: 202 anti-CD133 antibody light chain 48

<400> SEQUENCE: 28

Ala Gln Ala Ala Glu Leu Asp Ile Val Leu Thr Gln Ser Pro Ala Ile
1               5                   10                  15

Met Ser Ala Ser Pro Gly Glu Lys Val Thr Ile Ser Cys Ser Ala Ser
            20                  25                  30

Ser Ser Val Ser Tyr Met Tyr Trp Tyr Gln Gln Lys Pro Gly Ser Ser
        35                  40                  45

Pro Lys Pro Trp Ile Tyr Arg Thr Ser Asn Leu Ala Ser Gly Val Pro
    50                  55                  60

Ala Arg Phe Ser Gly Ser Gly Ser Gly Thr Ser Tyr Ser Leu Thr Ile
65                  70                  75                  80

```
Ser Ser Met Glu Ala Glu Asp Ala Ala Thr Tyr Tyr Cys Gln Gln Tyr
            85                  90                  95

His Ser Tyr Pro Pro Thr Phe Gly Ala Gly Thr Lys Leu Glu Leu Lys
            100                 105                 110

<210> SEQ ID NO 29
<211> LENGTH: 112
<212> TYPE: PRT
<213> ORGANISM: Artificial
<220> FEATURE:
<223> OTHER INFORMATION: 202 anti-CD133 antibody light chain 49

<400> SEQUENCE: 29

Ala Gln Ala Ala Glu Leu Asp Ile Val Leu Thr Gln Ser Pro Ala Ile
1               5                   10                  15

Met Ser Ala Ser Pro Gly Glu Lys Val Thr Ile Ser Cys Ser Ala Ser
            20                  25                  30

Ser Ser Val Ser Tyr Met Tyr Trp Tyr Gln Gln Lys Pro Gly Ser Ser
        35                  40                  45

Pro Lys Pro Trp Ile Tyr Arg Pro Ser Asn Leu Ala Ser Gly Val Pro
    50                  55                  60

Ala Arg Phe Ser Gly Ser Gly Ser Gly Thr Ser Tyr Ser Leu Thr Ile
65                  70                  75                  80

Ser Ser Met Glu Ala Glu Asp Ala Ala Thr Tyr Tyr Cys Gln Gln Tyr
            85                  90                  95

His Ser Tyr Pro Pro Thr Phe Gly Ala Gly Thr Lys Leu Glu Leu Lys
            100                 105                 110

<210> SEQ ID NO 30
<211> LENGTH: 112
<212> TYPE: PRT
<213> ORGANISM: Artificial
<220> FEATURE:
<223> OTHER INFORMATION: 202 anti-CD133 antibody light chain 50

<400> SEQUENCE: 30

Ala Gln Ala Ala Glu Leu Asp Ile Val Leu Thr Gln Ser Pro Ala Ile
1               5                   10                  15

Met Ser Ala Ser Pro Gly Glu Lys Val Thr Ile Ser Cys Ser Ala Ser
            20                  25                  30

Ser Ser Val Ser Tyr Met Tyr Trp Tyr Gln Gln Lys Pro Gly Gln Pro
        35                  40                  45

Pro Arg Leu Leu Ile Tyr Leu Val Ser Asn Leu Glu Ser Gly Val Pro
    50                  55                  60

Ala Arg Phe Ser Gly Ser Gly Ser Gly Thr Asp Phe Thr Leu Asn Ile
65                  70                  75                  80

His Pro Val Glu Glu Glu Asp Ala Ala Thr Tyr Tyr Cys Gln Gln Tyr
            85                  90                  95

His Ser Tyr Pro Pro Thr Phe Gly Ala Gly Thr Lys Leu Glu Ile Lys
            100                 105                 110

<210> SEQ ID NO 31
<211> LENGTH: 112
<212> TYPE: PRT
<213> ORGANISM: Artificial
<220> FEATURE:
<223> OTHER INFORMATION: 202 anti-CD133 antibody light chain 51

<400> SEQUENCE: 31
```

Ala Gln Ala Ala Glu Leu Asp Ile Val Leu Thr Gln Ser Pro Ala Ile
1               5                   10                  15

Met Ser Ala Ser Pro Gly Glu Lys Val Thr Ile Ser Cys Ser Ala Ser
            20                  25                  30

Ser Ser Val Ser Tyr Met Tyr Trp Tyr Gln Gln Lys Pro Gly Ser Ser
        35                  40                  45

Pro Lys Pro Trp Ile Tyr Arg Pro Ser Asn Leu Ala Ser Gly Val Pro
    50                  55                  60

Ala Arg Phe Ser Gly Ser Gly Ser Gly Thr Ser Tyr Ser Leu Thr Ile
65                  70                  75                  80

Ser Ser Met Glu Ala Glu Asp Ala Ala Thr Tyr Tyr Cys Gln Gln Tyr
            85                  90                  95

His Ser Tyr Pro Pro Thr Phe Gly Ala Gly Thr Lys Leu Glu Leu Lys
            100                 105                 110

<210> SEQ ID NO 32
<211> LENGTH: 112
<212> TYPE: PRT
<213> ORGANISM: Artificial
<220> FEATURE:
<223> OTHER INFORMATION: 202 anti-CD133 antibody light chain 52

<400> SEQUENCE: 32

Ala Gln Ala Ala Glu Leu Asp Ile Val Leu Ser Gln Ser Pro Ala Ile
1               5                   10                  15

Met Ser Ala Ser Pro Gly Glu Lys Val Thr Ile Ser Cys Ser Ala Ser
            20                  25                  30

Ser Ser Val Ser Tyr Met Tyr Trp Tyr Gln Gln Lys Pro Gly Ser Pro
        35                  40                  45

Pro Lys Pro Trp Ile Tyr Arg Thr Ser Asn Leu Ala Ser Gly Val Pro
    50                  55                  60

Ala Arg Phe Ser Gly Ser Gly Ser Gly Thr Ser Tyr Ser Leu Thr Ile
65                  70                  75                  80

Ser Ser Met Glu Ala Glu Asp Ala Ala Thr Tyr Tyr Cys Gln Gln Tyr
            85                  90                  95

His Ser Tyr Pro Pro Thr Phe Gly Ala Gly Thr Lys Leu Glu Leu Lys
            100                 105                 110

<210> SEQ ID NO 33
<211> LENGTH: 112
<212> TYPE: PRT
<213> ORGANISM: Artificial
<220> FEATURE:
<223> OTHER INFORMATION: 202 anti-CD133 antibody light chain 53

<400> SEQUENCE: 33

Ala Gln Ala Ala Glu Leu Asp Ile Val Leu Ser Gln Ser Pro Ala Ile
1               5                   10                  15

Met Ser Ala Ser Pro Gly Glu Lys Val Thr Ile Ser Cys Ser Ala Ser
            20                  25                  30

Ser Ser Val Ser Tyr Met Tyr Trp Tyr Gln Gln Lys Pro Gly Ser Ser
        35                  40                  45

Pro Lys Pro Trp Ile Tyr Arg Thr Ser Asn Leu Ala Ser Gly Val Pro
    50                  55                  60

Ala Arg Phe Ser Gly Ser Gly Ser Gly Thr Ser Tyr Ser Leu Thr Ile
65                  70                  75                  80

Ser Ser Met Glu Ala Glu Asp Ala Ala Thr Tyr Tyr Cys Gln Gln Tyr
            85                  90                  95

```
His Ser Tyr Pro Pro Thr Phe Gly Ala Gly Thr Lys Leu Glu Leu Lys
                100                 105                 110

<210> SEQ ID NO 34
<211> LENGTH: 112
<212> TYPE: PRT
<213> ORGANISM: Artificial
<220> FEATURE:
<223> OTHER INFORMATION: 202 anti-CD133 antibody light chain 54

<400> SEQUENCE: 34

Ala Gln Ala Ala Glu Leu Asp Ile Val Leu Thr Gln Ser Pro Ala Ile
1               5                   10                  15

Met Ser Ala Ser Pro Gly Glu Lys Val Thr Ile Ser Cys Ser Ala Ser
                20                  25                  30

Ser Ser Val Ser Tyr Met Tyr Trp Tyr Gln Gln Lys Pro Gly Ser Ser
            35                  40                  45

Pro Lys Pro Trp Ile Tyr Arg Pro Ser Asn Leu Ala Ser Gly Val Pro
        50                  55                  60

Ala Arg Phe Ser Gly Ser Gly Ser Gly Thr Ser Tyr Ser Leu Thr Ile
65                  70                  75                  80

Ser Ser Met Glu Ala Glu Asp Ala Ala Thr Tyr Tyr Cys Gln Gln Tyr
                85                  90                  95

His Ser Tyr Pro Pro Thr Phe Gly Ala Gly Thr Lys Leu Glu Leu Lys
                100                 105                 110

<210> SEQ ID NO 35
<211> LENGTH: 112
<212> TYPE: PRT
<213> ORGANISM: Artificial
<220> FEATURE:
<223> OTHER INFORMATION: 202 anti-CD133 antibody light chain 55

<400> SEQUENCE: 35

Ala Gln Ala Ala Glu Leu Asp Ile Val Leu Thr Gln Ser Pro Ala Ile
1               5                   10                  15

Met Ser Ala Ser Pro Gly Glu Lys Val Thr Ile Ser Cys Ser Ala Ser
                20                  25                  30

Ser Ser Val Ser Tyr Met Tyr Trp Tyr Gln Gln Lys Pro Gly Ser Ser
            35                  40                  45

Pro Lys Pro Trp Ile Tyr Arg Pro Ser Asn Leu Ala Ser Gly Val Pro
        50                  55                  60

Ala Arg Phe Ser Gly Ser Gly Ser Gly Thr Ser Tyr Ser Leu Thr Ile
65                  70                  75                  80

Ser Ser Met Glu Ala Glu Asp Ala Ala Thr Tyr Tyr Cys Gln Gln Tyr
                85                  90                  95

His Ser Tyr Pro Pro Thr Phe Gly Ala Gly Thr Lys Leu Glu Leu Lys
                100                 105                 110

<210> SEQ ID NO 36
<211> LENGTH: 16
<212> TYPE: PRT
<213> ORGANISM: Artificial
<220> FEATURE:
<223> OTHER INFORMATION: 1256 anti-CD3 antibody heavy chain CDR3

<400> SEQUENCE: 36

Ala Lys Asp Asn Ser Gly Tyr Gly His Tyr Tyr Gly Met Asp Val
1               5                   10                  15
```

<210> SEQ ID NO 37
<211> LENGTH: 16
<212> TYPE: PRT
<213> ORGANISM: Artificial
<220> FEATURE:
<223> OTHER INFORMATION: 1272 anti-CD3 antibody heavy chain CDR3

<400> SEQUENCE: 37

Ala Lys Asp Asn Ser Gly Tyr Gly Tyr Tyr Tyr Tyr Gly Met Asp Val
1               5                   10                  15

<210> SEQ ID NO 38
<211> LENGTH: 16
<212> TYPE: PRT
<213> ORGANISM: Artificial
<220> FEATURE:
<223> OTHER INFORMATION: 1288 anti-CD3 antibody heavy chain CDR3

<400> SEQUENCE: 38

Ala Lys Asp Asn Ser Gly Tyr Gly His Tyr Tyr Tyr Gly Met Asp Val
1               5                   10                  15

<210> SEQ ID NO 39
<211> LENGTH: 11
<212> TYPE: PRT
<213> ORGANISM: Artificial
<220> FEATURE:
<223> OTHER INFORMATION: 1304 anti-CD3 antibody heavy chain CDR3

<400> SEQUENCE: 39

Ala Arg Gly Pro Gly Tyr Asn Trp Leu Asp Pro
1               5                   10

<210> SEQ ID NO 40
<211> LENGTH: 11
<212> TYPE: PRT
<213> ORGANISM: Artificial
<220> FEATURE:
<223> OTHER INFORMATION: 1320 anti-CD3 antibody heavy chain CDR3

<400> SEQUENCE: 40

Ala Arg Gly Pro Gly Tyr Asn Trp Leu Asp Pro
1               5                   10

<210> SEQ ID NO 41
<211> LENGTH: 12
<212> TYPE: PRT
<213> ORGANISM: Artificial
<220> FEATURE:
<223> OTHER INFORMATION: 1332 anti-CD3 antibody heavy chain CDR3

<400> SEQUENCE: 41

Ala Arg Tyr Tyr Asp Asp His Tyr Cys Leu Asp Tyr
1               5                   10

<210> SEQ ID NO 42
<211> LENGTH: 11
<212> TYPE: PRT
<213> ORGANISM: Artificial
<220> FEATURE:
<223> OTHER INFORMATION: 1334 anti-CD3 antibody light chain CDR1

<400> SEQUENCE: 42

Leu Ser Cys Arg Ala Ser Gln Ser Val Ser Tyr
1               5                   10

```
<210> SEQ ID NO 43
<211> LENGTH: 119
<212> TYPE: PRT
<213> ORGANISM: Artificial
<220> FEATURE:
<223> OTHER INFORMATION: anti-CD3 heavy chain

<400> SEQUENCE: 43

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
                20                  25                  30

Thr Met His Trp Val Lys Gln Arg Pro Gly Gln Gly Leu Glu Trp Ile
            35                  40                  45

Gly Tyr Ile Asn Pro Ser Arg Gly Tyr Thr Asn Tyr Asn Gln Lys Phe
        50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
                100                 105                 110

Thr Thr Leu Thr Val Ser Ser
        115

<210> SEQ ID NO 44
<211> LENGTH: 119
<212> TYPE: PRT
<213> ORGANISM: Artificial
<220> FEATURE:
<223> OTHER INFORMATION: 253 anti-CD3 heavy chain

<400> SEQUENCE: 44

Gln Val Gln Leu Val Gln Ser Gly Ala Glu Val Arg Lys Pro Gly Ala
1               5                   10                  15

Ser Val Arg Val Thr Met His Trp Val Arg Gln Ala Pro Gly His Gly
                20                  25                  30

Leu Glu Trp Ile Gly Tyr Ile Asn Pro Ser Arg Gly Tyr Thr Asn Tyr
            35                  40                  45

Asn Gln Lys Phe Lys Asp Arg Val Thr Met Thr Thr Asp Lys Ser Phe
        50                  55                  60

Ser Thr Ala Ile Met Asp Leu Arg Ser Leu Arg Ser Asp Asp Ser Ala
65                  70                  75                  80

Val Tyr Tyr Cys Ala Arg Tyr Tyr Asp Asp His Tyr Cys Leu Asp Tyr
                85                  90                  95

Trp Gly Gln Gly Thr Thr Val Thr Val Ser Ser Ser Cys Lys Ala Ser
                100                 105                 110

Gly Tyr Thr Phe Thr Arg Tyr
        115

<210> SEQ ID NO 45
<211> LENGTH: 112
<212> TYPE: PRT
<213> ORGANISM: Artificial
<220> FEATURE:
<223> OTHER INFORMATION: 1250 anti-CD3 antibody heavy chain

<400> SEQUENCE: 45

Glu Val Gln Leu Val Glu Ser Gly Gly Gly Leu Val Gln Pro Gly Arg
1               5                   10                  15
```

Ser Leu Arg Leu Ser Cys Ala Ala Ser Gly Phe Thr Phe Asp Asp Tyr
            20                  25                  30

Thr Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Asn Ser Gly Tyr Gly His Tyr Tyr Tyr Gly Met Asp Val
            100                 105                 110

<210> SEQ ID NO 46
<211> LENGTH: 123
<212> TYPE: PRT
<213> ORGANISM: Artificial
<220> FEATURE:
<223> OTHER INFORMATION: 1266 anti-CD3 antibody heavy chain

<400> SEQUENCE: 46

Glu Val Gln Leu Val Glu Ser Gly Gly Gly Leu Val Gln Pro Gly Gly
1               5                   10                  15

Ser Leu Arg Leu Ser Cys Ala Ala Thr Gly Phe Thr Phe Asp Asp Phe
            20                  25                  30

Thr Met His Trp Val Arg Gln Ala Pro Gly Lys Gly Leu Glu Trp Val
        35                  40                  45

Ser Gly Ile Ser Trp Asn Ser Gly Ser Ile Gly Tyr Val Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Asn Ser Gly Tyr Gly Tyr Tyr Tyr Tyr Gly Met Asp Val
            100                 105                 110

Trp Gly Gln Gly Thr Thr Val Thr Val Ser Ser
        115                 120

<210> SEQ ID NO 47
<211> LENGTH: 123
<212> TYPE: PRT
<213> ORGANISM: Artificial
<220> FEATURE:
<223> OTHER INFORMATION: 1282 anti-CD3 antibody heavy chain

<400> SEQUENCE: 47

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Thr Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Ala Glu Asp Thr Ala Leu Tyr Tyr Cys

```
                    85                  90                  95
Ala Lys Asp Asn Ser Gly Tyr Gly His Tyr Tyr Tyr Gly Met Asp Val
            100                 105                 110

Trp Gly Gln Gly Thr Thr Val Thr Val Ala Ser
        115                 120

<210> SEQ ID NO 48
<211> LENGTH: 118
<212> TYPE: PRT
<213> ORGANISM: Artificial
<220> FEATURE:
<223> OTHER INFORMATION: 1298 anti-CD3 antibody heavy chain

<400> SEQUENCE: 48

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Arg Ser Tyr
            20                  25                  30

Ala Met His Trp Val Arg Gln Ala Pro Gly Lys Gly Leu Glu Trp Val
        35                  40                  45

Ala Met Val Tyr Tyr Asp Gly Asn Gln Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Asp Asp Thr Ala Val Tyr Phe Cys
                85                  90                  95

Ala Arg Gly Pro Gly Tyr Asn Trp Leu Asp Pro Trp Gly Gln Gly Thr
            100                 105                 110

Leu Val Thr Val Ser Ser
        115

<210> SEQ ID NO 49
<211> LENGTH: 118
<212> TYPE: PRT
<213> ORGANISM: Artificial
<220> FEATURE:
<223> OTHER INFORMATION: 1314 anti-CD3 antibody heavy chain

<400> SEQUENCE: 49

Gln Val Gln Leu Val Glu Ser Gly Gly Gly Val Val Gln Pro Gly Arg
1               5                   10                  15

Ser Leu Arg Leu Ala Cys Val Ala Ser Gly Phe Thr Phe Arg Ser Tyr
            20                  25                  30

Gly Met His Trp Val Arg Gln Ala Pro Gly Lys Gly Leu Gln Trp Val
        35                  40                  45

Ala Met Ile Tyr Tyr Asp Gly Lys Asn Lys Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Asn Leu Arg Val Glu Asp Thr Ala Met Tyr Phe Cys
                85                  90                  95

Ala Arg Gly Pro Gly Tyr Asn Trp Leu Asp Pro Trp Gly Gln Gly Thr
            100                 105                 110

Leu Val Thr Val Ser Ser
        115

<210> SEQ ID NO 50
<211> LENGTH: 119
```

<212> TYPE: PRT
<213> ORGANISM: Artificial
<220> FEATURE:
<223> OTHER INFORMATION: 1329 anti-CD3 antibody heavy chain

<400> SEQUENCE: 50

Asp Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Gln Ala Pro Gly Gln Gly Leu Glu Trp Ile
        35                  40                  45

Gly Tyr Ile Asn Pro Ser Arg Gly Tyr Thr Asn Tyr Ala Asp Ser Val
    50                  55                  60

Lys Gly Arg Phe Thr Ile Thr Thr Asp Lys Ser Thr Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Tyr Tyr Asp Asp His Tyr Cys Leu Asp Tyr Trp Gly Gln Gly
            100                 105                 110

Thr Thr Val Thr Val Ser Ser
        115

<210> SEQ ID NO 51
<211> LENGTH: 107
<212> TYPE: PRT
<213> ORGANISM: Artificial
<220> FEATURE:
<223> OTHER INFORMATION: 253 anti-CD3 antibody light chain

<400> SEQUENCE: 51

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ser Tyr Met
            20                  25                  30

Asn Trp Tyr Gln Gln Lys Pro Gly Gln Ala Pro Arg Arg Trp Ile Tyr
        35                  40                  45

Asp Thr Ser Lys Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Thr Tyr Tyr Cys Gln Gln Trp Ser Ser Asn Pro Phe Thr
                85                  90                  95

Phe Gly Gly Gly Thr Lys Val Glu Ile Lys Arg
            100                 105

<210> SEQ ID NO 52
<211> LENGTH: 108
<212> TYPE: PRT
<213> ORGANISM: Artificial
<220> FEATURE:
<223> OTHER INFORMATION: 1258 anti-CD3 antibody light chain

<400> SEQUENCE: 52

Ala Glu Ile Val Met Thr Gln Ser Pro Ala Thr Leu Ser Val Ser Pro
1               5                   10                  15

Gly Glu Arg Ala Thr Leu Ser Cys Arg Ala Ser Gln Ser Val Ser Ser
            20                  25                  30

Asn Leu Ala Trp Tyr Gln Gln Lys Pro Gly Gln Ala Pro Arg Leu Leu

```
                35                  40                  45
Ile Tyr Gly Ala Ser Thr Arg Ala Thr Gly Ile Pro Ala Arg Phe Ser
         50                  55                  60

Gly Ser Gly Ser Gly Thr Glu Phe Thr Leu Thr Ile Ser Ser Leu Gln
 65                  70                  75                  80

Ser Glu Asp Phe Ala Val Tyr Tyr Cys Gln His Tyr Ile Asn Trp Pro
                 85                  90                  95

Leu Thr Phe Gly Gly Gly Thr Lys Val Glu Ile Lys
            100                 105

<210> SEQ ID NO 53
<211> LENGTH: 107
<212> TYPE: PRT
<213> ORGANISM: Artificial
<220> FEATURE:
<223> OTHER INFORMATION: 1274 anti-CD3 antibody light chain

<400> SEQUENCE: 53

Glu Ile Val Met Thr Gln Ser Pro Ala Thr Leu Ser Val Ser Pro Gly
 1               5                  10                  15

Glu Arg Ala Thr Leu Ser Cys Arg Ala Ser His Ser Val Ser Arg Asn
             20                  25                  30

Ser Ala Trp Tyr Gln Gln Lys Pro Gly Gln Ala Pro Arg Leu Leu Ile
         35                  40                  45

Tyr Gly Ala Ser Thr Arg Ala Thr Gly Ile Pro Ala Arg Phe Ser Gly
         50                  55                  60

Ser Gly Ser Gly Thr Glu Phe Thr Leu Thr Ile Ser Ser Leu Gln Ser
 65                  70                  75                  80

Glu Asp Phe Ala Ile Tyr Tyr Cys Gln Gln Tyr Asn Asn Trp Pro Leu
                 85                  90                  95

Thr Phe Gly Gly Gly Thr Lys Val Glu Ile Lys
            100                 105

<210> SEQ ID NO 54
<211> LENGTH: 107
<212> TYPE: PRT
<213> ORGANISM: Artificial
<220> FEATURE:
<223> OTHER INFORMATION: 1290 anti-CD3 antibody light chain

<400> SEQUENCE: 54

Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Ser Ser Asn
             20                  25                  30

Leu Ala Trp Tyr Gln Gln Lys Pro Gly Gln Ala Pro Arg Leu Leu Ile
         35                  40                  45

Tyr Gly Ala Ser Thr Arg Ala Thr Gly Ile Pro Ala Arg Phe Ser Gly
         50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln His Tyr Ile Asn Trp Pro Leu
                 85                  90                  95

Thr Phe Gly Gly Gly Thr Lys Val Glu Ile Lys
            100                 105

<210> SEQ ID NO 55
<211> LENGTH: 107
```

```
<212> TYPE: PRT
<213> ORGANISM: Artificial
<220> FEATURE:
<223> OTHER INFORMATION: 1306 anti-CD3 antibody light chain

<400> SEQUENCE: 55

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Arg Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Asp Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Leu
                85                  90                  95

Thr Phe Gly Gly Gly Thr Lys Val Val Ile Lys
            100                 105

<210> SEQ ID NO 56
<211> LENGTH: 107
<212> TYPE: PRT
<213> ORGANISM: Artificial
<220> FEATURE:
<223> OTHER INFORMATION: 1322 anti-CD3 antibody light chain

<400> SEQUENCE: 56

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Arg Ile Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ser Pro Ala Arg Phe Ser Gly
50                  55                  60

Ser Gly Ser Gly Thr Asp Phe Thr Leu Thr Ile Ser Ser Leu Gln Ser
65                  70                  75                  80

Glu Asp Val Ala Val Tyr Tyr Cys Gln Gln His His Asn Trp Pro Leu
                85                  90                  95

Thr Phe Gly Gly Gly Thr Lys Val Glu Ile Lys
            100                 105

<210> SEQ ID NO 57
<211> LENGTH: 106
<212> TYPE: PRT
<213> ORGANISM: Artificial
<220> FEATURE:
<223> OTHER INFORMATION: 1333 anti-CD3 antibody light chain

<400> SEQUENCE: 57

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Tyr Met
            20                  25                  30

Asn Trp Tyr Gln Gln Lys Pro Gly Lys Ala Pro Lys Arg Trp Ile Tyr
        35                  40                  45

Asp Thr Ser Lys Val Ala Ser Gly Val Pro Ala Arg Phe Ser Gly Ser
```

```
                50                  55                  60
Gly Ser Gly Thr Asp Tyr Ser Leu Thr Ile Asn Ser Leu Glu Ala Glu
 65                  70                  75                  80

Asp Ala Ala Thr Tyr Tyr Cys Gln Gln Trp Ser Ser Asn Pro Leu Thr
                 85                  90                  95

Phe Gly Gly Gly Thr Lys Val Glu Ile Lys
                100                 105

<210> SEQ ID NO 58
<211> LENGTH: 15
<212> TYPE: PRT
<213> ORGANISM: Artificial
<220> FEATURE:
<223> OTHER INFORMATION: Linker sequence

<400> SEQUENCE: 58

Gly Gly Gly Gly Ser Gly Gly Gly Ser Gly Gly Gly Gly Ser
 1               5                  10                  15

<210> SEQ ID NO 59
<211> LENGTH: 26
<212> TYPE: PRT
<213> ORGANISM: Artificial
<220> FEATURE:
<223> OTHER INFORMATION: 253 anti-CD3 linker 1

<400> SEQUENCE: 59

Asn Ser Thr Tyr Arg Val Val Ser Val Leu Thr Val Leu His Gln Asp
 1               5                  10                  15

Trp Leu Asn Gly Lys Glu Tyr Lys Cys Lys
                20                  25

<210> SEQ ID NO 60
<211> LENGTH: 25
<212> TYPE: PRT
<213> ORGANISM: Artificial
<220> FEATURE:
<223> OTHER INFORMATION: 253 anti-CD3 linker 2

<400> SEQUENCE: 60

Phe Gln Asn Ala Leu Leu Val Arg Tyr Thr Lys Lys Val Pro Gln Val
 1               5                  10                  15

Ser Thr Pro Thr Leu Val Glu Val Ser
                20                  25

<210> SEQ ID NO 61
<211> LENGTH: 25
<212> TYPE: PRT
<213> ORGANISM: Artificial
<220> FEATURE:
<223> OTHER INFORMATION: 253 anti-CD3 linker 3

<400> SEQUENCE: 61

Ala Ser Ala Asp Asp Ala Lys Lys Asp Ala Lys Lys Asp Asp Ala
 1               5                  10                  15

Lys Lys Asp Asp Ala Lys Lys Asp Leu
                20                  25

<210> SEQ ID NO 62
<211> LENGTH: 18
<212> TYPE: PRT
<213> ORGANISM: Artificial
<220> FEATURE:
<223> OTHER INFORMATION: 202 anti-CD133 antibody linker
```

<400> SEQUENCE: 62

Ser Ser Gly Gly Gly Gly Ser Gly Gly Gly Gly Ser Ser Arg
1               5                   10                  15

Ser Ser

<210> SEQ ID NO 63
<211> LENGTH: 710
<212> TYPE: PRT
<213> ORGANISM: Artificial
<220> FEATURE:
<223> OTHER INFORMATION: anti-CD34-HC-anti-CD3-scFv

<400> SEQUENCE: 63

Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
                20                  25                  30

Gly Met Asn Trp Val Arg Gln Ala Pro Gly Gln Gly Leu Lys Trp Met
            35                  40                  45

Gly Trp Ile Asn Thr Asn Thr Gly Glu Pro Lys Tyr Ala Glu Glu Phe
        50                  55                  60

Lys Gly Arg Phe Ala Leu Ser Leu Asp Thr Ser Val Ser Thr Ala Tyr
65                  70                  75                  80

Leu Gln Ile Asn Ser Leu Lys Ala Glu Asp Thr Ala Val Tyr Phe Cys
                85                  90                  95

Ala Arg Gly Tyr Gly Asn Tyr Ala Arg Gly Ala Trp Leu Ala Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro

```
                    325                 330                 335
Ile Glu Lys Thr Ile Ser Lys Ala Lys Gly Gln Pro Arg Glu Pro Gln
                340                 345                 350

Val Tyr Thr Leu Pro Pro Ser Arg Glu Glu Met Thr Lys Asn Gln Val
                355                 360                 365

Ser Leu Thr Cys Leu Val Lys Gly Phe Tyr Pro Ser Asp Ile Ala Val
                370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
                435                 440                 445

Ser Pro Gly Lys Gly Gly Gly Ser Gly Gly Gly Ser Gly Gly
450                 455                 460

Gly Gly Ser Asp Ile Lys Leu Gln Gln Ser Gly Ala Glu Leu Ala Arg
465                 470                 475                 480

Pro Gly Ala Ser Val Lys Met Ser Cys Lys Thr Ser Gly Tyr Thr Phe
                485                 490                 495

Thr Arg Tyr Thr Met His Trp Val Lys Gln Arg Pro Gly Gln Gly Leu
                500                 505                 510

Glu Trp Ile Gly Tyr Ile Asn Pro Ser Arg Gly Tyr Thr Asn Tyr Asn
                515                 520                 525

Gln Lys Phe Lys Asp Lys Ala Thr Leu Thr Thr Asp Lys Ser Ser Ser
                530                 535                 540

Thr Ala Tyr Met Gln Leu Ser Ser Leu Thr Ser Glu Asp Ser Ala Val
545                 550                 555                 560

Tyr Tyr Cys Ala Arg Tyr Tyr Asp Asp His Tyr Cys Leu Asp Tyr Trp
                565                 570                 575

Gly Gln Gly Thr Thr Leu Thr Val Ser Ser Val Glu Gly Gly Ser Gly
                580                 585                 590

Gly Ser Gly Gly Ser Gly Gly Ser Gly Gly Val Asp Asp Ile Gln Leu
                595                 600                 605

Thr Gln Ser Pro Ala Ile Met Ser Ala Ser Pro Gly Glu Lys Val Thr
                610                 615                 620

Met Thr Cys Arg Ala Ser Ser Ser Val Ser Tyr Met Asn Trp Tyr Gln
625                 630                 635                 640

Gln Lys Ser Gly Thr Ser Pro Lys Arg Trp Ile Tyr Asp Thr Ser Lys
                645                 650                 655

Val Ala Ser Gly Val Pro Tyr Arg Phe Ser Gly Ser Gly Ser Gly Thr
                660                 665                 670

Ser Tyr Ser Leu Thr Ile Ser Ser Met Glu Ala Glu Asp Ala Ala Thr
                675                 680                 685

Tyr Tyr Cys Gln Gln Trp Ser Ser Asn Pro Leu Thr Phe Gly Ala Gly
                690                 695                 700

Thr Lys Leu Glu Leu Lys
705                 710

<210> SEQ ID NO 64
<211> LENGTH: 330
<212> TYPE: PRT
<213> ORGANISM: Artificial
```

<220> FEATURE:
<223> OTHER INFORMATION: anti-CD34-HC-anti-CD3-scFv heavy chain constant
      region

<400> SEQUENCE: 64

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 65
<211> LENGTH: 107
<212> TYPE: PRT
<213> ORGANISM: Artificial
<220> FEATURE:
<223> OTHER INFORMATION: anti-CD3 light chain

<400> SEQUENCE: 65

```
Asp Asp Ile Gln Leu Thr Gln Ser Pro Ala Ile Met Ser Ala Ser Pro
1               5                   10                  15

Gly Glu Lys Val Thr Met Thr Cys Arg Ala Ser Ser Val Ser Tyr
            20                  25                  30

Met Asn Trp Tyr Gln Gln Lys Ser Gly Thr Ser Pro Lys Arg Trp Ile
        35                  40                  45

Tyr Asp Thr Ser Lys Val Ala Ser Gly Val Pro Tyr Arg Phe Ser Gly
    50                  55                  60

Ser Gly Ser Gly Thr Ser Tyr Ser Leu Thr Ile Ser Ser Met Glu Ala
65              70                  75                  80

Glu Asp Ala Ala Thr Tyr Tyr Cys Gln Gln Trp Ser Ser Asn Pro Leu
                85                  90                  95

Thr Phe Gly Ala Gly Thr Lys Leu Glu Leu Lys
            100                 105

<210> SEQ ID NO 66
<211> LENGTH: 8
<212> TYPE: PRT
<213> ORGANISM: Artificial
<220> FEATURE:
<223> OTHER INFORMATION: 1330 anti-CD3 antibody heavy chain CDR1

<400> SEQUENCE: 66

Gly Tyr Thr Phe Thr Arg Tyr Thr
1               5

<210> SEQ ID NO 67
<211> LENGTH: 8
<212> TYPE: PRT
<213> ORGANISM: Artificial
<220> FEATURE:
<223> OTHER INFORMATION: 1254 anti-CD3 antibody heavy chain CDR2

<400> SEQUENCE: 67

Ile Ser Trp Asn Ser Gly Ser Ile
1               5

<210> SEQ ID NO 68
<211> LENGTH: 8
<212> TYPE: PRT
<213> ORGANISM: Artificial
<220> FEATURE:
<223> OTHER INFORMATION: 1270 anti-CD3 antibody heavy chain CDR2

<400> SEQUENCE: 68

Ile Ser Trp Asn Ser Gly Ser Ile
1               5

<210> SEQ ID NO 69
<211> LENGTH: 8
<212> TYPE: PRT
<213> ORGANISM: Artificial
<220> FEATURE:
<223> OTHER INFORMATION: 1286 anti-CD3 antibody heavy chain CDR2

<400> SEQUENCE: 69

Ile Ser Trp Asn Ser Gly Ser Ile
1               5

<210> SEQ ID NO 70
<211> LENGTH: 8
<212> TYPE: PRT
<213> ORGANISM: Artificial
<220> FEATURE:
```

```
<223> OTHER INFORMATION: 1302 anti-CD3 antibody heavy chain CDR2

<400> SEQUENCE: 70

Val Tyr Tyr Asp Gly Asn Asn Gln
1               5

<210> SEQ ID NO 71
<211> LENGTH: 8
<212> TYPE: PRT
<213> ORGANISM: Artificial
<220> FEATURE:
<223> OTHER INFORMATION: 1318 anti-CD3 antibody heavy chain CDR2

<400> SEQUENCE: 71

Ile Tyr Tyr Asp Gly Lys Asn Lys
1               5

<210> SEQ ID NO 72
<211> LENGTH: 8
<212> TYPE: PRT
<213> ORGANISM: Artificial
<220> FEATURE:
<223> OTHER INFORMATION: 1331 anti-CD3 antibody heavy chain CDR2

<400> SEQUENCE: 72

Ile Asn Pro Ser Arg Gly Tyr Thr
1               5

<210> SEQ ID NO 73
<211> LENGTH: 6
<212> TYPE: PRT
<213> ORGANISM: Artificial
<220> FEATURE:
<223> OTHER INFORMATION: 1260 anti-CD3 antibody light chain CDR1

<400> SEQUENCE: 73

Gln Ser Val Ser Ser Asn
1               5

<210> SEQ ID NO 74
<211> LENGTH: 6
<212> TYPE: PRT
<213> ORGANISM: Artificial
<220> FEATURE:
<223> OTHER INFORMATION: 1276 anti-CD3 antibody light chain CDR1

<400> SEQUENCE: 74

His Ser Val Ser Arg Asn
1               5

<210> SEQ ID NO 75
<211> LENGTH: 6
<212> TYPE: PRT
<213> ORGANISM: Artificial
<220> FEATURE:
<223> OTHER INFORMATION: 1292 anti-CD3 antibody light chain CDR1

<400> SEQUENCE: 75

Gln Ser Val Ser Ser Asn
1               5

<210> SEQ ID NO 76
<211> LENGTH: 6
<212> TYPE: PRT
<213> ORGANISM: Artificial
<220> FEATURE:
<223> OTHER INFORMATION: 1308 anti-CD3 antibody light chain CDR1
```

-continued

<400> SEQUENCE: 76

Gln Ser Val Ser Arg Asn
1               5

<210> SEQ ID NO 77
<211> LENGTH: 6
<212> TYPE: PRT
<213> ORGANISM: Artificial
<220> FEATURE:
<223> OTHER INFORMATION: 1324 anti-CD3 antibody light chain CDR1

<400> SEQUENCE: 77

Gln Arg Ile Ser Ser Asn
1               5

<210> SEQ ID NO 78
<211> LENGTH: 9
<212> TYPE: PRT
<213> ORGANISM: Artificial
<220> FEATURE:
<223> OTHER INFORMATION: 1264 anti-CD3 antibody light chain CDR3

<400> SEQUENCE: 78

Gln His Tyr Ile Asn Trp Pro Leu Thr
1               5

<210> SEQ ID NO 79
<211> LENGTH: 9
<212> TYPE: PRT
<213> ORGANISM: Artificial
<220> FEATURE:
<223> OTHER INFORMATION: 1280 anti-CD3 antibody light chain CDR3

<400> SEQUENCE: 79

Gln Gln Tyr Asn Asn Trp Pro Leu Thr
1               5

<210> SEQ ID NO 80
<211> LENGTH: 9
<212> TYPE: PRT
<213> ORGANISM: Artificial
<220> FEATURE:
<223> OTHER INFORMATION: 1296 anti-CD3 antibody light chain CDR3

<400> SEQUENCE: 80

Gln His Tyr Ile Asn Trp Pro Leu Thr
1               5

<210> SEQ ID NO 81
<211> LENGTH: 9
<212> TYPE: PRT
<213> ORGANISM: Artificial
<220> FEATURE:
<223> OTHER INFORMATION: 1312 anti-CD3 antibody light chain CDR3

<400> SEQUENCE: 81

Gln Gln Tyr Asn Asn Trp Pro Leu Thr
1               5

<210> SEQ ID NO 82
<211> LENGTH: 9
<212> TYPE: PRT
<213> ORGANISM: Artificial
<220> FEATURE:
<223> OTHER INFORMATION: 1328 anti-CD3 antibody light chain CDR3

```
<400> SEQUENCE: 82

Gln Gln His His Asn Trp Pro Leu Thr
1               5

<210> SEQ ID NO 83
<211> LENGTH: 9
<212> TYPE: PRT
<213> ORGANISM: Artificial
<220> FEATURE:
<223> OTHER INFORMATION: 1336 anti-CD3 antibody light chain CDR3

<400> SEQUENCE: 83

Gln Gln Trp Ser Ser Asn Pro Leu Thr
1               5

<210> SEQ ID NO 84
<211> LENGTH: 183
<212> TYPE: PRT
<213> ORGANISM: Artificial
<220> FEATURE:
<223> OTHER INFORMATION: anti-CD34-LC

<400> SEQUENCE: 84

Asp Val Leu Leu Thr Gln Ser Pro Leu Ser Leu Pro Val Thr Leu Gly
1               5                   10                  15

Gln Pro Ala Ser Ile Ser Cys Arg Ser Ser Gln Thr Ile Val His Ser
            20                  25                  30

Asn Gly Asn Thr Tyr Leu Glu Trp Phe Gln Gln Arg Pro Gly Gln Ser
        35                  40                  45

Pro Arg Leu Leu Ile Tyr Gln Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Arg Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr
            180
```

The invention claimed is:

1. A therapeutic agent comprising the amino acid sequence:

SEQ ID NO: 63
QIQLVQSGSELKKPGASVKVSCKASGYTFTNYGMNWVRQAPGQGLKWMGW
INTNTGEPKYAEEFKGRFALSLDTSVSTAYLQINSLKAEDTAVYFCARGY
GNYARGAWLAYWGQGTLVTVSSASTKGPSVFPLAPSSKSTSGGTAALGCL
VKDYFPEPVTVSWNSGALTSGVHTFPAVLQSSGLYSLSSVVTVPSSSLGT
QTYICNVNHKPSNTKVDKKVEPKSCDKTHTCPPCPAPELLGGPSVFLFPP
KPKDTLMISRTPEVTCVVVDVSHEDPEVKFNWYVDGVEVHNAKTKPREEQ
YNSTYRVVSVLTVLHQDWLNGKEYKCKVSNKALPAPIEKTISKAKGQPRE
PQVYTLPPSREEMTKNQVSLTCLVKGFYPSDIAVEWESNGQPENNYKTTP
PVLDSDGSFFLYSKLTVDKSRWQQGNVFSCSVMHEALHNHYTQKSLSLSP

-continued
```
GKGGGGSGGGGSGGGGSDIKLQQSGAELARPGASVKMSCKTSGYTFTRYT

MHWVKQRPGQGLEWIGYINPSRGYTNYNQKFKDKATLTTDKSSSTAYMQL

SSLTSEDSAVYYCARYYDDHYCLDYWGQGTTLTVSSVEGGSGGSGGSGGS

GGVDDIQLTQSPAIMSASPGEKVTMTCRASSSVSYMNWYQQKSGTSPKRW

IYDTSKVASGVPYRFSGSGSGTSYSLTISSMEAEDAATYYCQQWSSNPLT

FGAGTKLELK.
```

2. A pharmaceutical composition comprising the therapeutic agent according to claim 1 and a pharmaceutically-acceptable diluent, carrier or excipient.

\* \* \* \* \*

UNITED STATES PATENT AND TRADEMARK OFFICE
CERTIFICATE OF CORRECTION

PATENT NO. : 10,106,623 B2  
APPLICATION NO. : 15/118767  
DATED : October 23, 2018  
INVENTOR(S) : Uhlin et al.

Page 1 of 1

It is certified that error appears in the above-identified patent and that said Letters Patent is hereby corrected as shown below:

In the Specification

Column 5, Line 1: Please correct "FIG. 1B" to read -- FIG. 1B. --

Column 21, Line 44: Please correct "stein" to read -- stem --

Column 27, Line 35: Please correct "BITE" to read -- BiTE --

Column 38, Line 43: Please remove the word "or"

Column 45, Lines 10-11: Please remove the paragraph break between the words "located." and "The"

Column 45, Line 19: Please correct "111In" to read -- $^{111}$In --

Column 46, Line 30: Please correct "SEQ ID NO: 48" to read -- SEQ ID NO: 38 --

Column 46, Line 56: Please correct "SEQ ID NO: 44" to read -- SEQ ID NO: 42 --

Column 48, Line 67: Please remove the word "or"

Column 49, between SEQ ID NO: 56 and SEQ ID NO: 57: Please remove the word "or"

Column 51, Line 3: Please correct "Kola" to read -- Kortt --

Signed and Sealed this  
Twenty-second Day of January, 2019

Andrei Iancu  
*Director of the United States Patent and Trademark Office*